US007919594B2

(12) United States Patent
Smith et al.

(10) Patent No.: US 7,919,594 B2
(45) Date of Patent: Apr. 5, 2011

(54) HUMAN ANTI-CD100 ANTIBODIES

(75) Inventors: Ernest S. Smith, Ontario, NY (US);
Terrence Lee Fisher, Jr., Rochester, NY (US); Maurice Zauderer, Pittsford, NY (US)

(73) Assignee: Vaccinex, Inc., Rochester, NY (US)

( * ) Notice: Subject to any disclaimer, the term of this patent is extended or adjusted under 35 U.S.C. 154(b) by 0 days.

(21) Appl. No.: 12/030,356

(22) Filed: Feb. 13, 2008

(65) Prior Publication Data

US 2008/0219971 A1 Sep. 11, 2008

Related U.S. Application Data

(60) Provisional application No. 60/901,530, filed on Feb. 14, 2007.

(51) Int. Cl.
*C12P 21/08* (2006.01)
*C07K 16/00* (2006.01)
*C07K 17/00* (2006.01)
*A61K 39/395* (2006.01)
*A61K 39/00* (2006.01)

(52) U.S. Cl. ............... 530/387.3; 424/130.1; 424/133.1; 424/141.1; 424/178.1; 530/387.1; 530/388.1; 530/391.1

(58) Field of Classification Search .................. None
See application file for complete search history.

(56) References Cited

U.S. PATENT DOCUMENTS

| 6,576,754 B2 | 6/2003 | Hall et al. |
| 2003/0158402 A1 | 8/2003 | Hall et al. |
| 2006/0233793 A1 | 10/2006 | Belin et al. |

FOREIGN PATENT DOCUMENTS

| WO | WO 93/14125 A1 | 7/1993 |
| WO | WO 95/07706 A1 | 3/1995 |
| WO | WO 97/17368 A1 | 5/1997 |
| WO | WO 2004/067034 A1 | 8/2004 |
| WO | WO 2006/110594 A2 | 10/2006 |

OTHER PUBLICATIONS

Skolnick and Fetrow. From genes to protein structure and function: novel applications of computational approaches in the genomic era. Trends in Biotechnology, 2000. vol. 18, pp. 34-39.*
Burgess, Shaheen, Ravera, Jaye, Donohue, and Winkles. Possible dissociation of the heparin-binding and mitogenic activities of heparin-binding (acidic fibroblast) growth factor-1 from it's receptor-binding activities by site directed mutagenesis of a single lysine residue. Journal of Cell Biology, 1990. vol. 111, pp. 2129-2138.*
Lazar, Watanabe, Dalton, and Sporn. Transforming growth factor alpha: mutation fo aspartic acid 47 and leucine 48 results in different biological activities. Molecular and Cellular Biology, 1988. vol. 8, pp. 1247-1252.*
Rudikoff, Giusti, Cook, and Scharff. Single amino acid substitution altering antigen-binding specificity. Proceedings of the National Academy of Sciences, 1982. vol. 79, pp. 1979-1983.*
Mac Callum, Martin, and Thornton. Antibody-antigen interactions: contact analysis and binding site topography. Journal of Molecular Biology, 1996. vol. 262, pp. 732-745.*
De Pascalis, Iwahashi, Tamura, Padlan, Gonzales, Santos, Giuliano, Schuck, Scholm, and Kashmiri. Grafting of abbreviated complementarity determining regions containing specificity determining residues essential for ligand contact to engineer a less immunogenic humanized monoclonal antibody. Journal of Immunology, 2002. vol. 169, pp. 3076-3084.*
Casset, Roux, Mouchet, Bes, Chardes, Granier, Mani, Pugniere, Laune, Pau, Kaczorek, Lahana, and Rees. A peptide mimetic of an anti CD4 monoclonal antibody by rational design. Biochemical and Biophysical Research Communications, 2003. vol. 307, pp. 198-205.*
Vajdos, Adams, Breece, Presta, De Vos, and Sidhu. Comprehensive functional maps of the antigen-binding site of an anti-ErbB2 antibody obtained with shotgun scanning mutagenesis. Journal of Molecular Biology, 2002. vol. 320, pp. 415-428.*
Holm, Jafari, and Sundstrom. Functional mapping and single chain construction of the anti-cytokeratin 8 monoclonal antibody TS1. Molecular Immunology, 2007. vol. 44, pp. 1075-1084.*
Chen, Wiesmann, Fuh, Li, Christinger, Mc Kay, De Vos, and Lowman. Selection and analysis of an optimized anti-VEGF antibody: crystal structure of an affinity matured Fab in complex with antigen. Journal of Molecular Biology, 1999. vol. 293, pp. 865-881.*
Wu, Nie, Huse, and Watkins. Humanization of a murine monoclonal antibody by simultaneous optimization of framework and CDR residues. Journal of Molecular Biology, 1999. vol. 294, pp. 151-162.*
Reff and Heard. A review of modifications to recombinant antibodies: attempt to increase efficacy in oncology applications. Critical Reviews in Oncology/ Hematology, 2001. vol. 40, pp. 25-35.*
Basile, J., et al., "Semaphorin 4D Provides a Link Between Axon Guidance Processes and Tumor-Induced Angiogenesis," *Proc. Nat'l. Acad. Sci. USA*, 2006, pp. 9017-9022, vol. 103(24).

(Continued)

*Primary Examiner* — Anne M. Gussow
(74) *Attorney, Agent, or Firm* — Alston & Bird LLP

(57) ABSTRACT

Compositions and methods are provided for treating diseases associated with CD100, including certain types of cancers, autoimmune diseases, inflammatory diseases including central nervous system (CNS) and peripheral nervous system (PNS) inflammatory diseases, transplant rejections, and invasive angiogenesis. Compositions include anti-CD100 antibodies capable of binding to a soluble human CD100 antigen or a CD100 antigen located on the surface of a human CD100-expressing cell, wherein the antibody has CD100 blocking activity that is achieved by having at least one optimized CDR or FWR engineered within the variable region of the antibody. Compositions also include antigen-binding fragments, variants, and derivatives of the monoclonal antibodies, cell lines producing these antibody compositions, and isolated nucleic acid molecules encoding the amino acid sequences of the antibodies. The invention further includes pharmaceutical compositions comprising the anti-CD100 antibodies of the invention, or antigen-binding fragments, variants, or derivatives thereof, in a pharmaceutically acceptable carrier, and methods of use of these anti-CD100 antibodies.

36 Claims, 20 Drawing Sheets

OTHER PUBLICATIONS

Billard, C., et al. "Switch in the Protein Tyrosine Phosphatase Associated with Human CD100 Semaphorin at Terminal B-Cell Differentiation Stage," *Blood*, 2000, pp. 965-972, vol. 95(3).

Bougeret, C., et al., "Increased Surface Expression of a Newly Identified 150-kDa Dimer Early After Human T Lymphocyte Activation," *The Journal of Immunology*, 1992, pp. 318-323, vol. 148(2).

Claesson-Welsh, L., "Novel Paths to Blood Vessel Formation," *Blood*, 2005, pp. 4153-4154, vol. 105(11).

Conrotto, P., et al., "Sema4D Induces Angiogenesis Through Met Recruitment by Plexin B1," *Blood*, 2005, pp. 4321-4329, vol. 105(11).

Deaglio, S., et al., "CD38 and CD100 Lead a Network of Surface Receptors Relaying Positive Signals for B-CLL Growth and Survival," *Blood*, 2005, pp. 3042-3050, vol. 105(8).

Delaire, S., et al., "Biological Activity of Soluble CD100. II. Soluble CD100, Similarly to H-SemaIII, Inhibits Immune Cell Migration," *The Journal of Immunology*, 2001, pp. 4348-4354, vol. 166.

Delaire, S., et al., "Inhibition of Immune Cell Migration by Soluble CD100 and H-Sema III Semaphorins," *Tissue Antigens*, 2000, p. 103, vol. 55(Supp. 1).

Elhabazi, A., et al., "Biological Activity of Soluble CD100. I. The Extracellular Region of CD100 is Released from the Surface of T Lymphocytes by Regulated Proteolysis," *The Journal of Immunology*, 2001, pp. 4341-4347, vol. 166.

Elhabazi, A., et al., "The Human Semaphorin-Like Leukocyte Cell Surface Molecule CD100 Associates with a Serine Kinase Activity," *The Journal of Biological Chemistry*, 1997, pp. 23515-23520, vol. 272(38).

Elhabazi, A., et al., "Structure and Function of the Immune Semaphorin CD100/SEMA4D," *Critical View™ in Immunology*, 2003, pp. 65-81, vol. 23(1&2).

Fishwild, D.M., et al., "High-Avidity Human IgGκ Monoclonal Antibodies from a Novel Strain of Minilocus Transgenic Mice," *Nature Biotechnology*, 1996, pp. 845-851, vol. 14.

Gauld, S., et al., "B Cell Antigen Receptor Signaling: Roles in Cell Development and Disease," *Science*, 2002, pp. 1641-1642, vol. 296.

Giraudon, P., et al., "Semaphorin CD100 from Activated T Lymphocytes Induces Process Extension Collapse in Oligodendrocytes and Death of Immature Neutral Cells," *Journal of Immunology*, 2004, pp. 1246-1255, vol. 172(2).

Hall, K., et al., "Human CD100, A Novel Leukocyte Semaphorin That Promotes B-Cell Aggregation and Differentiation," *Proc Natl Sci USA*, 1996, pp. 11780-11785, vol. 93.

Herold, C., et al., "Activation Signals Are Delivered Through Two Distinct Epitopes of CD100, A Unique 150 kDa Human Lymphocyte Surface Structure Previously Defined by BB18 mAb," *International Immunology*, 1995, pp. 1-8, vol. 7(1).

Herold, C., et al., "CD100 Defines a Newly Identified 150-kDa Human Lymphocyte Surface Structure," 1994, In Schlossman, S. et al., eds. *Leukocyte Typing V*, Section T, Oxford University Press, Oxford.

Ishida, L., et al., "Involvement of CD100, A Lymphocyte Semaphorin, in the Activation of the Human Immune System Via CD72: Implications for the Regulation of Immune and Inflammatory Responses," *International Immunology*, 2003, pp. 1027-1034, vol. 15(8).

Kruger, R.P., et al., "Semaphorins Command Cells to Move," *Nature Reviews Molecular Cell Biology*, 2005, pp. 789-800, vol. 6.

Kumanogoh, A., and H. Kikutani, "The CD100-CD72 Interaction: A Novel Mechanism of Immune Regulation," *Trends in Immunology*, 2001, pp. 670-676, vol. 22(12).

Kumanogoh, A., et al., "Class IV Semaphorin Sema4A Enhances T-Cell Activation and Interacts with Tim-2," *Nature*, 2002, pp. 629-633, vol. 419(6907).

Kumanogoh, A., and H. Kikutani, "Immune Semaphorins: A New Area of Semaphorin Research," *Journal of Cell Science*, 2003, pp. 3463-3470, vol. 116.

Kumanogoh, A., et al., "Requirement for CD100-CD72 Interactions in Fine-Tuning B-Cell Antigen Receptor Signaling and Homeostatic Maintenance of the B-Cell Compartment," *International Immunology*, 2005, pp. 1277-1282, vol. 17(10).

Kumanogoh, A., et al., "Requirement for the Lymphocyte Semaphorin, CD100, in the Induction of Antigen-Specific T Cells and the Maturation of Dendritic Cells," *Journal of Immunology*, 2002, pp. 1175-1181, vol. 169(3).

Li, D.H., et al., "CD72 Down-Modulates BCR-Induced Signal Transduction and Diminishes Survival in Primary Mature B Lymphocytes," *The Journal of Immunology*, 2006, pp. 5321-5328, vol. 176.

Shi, W., et al., "The Class IV Semaphorin CD100 Plays Nonredundant Roles in the Immune System: Defective B and T Cell Activation in CD100-Deficient Mice," *Immunity*, 2000, pp. 633-642, vol. 13.

Turner, L.J., and A. Hall, "Plexin-Induced Collapse Assay in COS Cells," *Methods in Enzymology*, 2006, pp. 665-676, vol. 406.

Wang, X., et al., "Functional Soluble CD100/Sema4D Released from Activated Lymphocytes: Possible Role in Normal and Pathologic Immune Responses," *Blood*, 2001, pp. 3498-3504, vol. 97(11).

Watanabe, C., et al., "Enhanced Immune Responses in Transgenic Mice Expressing a Truncated Form of the Lymphocyte Semaphorin CD100," *The Journal of Immunology*, 2001, pp. 4321-4328, vol. 167.

Zhu, L., et al., "Semaphorin 4D (CD100) Is Expressed on the Surface of Human Platelets and Proteolytically Shed During Platelet Activation," *Blood*, 2003, vol. 102(11).

* cited by examiner

Antigen→ CD100-Fc

Antigen→ huErb2-Fc (Neg Ctrl)

HUMAN ANTI-CD100 ANTIBODIES

CROSS-REFERENCE TO RELATED APPLICATIONS

This application claims the benefit of U.S. Provisional Application No. 60/901,530, filed Feb. 14, 2007, herein incorporated by reference in its entirety.

REFERENCE TO SEQUENCE LISTING SUBMITTED ELECTRONICALLY

The official copy of the sequence listing is submitted electronically via EFS-Web as an ASCII formatted sequence listing with a file named 340176SEQLIST.txt, created on Feb. 12, 2008, and having a size of 48 kilobytes and is filed concurrently with the specification. The sequence listing contained in this ASCII formatted document is part of the specification and is herein incorporated by reference in its entirety.

FIELD OF THE INVENTION

The invention relates to antibodies capable of binding to CD100, methods of using the antibodies, and methods for treatment of diseases associated with CD100-expressing cells.

BACKGROUND OF THE INVENTION

CD100 is a 150-kDa transmembrane protein of the class IV semaphorin subfamily (Delaire et al. (1998) Cell. Mol. Life. Sci. 54:1265-1276; Kumanogoh and Kikutani (2001) Trends Immunol. 22:670-676; Kikutani and Kumanogoh (2003) Nat. Rev. Immunol. 3:159-167). CD100 is expressed at high levels in lymphoid organs, including the spleen, thymus, and lymph nodes, and in non-lymphoid organs, such as the brain, heart, and kidney. In lymphoid organs, CD100 is abundantly expressed on resting T cells but only weakly expressed on resting B cells and antigen-presenting cells (APCs), such as dendritic cells (DCs). Its expression, however, is upregulated in these cells following treatment with various immunological stimuli. The release of soluble CD100 from immune cells is also dependent on cell activation.

The expression patterns of CD100 and its high-affinity receptor, plexin-B1, imply a role in axonal guidance. In Drosophila, plexin-B controls the axonal guidance of certain motor neurons by enhancing Rho signaling (Hu et al. (2001) Neuron 32:39-51). CD100 binding to plexin-B1 results in RhoA activation by regulating PDZ-RhoGEF/LARG, the GEF responsible for CD100-induced growth cone collapse in primary hippocampal neurons (Swiercz et al. (2002) Neuron 35:51-63). In addition, CD100 triggers the invasive growth of epithelial cells, including cell-cell dissociation, anchorage-independent growth, and branching morphogenesis by binding to the plexin-B1-Met complex (Giordano et al. (2002) Nat. Cell Biol. 4:720-724).

As CD100 has been implicated in the development of autoimmune diseases, demyelinating diseases, and certain cancers, compositions which block the activity of CD100 are needed.

BRIEF SUMMARY OF THE INVENTION

Compositions and methods are provided for treating diseases associated with CD100, including certain types of cancers, autoimmune diseases, inflammatory diseases including central nervous system (CNS) and peripheral nervous system (PNS) inflammatory diseases, transplant rejections, and invasive angiogenesis. Compositions include anti-CD100 antibodies capable of binding to a human CD100 antigen located on the surface of a human CD100-expressing cell or secreted by a human CD100-expressing cell, wherein the antibody has CD100 blocking activity. Compositions also include antigen-binding fragments, variants, and derivatives of the monoclonal antibodies, cell lines producing these antibody compositions, and isolated nucleic acid molecules encoding the amino acid sequences of the antibodies. The invention further includes pharmaceutical compositions comprising the anti-CD100 antibodies of the invention, or antigen-binding fragments, variants, or derivatives thereof, in a pharmaceutically acceptable carrier.

The monoclonal antibodies disclosed herein have a strong affinity for CD100 and are characterized by blocking CD100 activity. The antibodies of the invention modulate CD100 signaling in cells expressing the antigen. The antibodies of the invention are capable of specifically binding to a human CD100 antigen expressed on the surface of or secreted by a human cell and are characterized by blocking CD100 associated activity. Compositions of the invention comprise anti-human CD100 antibodies, and antigen-binding antibody fragments, variants, and derivatives thereof. Compositions also include anti-human CD100 antibodies, and antigen-binding antibody fragments, variants and derivatives thereof comprising at least one optimized CDR.

In one embodiment of the invention, methods of treatment comprise administering to a patient a therapeutically effective dose of a pharmaceutical composition comprising suitable anti-CD100 antibodies, or antigen-binding fragments, variants, or derivatives thereof. Diseases associated with CD100-expressing cells include autoimmune diseases, CNS and PNS inflammatory diseases, demyelinating diseases, certain types of cancers, inflammatory diseases, organ and tissue graft rejections, and invasive angiogenesis. Lymphomas that can be treated or prevented by a method of the invention include non-Hodgkin's lymphomas (high-grade lymphomas, intermediate grade lymphomas, and low grade lymphomas), Hodgkin's disease, acute lymphoblastic leukemias, myelomas, chronic lymphocytic leukemias, and myeloblastic leukemias.

The methods are also useful for the treatment of T cell neoplasms, including T cell prolymphocytic leukemia, T cell large granular lymphocytic leukemia, aggressive NK cell leukemia, adult T cell leukemia/lymphoma, extranodal NK/T cell lymphoma, enteropathy-type T cell lymphoma, hepatosplenic T cell lymphoma, blastic NK cell lymphoma, mycosis fungoides/Sezary syndrome, primary cutaneous CD30-positive T cell lymphoproliferative disorders (including primary cutaneous anaplastic large cell lymphoma and lymphomatoid papulosis), angioimmunoblastic T cell lymphoma, peripheral T cell lymphoma, anaplastic large cell lymphoma.

The methods are also useful for the treatment of epithelial cell carcinomas, including, for example, squamous cell carcinomas, basal cell carcinomas, transitional cell carcinomas, adenocarcinomas, adnexal carcinomas, mucoepidermoid carcinomas, mucinous carcinomas, serous carcinomas, ductal carcinomas, lobular carcinomas, medullary carcinomas, acinar cell carcinomas, and melanomas.

Particular autoimmune diseases contemplated for treatment using the methods of the invention include those which involve autoreactive B and/or T cells including, for example, systemic lupus erythematosus (SLE), rheumatoid arthritis, Crohn's disease, psoriasis, autoimmune thrombocytopenic purpura, multiple sclerosis, ankylosing spondylitis, myasthenia gravis, and pemphigus vulgaris.

Particular central nervous system (CNS) or peripheral nervous system (PNS) inflammatory diseases contemplated for treatment using the methods of the invention include multiple sclerosis, demyelinating diseases, oligodendrogliomas and leucodystrophies, HTLV-1 associated myelopathy/tropical spastic paraparesis, Guillain-Barre syndrome, Alexander disease, Canavan disease, Krabbe disease, Pelizaeus-Merzbacher disease, Zellweger disease, Refsum disease, CACH disease, X-linked adrenoleucodystrophy, adrenoleucodystrophy, adrenomyeloneuropathy or leucodystrophies of undetermined origin, or polyradiculoneuritis as well as chronic polyradiculoneuritis.

BRIEF DESCRIPTION OF THE DRAWINGS/FIGURES

FIG. 1 diagrams the selection of chimeric and humanized anti-CD100 VH and VK domains. Black shading represents mouse framework residues, gray shading represents mouse CDR residues, and white represents human framework residues. H387 (SEQ ID NO:3) contains the BD16 VH gene cloned onto the human gamma I heavy chain. H1235 (SEQ ID NO:1) contains BD16 CDRs and four mouse framework residues. H1651 (SEQ ID NO:2) contains BD16 CDRs and fully humanized framework residues. L124 (SEQ ID NO:5) contains the BD16VL gene cloned onto the human Kappa constant domain. L284 (SEQ ID NO: 4) contains BD16 CDRs and fully humanized framework residues.

FIGS. 2A and 2B demonstrate binding of MAb 301 and MAb 657 to CD100-Fc antigen (FIG. 2A), or huErb2-Fc antigen (FIG. 2B). MAb 271 is a control chimeric MAb.

Figure 6:
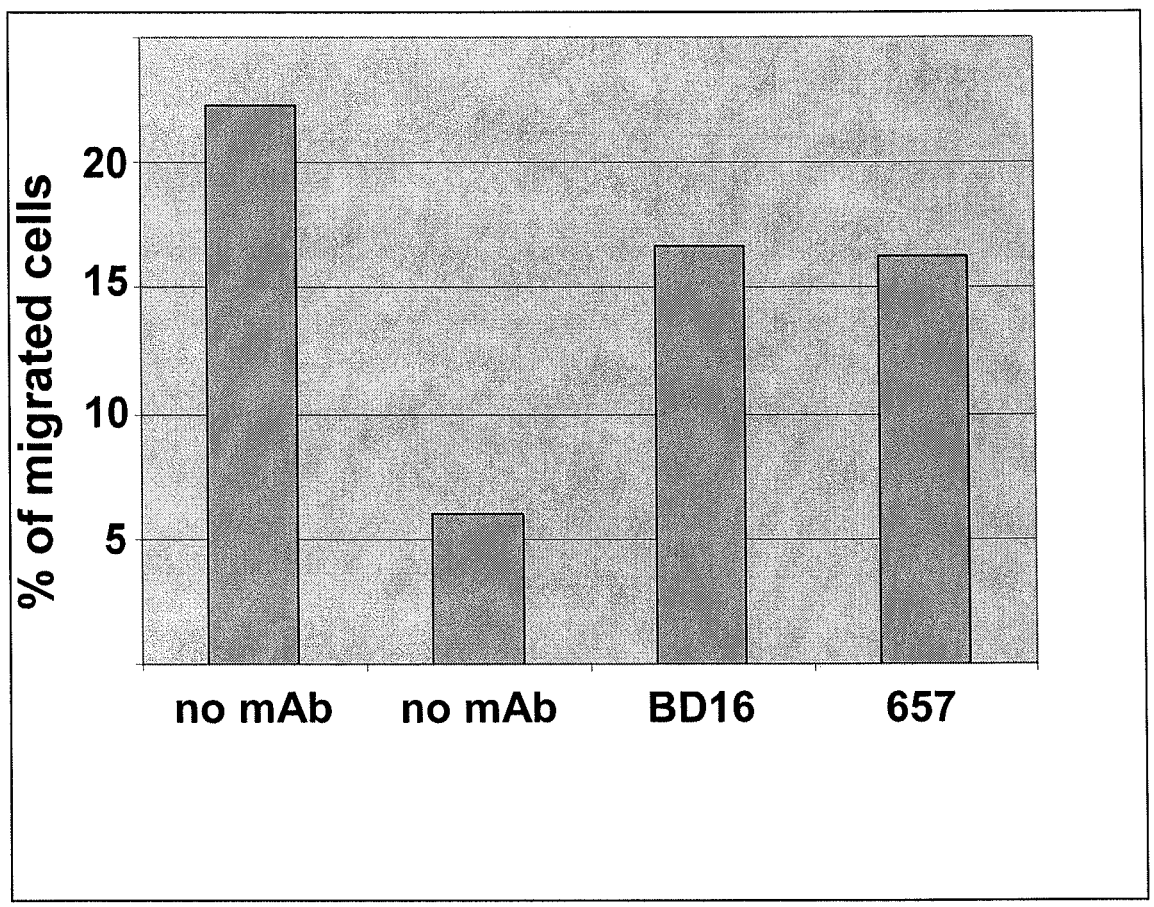

FIG. 6 demonstrates the suppression of CD100-induced inhibition of monocyte migration using MAb 657 and BD16. The effect of MAb 657 is analagous to the effect of mouse BD16.

Figure 7:
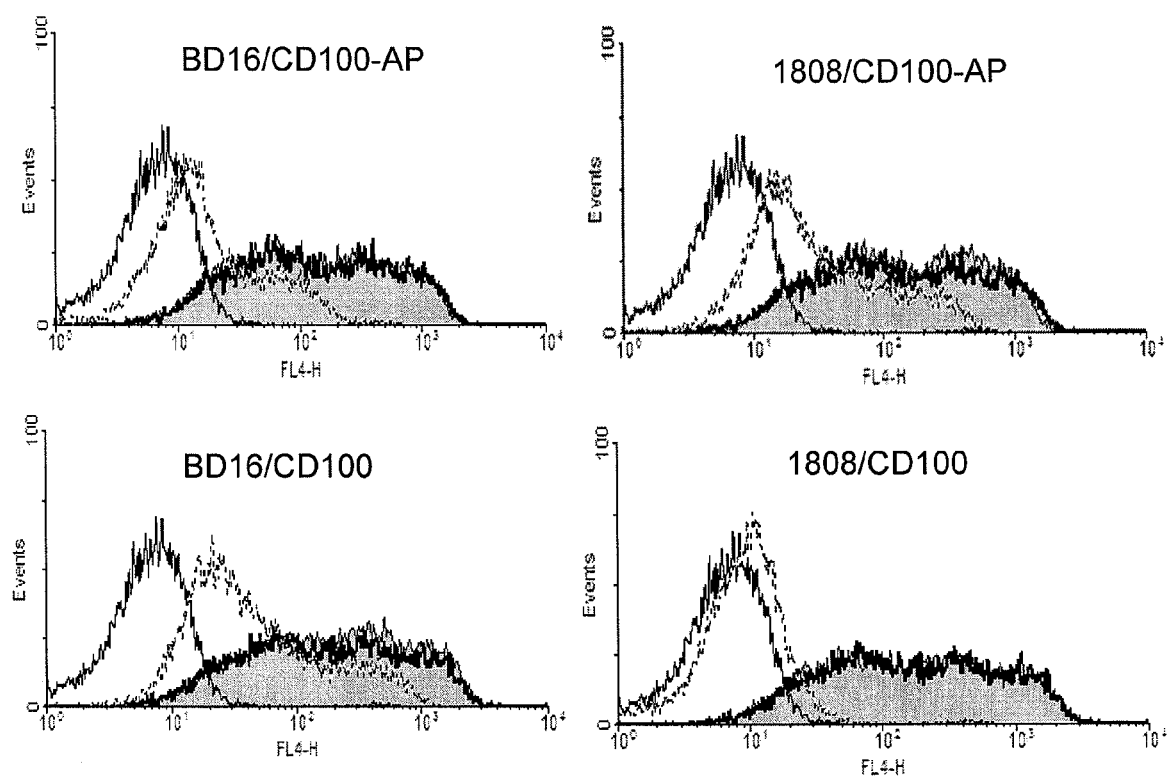

FIG. 7 demonstrates the blocking activity of BD16 and MAb 1808 in CD100-AP or CD100 binding to Plexin B1. The black outline with no shading represents treatment with rabbit anti-his antibody and streptavidin-APC alone, with no CD100; the bold outline with no shading represents 20 ng CD100 or CD100-AP in the absence of antibody, the gray shading depicts 20 ng CD100 or CD100-AP with 20 µg mouse IgG1 isotype control. The dashed outline with no shading represents 20 ng CD100 or CD100-AP with 20 µg BD16 or MAb 1808. Similar blocking was observed when MAb 1808 was compared to MAb 1807 and MAb 657 (not shown).

Figure 8:
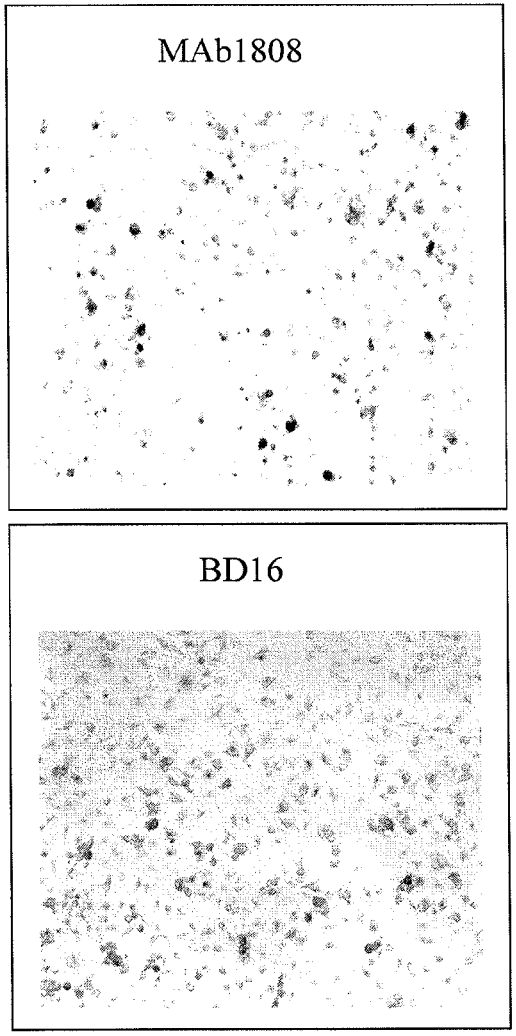
Figure 8:
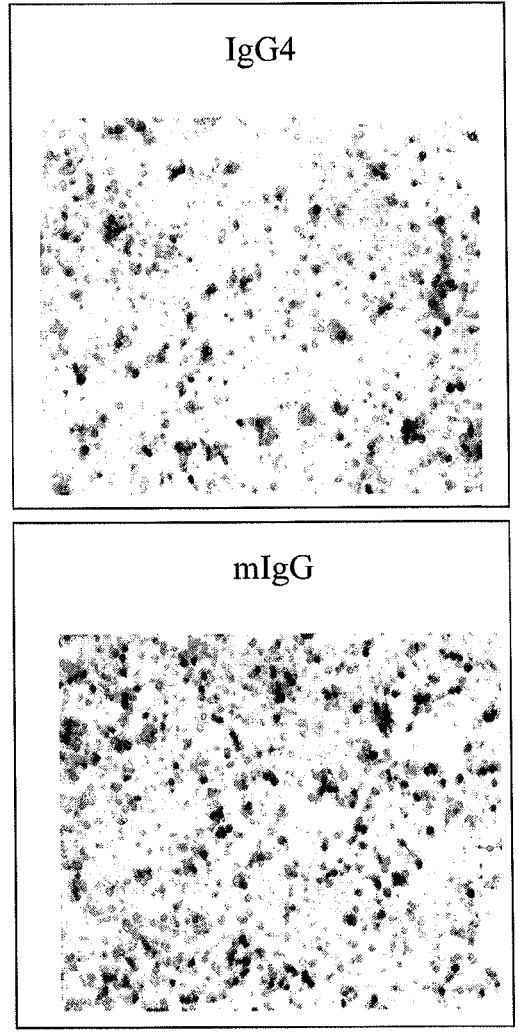
Figure 8:
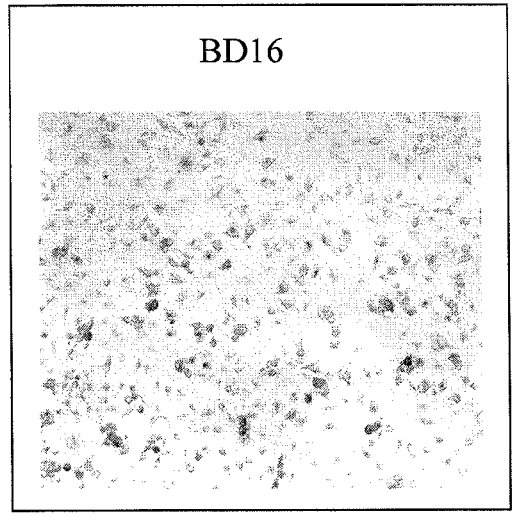
Figure 8:
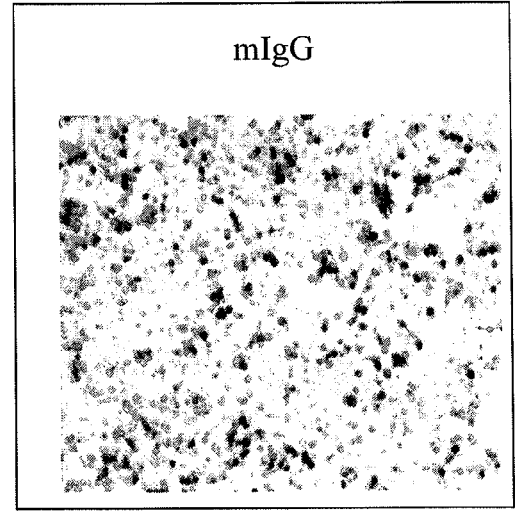

FIG. 8 demonstrates neutralization of CD100 binding to Plexin B1 using BD16, MAb 1808, or control antibodies against mouse IgG1 and human IgG4. Alkaline phosphatase staining is shown in black.

Figure 9:
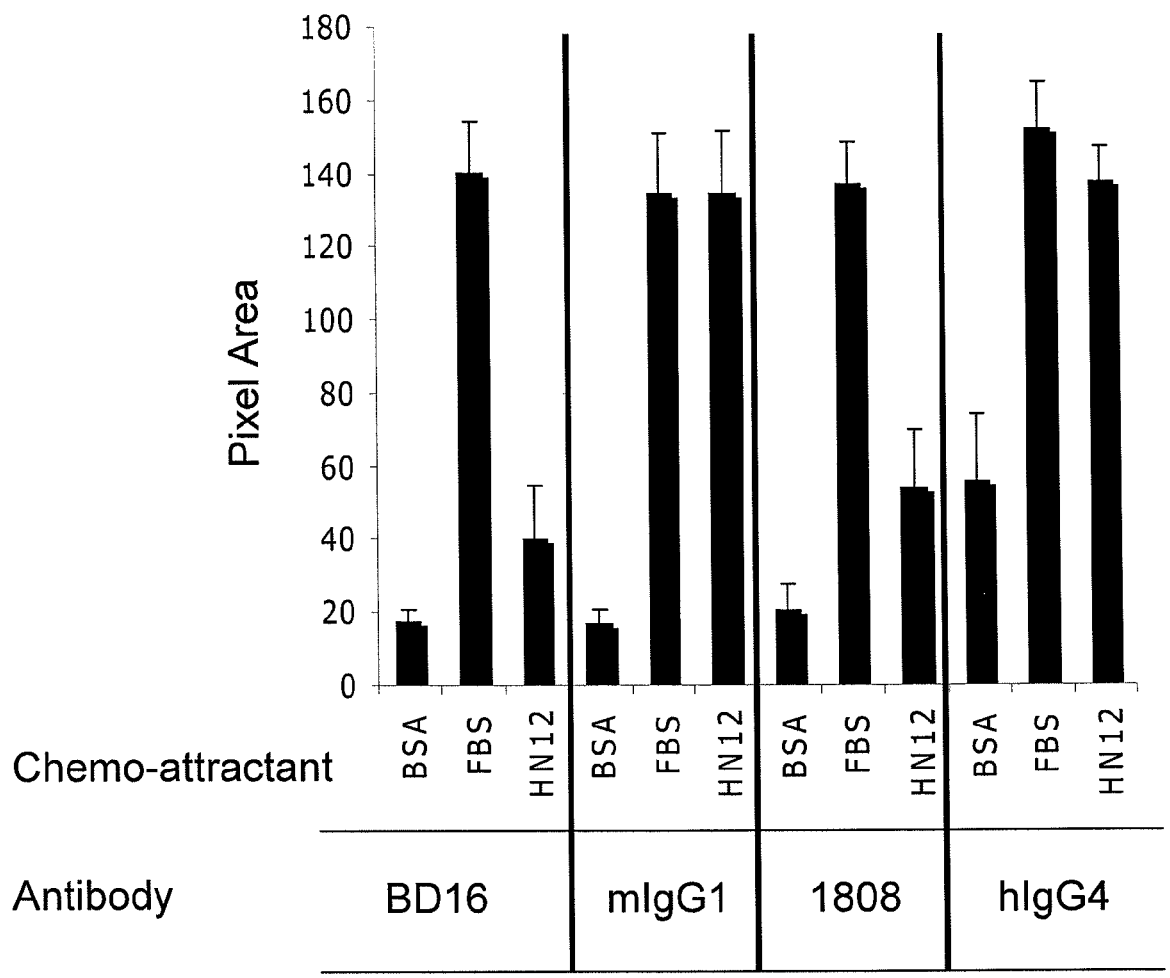

FIG. 9 shows neutralization of CD100 induced HUVEC migration using BD16, MAb 1808, or control antibodies against mouse IgG1 and human IgG4.

Figure 10:
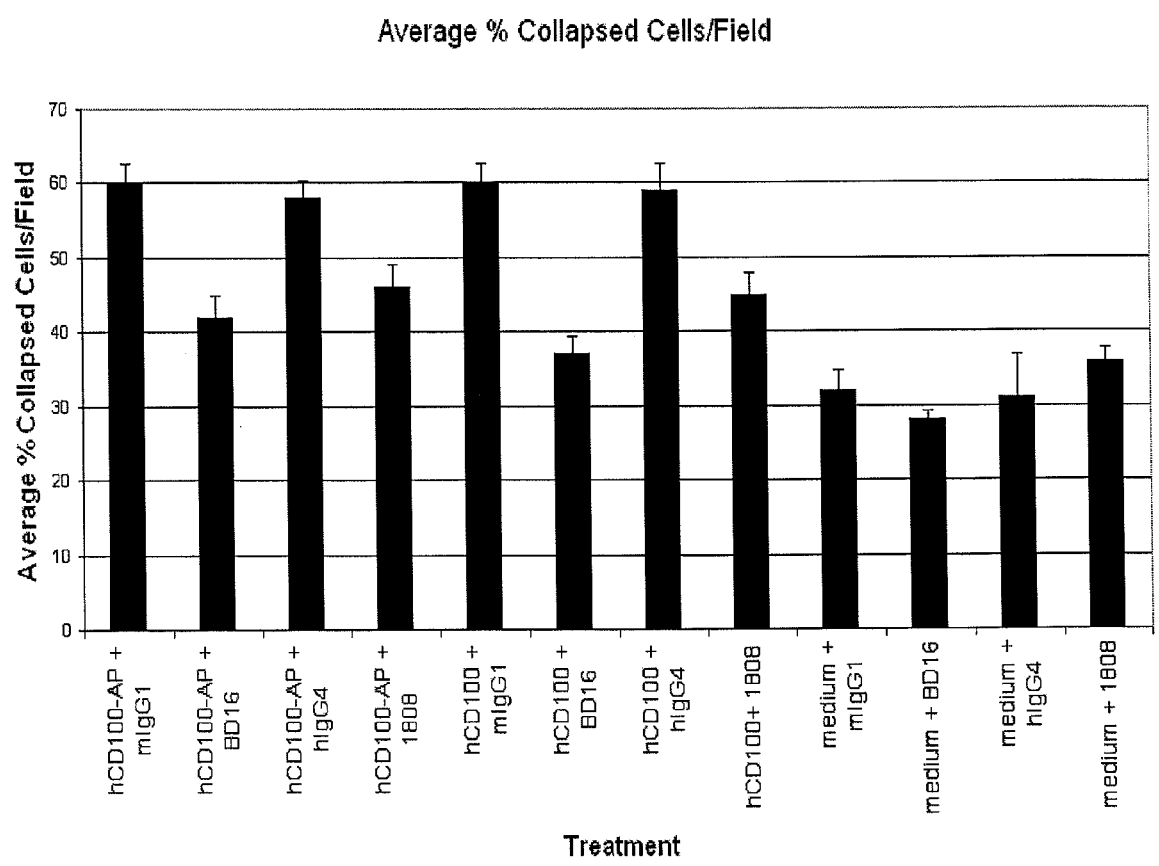

FIG. 10 demonstrates the COS cell growth cone collapse assay. COS cells were transfected with Plexin B1 and Actin-EYFP. After stimulation with or without CD100 antibodies, the number of collapsed cells (based on morphological changes) were enumerated and expressed as the number of collapsed cells per field of view.

Figure 11A:
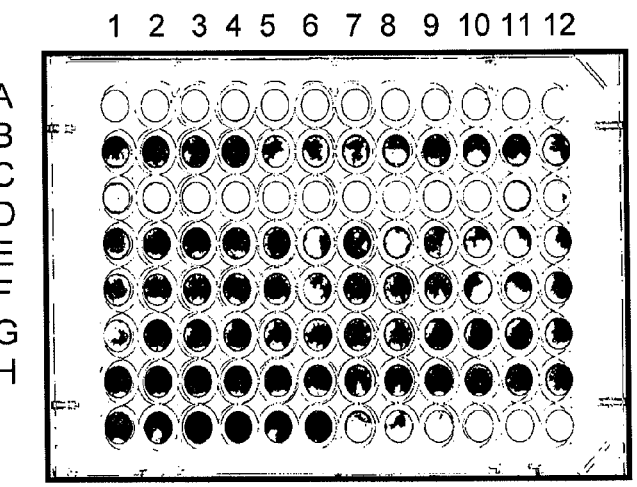
Figure 11B:
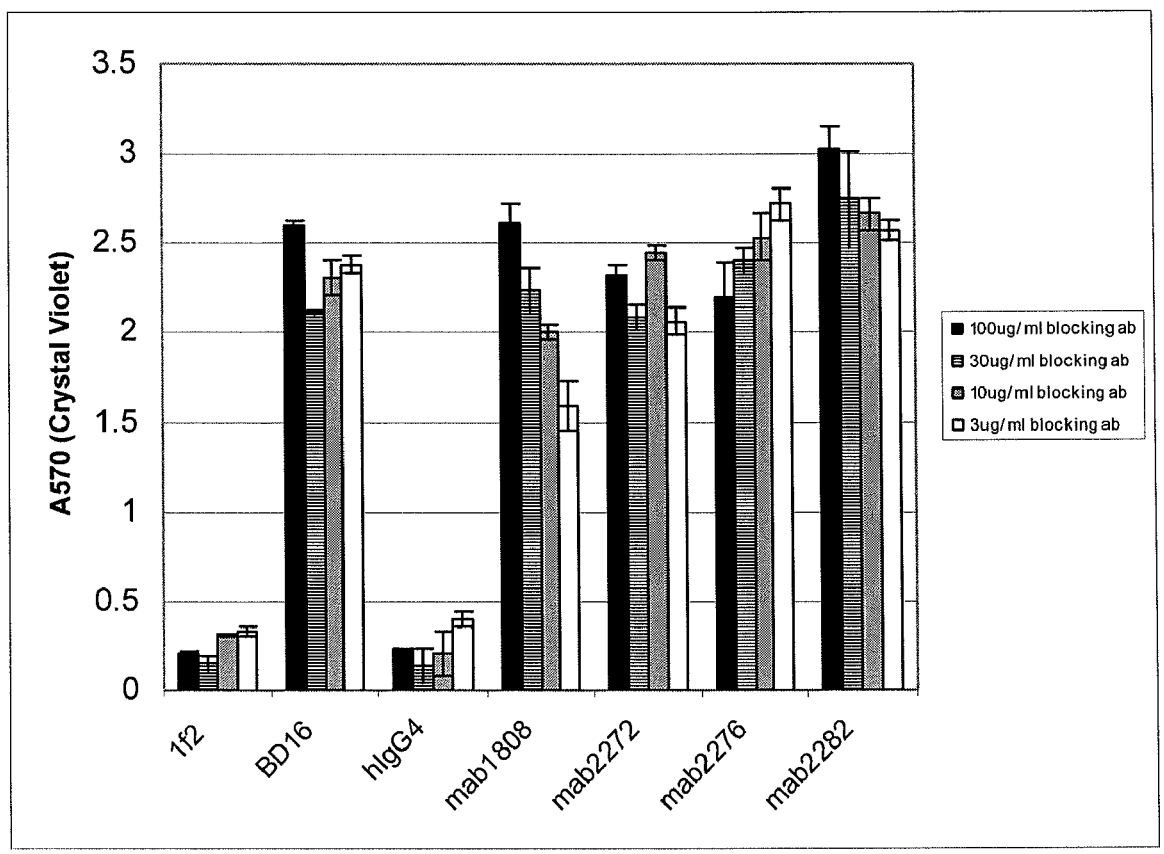

FIGS. 11A and 11B show neutralization of CD100 by Mab BD16, Mab 1808, Mab 2272, Mab 2276, and Mab 2282. Two micrograms/ml of CD100 were incubated with either 100 ug/ml (columns 1-3), 30 ug/ml (columns 4-6), 10 ug/ml (columns 7-9), or 3 ug/ml (columns 10-12) of the indicated antibody (1f2 negative control mouse IgG1 antibody, BD16, human IgG4, Mab 1808, Mab 2272, Mab 2276, or Mab 2282), and then added to each well in rows A-G. The wells in row H, columns 1-3 contained only Plexin B1+293 cells. The wells in row H, columns 4-6 contained Plexin B1+293 cells in which 2 ug/ml C35 (a control protein that does not affect integrin activity) were added. The wells in row H, columns 7-9 contained Plexin B1+293 cells in which 2 ug/ml CD100 was added. The wells in row H, columns 10-12 contained no cells.

Figure 12:
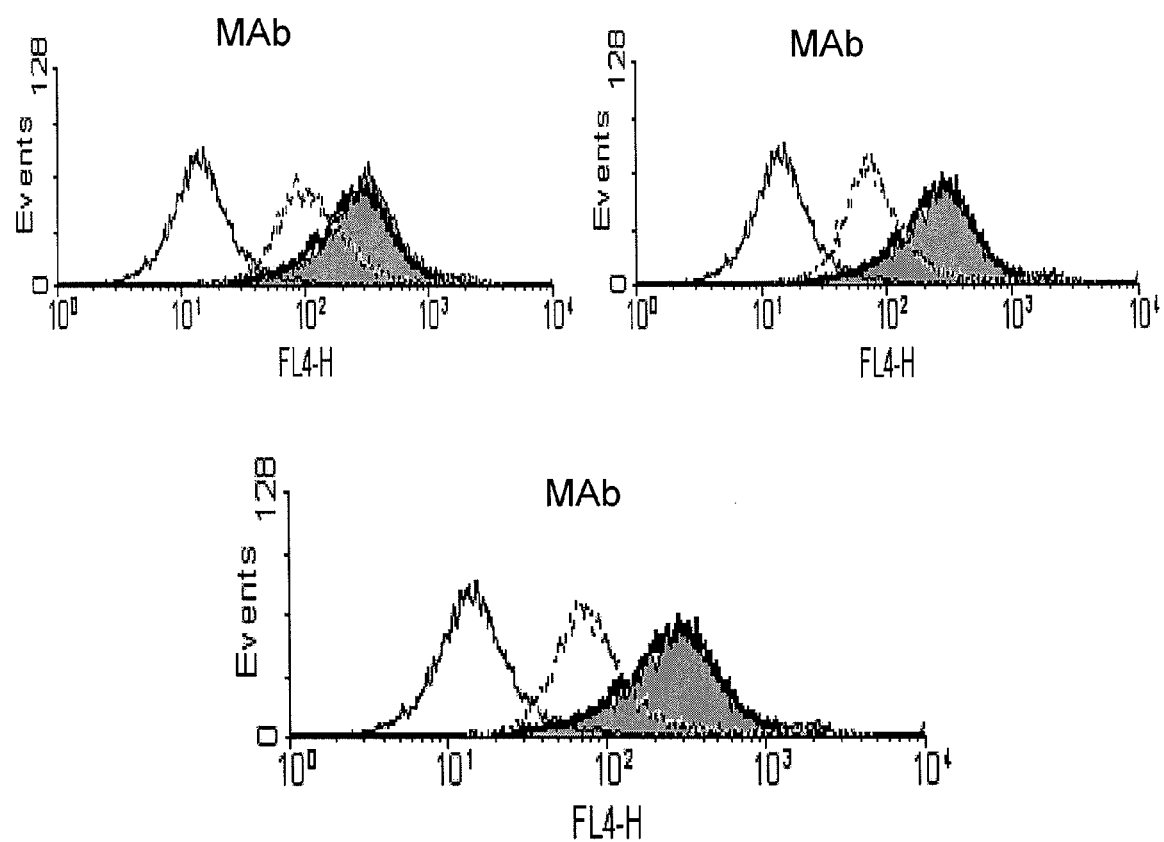

FIG. 12 demonstrates the CD100 neutralization activity of Mab 301, MAb 2276, and MAb 2282 in plexin B1+293 cells.

Figure 13:
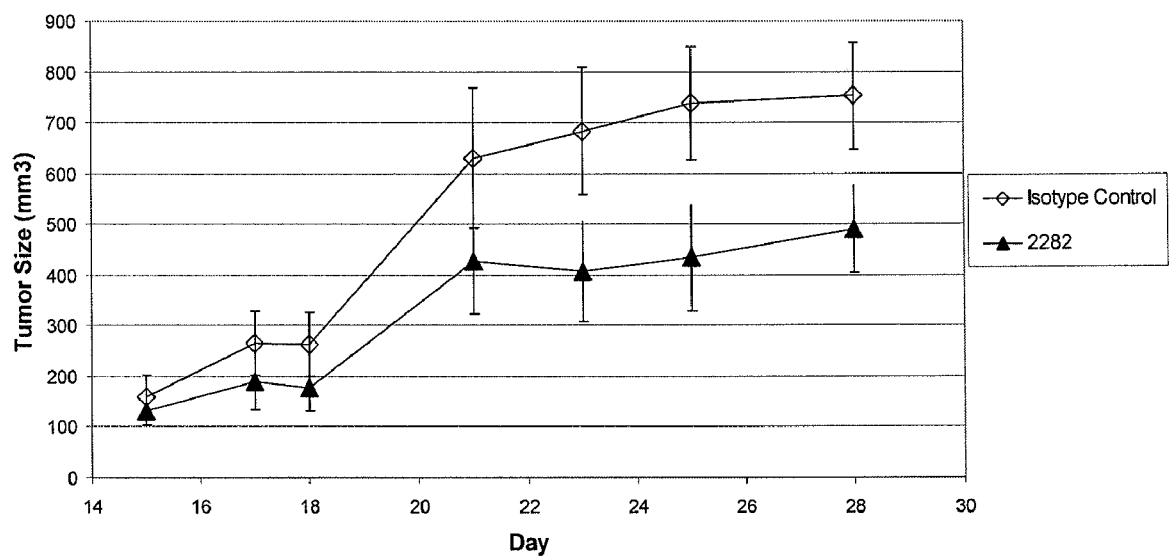

FIG. 13 demonstrates growth inhibition of the HN12 head and neck cancer cell line with MAb 2282 in a murine tumor xenograft model.

Figure 14:
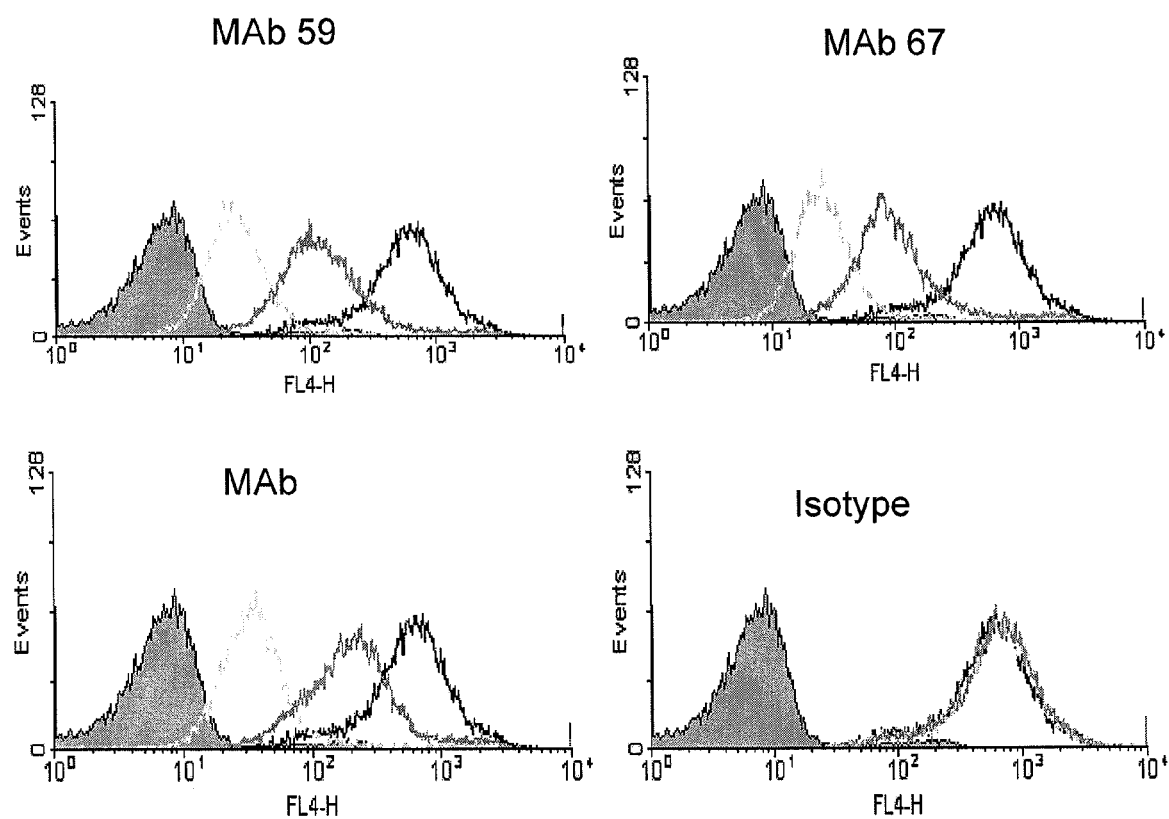

FIG. 14 demonstrates disruption of the association between CD100 and the plexin B1 receptor by murine monoclonal anti-CD100 antibodies MAb 59, MAb 67, MAb 76, and mouse IgG isotype control in plexin B1+293 cells. Grey shading represents the addition of the rabbit anti-His antibody and streptavidin-APC alone, which was used for detection of His-tagged CD100 bound to the plexin B1 receptor. The black outline with no shading represents samples with murine CD100 (400 ng/ml) that were not treated with the anti-CD100 MAbs, anti-His antibody, or streptavidin-APC. The dashed outline with no shading represents samples with murine CD100 (400 ng/ml) and 0.625 µg/ml anti-CD100 MAb and the grey outline with no shading represents samples with murine CD100 (400 ng/ml) and 0.156 µg/ml anti-CD100 MAb, followed by detection with the anti-His antibody and streptavidin-APC.

Figure 15:
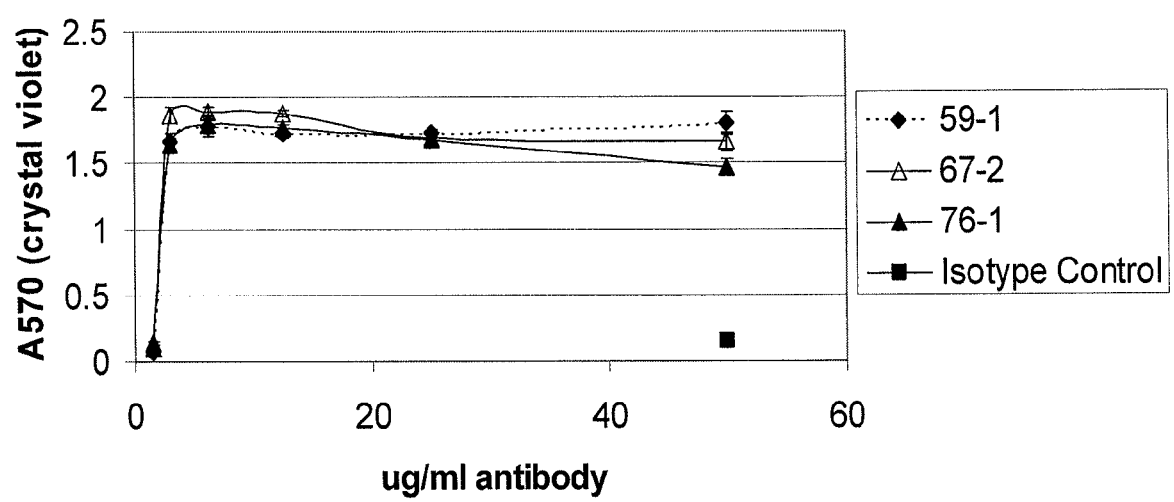

FIG. 15 demonstrates the neutralization of CD100 activity in a cell detachment assay by murine MAb 59, MAb 67, and MAb 76.

Figure 16A:
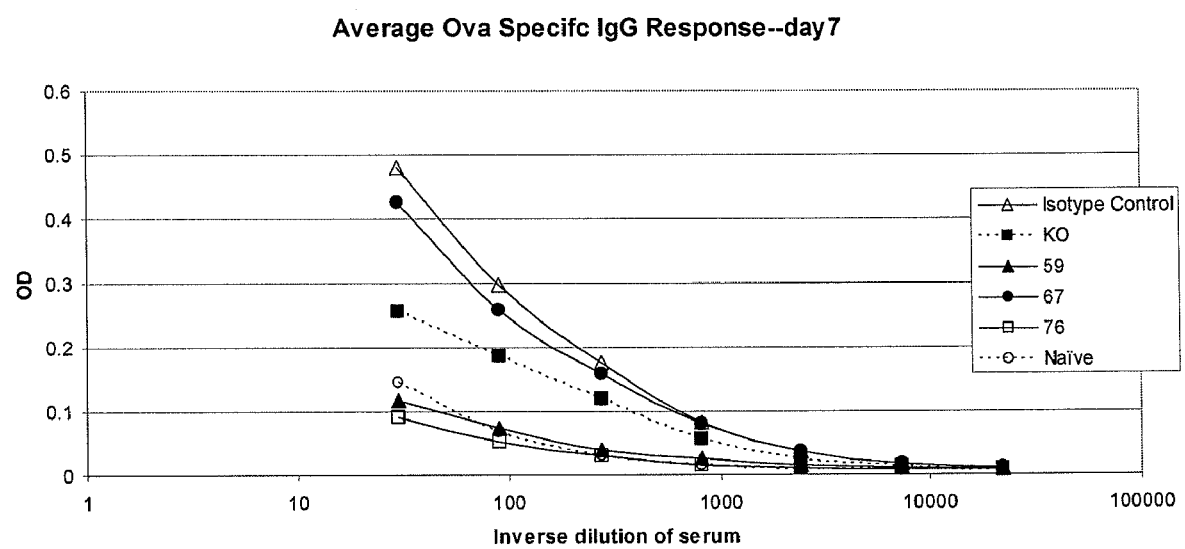
Figure 16B:
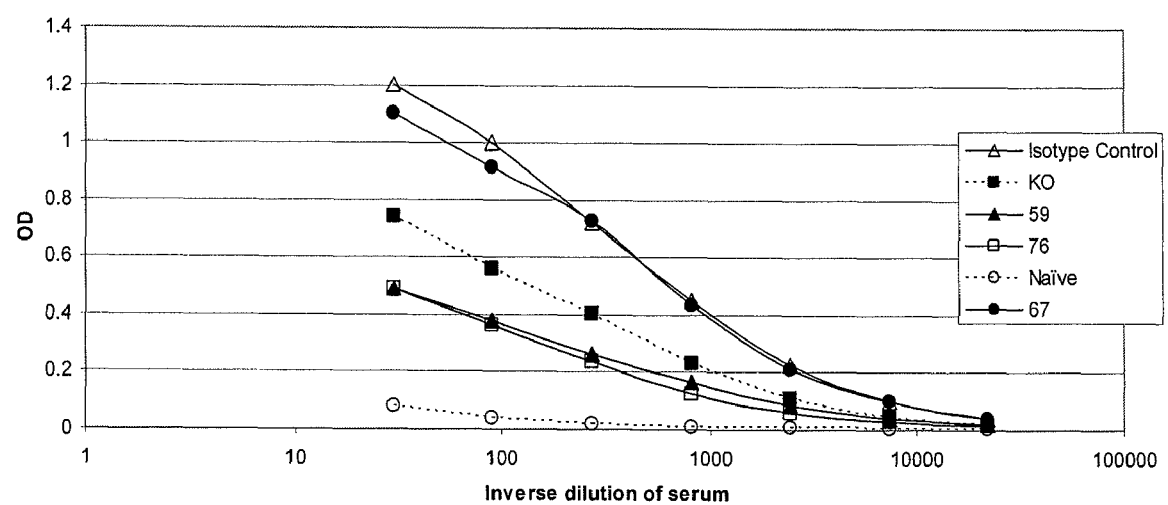

FIGS. 16A and 16B demonstrate the inhibition of in vivo B cell responses by MAb 59, MAb 67, and MAb 76. BALB/c mice were immunized with ovalbumin in CFA and were treated i.p. with the murine monoclonal anti-CD100 antibodies or an isotype control. The MAbs were again administered on days 3, 7, and 10. Serum was collected and OVA-specific serum IgG measured on day 7 (FIG. 16A) and day 12 (FIG. 16B). Results were compared to a naïve mouse that was untreated and a CD100-deficient mouse (KO).

Figure 17:
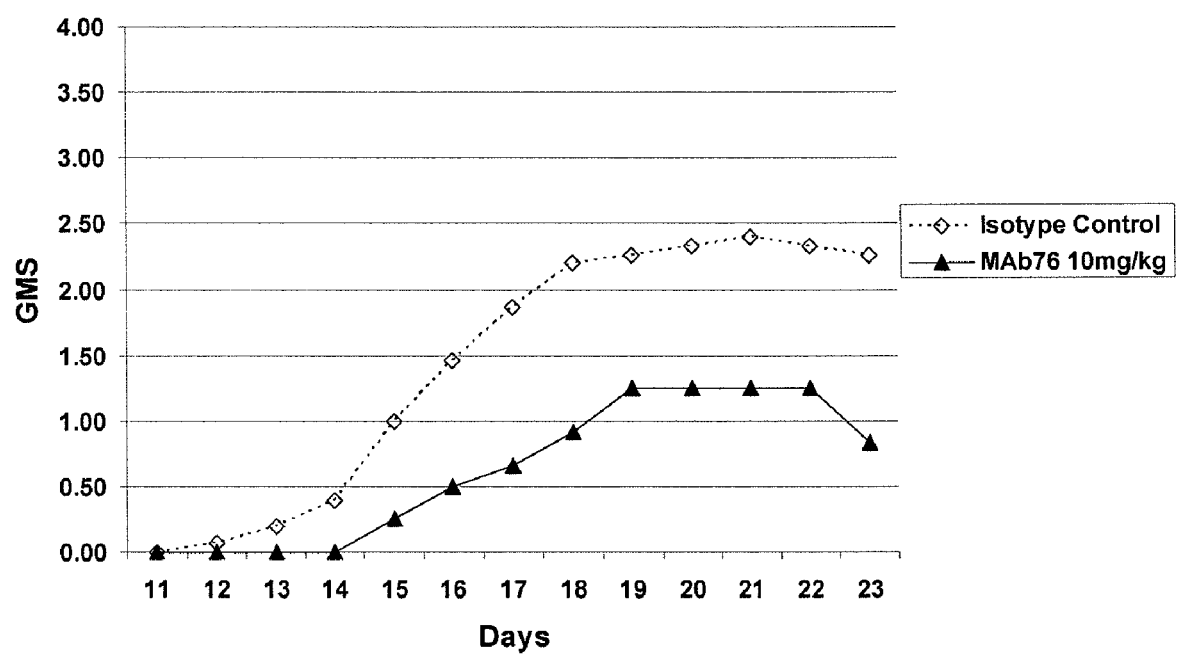

FIG. 17 depicts the reduction of clinical symptoms in the C57BL/6 EAE animal model with the murine anti-CD100 MAb 76 (10 mg/kg) relative to an isotype control antibody.

Figure 18:
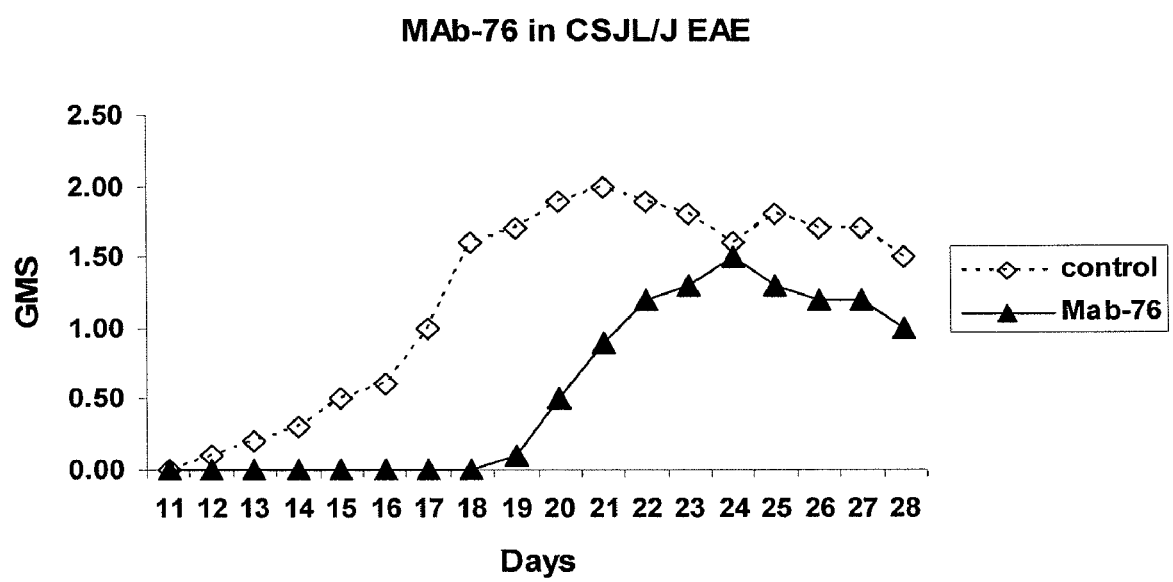

FIG. 18 shows the reduction of clinical symptoms in the CSJL EAE animal model with the murine anti-CD100 MAb 76 (10 mg/kg) relative to an isotype control antibody.

DETAILED DESCRIPTION OF THE INVENTION

I. Definitions

It is to be noted that the term "a" or "an" entity refers to one or more of that entity; for example, "an anti-CD100 antibody"

is understood to represent one or more anti-CD100 antibodies. As such, the terms "a" (or "an"), "one or more," and "at least one" can be used interchangeably herein.

As used herein, the term "tumor" refers to all neoplastic cell growth and proliferation, whether malignant or benign, and all pre-cancerous cells and tissues.

"Invasive angiogenesis" refers to the formation of blood vessels for the support of pathological conditions, including malignant and non-malignant tumors as well as the abnormal formation of new blood vessels in macular degeneration.

The terms, "cancer" and "cancerous" refer to or describe the physiological condition in mammals that is typically characterized by unregulated cell growth. Examples of cancer include but are not limited to lymphoma and leukemia.

As used herein, the term "polypeptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids, and does not refer to a specific length of the product. Thus, peptides, dipeptides, tripeptides, oligopeptides, "protein," "amino acid chain," or any other term used to refer to a chain or chains of two or more amino acids, are included within the definition of "polypeptide," and the term "polypeptide" may be used instead of, or interchangeably with any of these terms. The term "polypeptide" is also intended to refer to the products of post-expression modifications of the polypeptide, including without limitation glycosylation, acetylation, phosphorylation, amidation, derivatization by known protecting/blocking groups, proteolytic cleavage, or modification by non-naturally occurring amino acids. A polypeptide may be derived from a natural biological source or produced by recombinant technology, but is not necessarily translated from a designated nucleic acid sequence. It may be generated in any manner, including by chemical synthesis.

A polypeptide of the invention may be of a size of about 3 or more, 5 or more, 10 or more, 20 or more, 25 or more, 50 or more, 75 or more, 100 or more, 200 or more, 500 or more, 1,000 or more, or 2,000 or more amino acids. Polypeptides may have a defined three-dimensional structure, although they do not necessarily have such structure. Polypeptides with a defined three-dimensional structure are referred to as folded, and polypeptides that do not possess a defined three-dimensional structure, but rather can adopt a large number of different conformations, are referred to as unfolded. As used herein, the term glycoprotein refers to a protein coupled to at least one carbohydrate moiety that is attached to the protein via an oxygen-containing or a nitrogen-containing side chain of an amino acid residue, e.g., a serine residue or an asparagine residue.

By an "isolated" polypeptide or a fragment, variant, or derivative thereof is intended a polypeptide that is not in its natural milieu. No particular level of purification is required. For example, an isolated polypeptide can be removed from its native or natural environment. Recombinantly produced polypeptides and proteins expressed in host cells are considered isolated for purpose of the invention, as are native or recombinant polypeptides that have been separated, fractionated, or partially or substantially purified by any suitable technique.

Also included as polypeptides of the present invention are fragments, derivatives, analogs, or variants of the foregoing polypeptides, and any combination thereof. The terms "fragment," "variant," "derivative," and "analog" when referring to anti-CD100 antibodies or antibody polypeptides of the present invention include any polypeptides that retain at least some of the antigen-binding properties of the corresponding antibody or antibody polypeptide of the invention. Fragments of polypeptides of the present invention include proteolytic fragments, as well as deletion fragments, in addition to specific antibody fragments discussed elsewhere herein. Variants of anti-CD100 antibodies and antibody polypeptides of the present invention include fragments as described above, and also polypeptides with altered amino acid sequences due to amino acid substitutions, deletions, or insertions. Variants may occur naturally or be non-naturally occurring. Non-naturally occurring variants may be produced using art-known mutagenesis techniques. Variant polypeptides may comprise conservative or non-conservative amino acid substitutions, deletions, or additions. Derivatives of anti-CD100 antibodies and antibody polypeptides of the present invention, are polypeptides that have been altered so as to exhibit additional features not found on the reference antibody or antibody polypeptide of the invention. Examples include fusion proteins. Variant polypeptides may also be referred to herein as "polypeptide analogs." As used herein a "derivative" of an anti-CD100 antibody or antibody polypeptide refers to a subject polypeptide having one or more residues chemically derivatized by reaction of a functional side group. Also included as "derivatives" are those peptides that contain one or more naturally occurring amino acid derivatives of the twenty standard amino acids. For example, 4-hydroxyproline may be substituted for proline; 5-hydroxylysine may be substituted for lysine; 3-methylhistidine may be substituted for histidine; homoserine may be substituted for serine; and ornithine may be substituted for lysine.

The term "polynucleotide" is intended to encompass a singular nucleic acid as well as plural nucleic acids, and refers to an isolated nucleic acid molecule or construct, e.g., messenger RNA (mRNA) or plasmid DNA (pDNA). A polynucleotide may comprise a conventional phosphodiester bond or a non-conventional bond (e.g., an amide bond, such as found in peptide nucleic acids (PNA)). The term "nucleic acid" refers to any one or more nucleic acid segments, e.g., DNA or RNA fragments, present in a polynucleotide. By "isolated" nucleic acid or polynucleotide is intended a nucleic acid molecule, DNA or RNA, that has been removed from its native environment. For example, a recombinant polynucleotide encoding an anti-CD100 antibody contained in a vector is considered isolated for the purposes of the present invention. Further examples of an isolated polynucleotide include recombinant polynucleotides maintained in heterologous host cells or purified (partially or substantially) polynucleotides in solution. Isolated RNA molecules include in vivo or in vitro RNA transcripts of polynucleotides of the present invention. Isolated polynucleotides or nucleic acids according to the present invention further include such molecules produced synthetically. In addition, a polynucleotide or a nucleic acid may be or may include a regulatory element such as a promoter, ribosome binding site, or a transcription terminator.

As used herein, a "coding region" is a portion of nucleic acid that consists of codons translated into amino acids. Although a "stop codon" (TAG, TGA, or TAA) is not translated into an amino acid, it may be considered to be part of a coding region, but any flanking sequences, for example promoters, ribosome binding sites, transcriptional terminators, introns, and the like, are not part of a coding region. Two or more coding regions of the present invention can be present in a single polynucleotide construct, e.g., on a single vector, or in separate polynucleotide constructs, e.g., on separate (different) vectors. Furthermore, any vector may contain a single coding region, or may comprise two or more coding regions, e.g., a single vector may separately encode an immunoglobulin heavy chain variable region and an immunoglobulin light chain variable region. In addition, a vector, polynucleotide, or nucleic acid of the invention may encode heterologous coding regions, either fused or unfused to a nucleic acid encoding an anti-CD100 antibody or fragment, variant, or derivative thereof. Heterologous coding regions include without limitation specialized elements or motifs, such as a secretory signal peptide or a heterologous functional domain.

In certain embodiments, the polynucleotide or nucleic acid is DNA. In the case of DNA, a polynucleotide comprising a nucleic acid that encodes a polypeptide normally may include a promoter and/or other transcription or translation control elements operably associated with one or more coding regions. An operable association is when a coding region for a gene product, e.g., a polypeptide, is associated with one or more regulatory sequences in such a way as to place expression of the gene product under the influence or control of the regulatory sequence(s). Two DNA fragments (such as a polypeptide coding region and a promoter associated therewith) are "operably associated" if induction of promoter function results in the transcription of mRNA encoding the desired gene product and if the nature of the linkage between the two DNA fragments does not interfere with the ability of the expression regulatory sequences to direct the expression of the gene product or interfere with the ability of the DNA template to be transcribed. Thus, a promoter region would be operably associated with a nucleic acid encoding a polypeptide if the promoter was capable of effecting transcription of that nucleic acid. The promoter may be a cell-specific promoter that directs substantial transcription of the DNA only in predetermined cells. Other transcription control elements, besides a promoter, for example enhancers, operators, repressors, and transcription termination signals, can be operably associated with the polynucleotide to direct cell-specific transcription. Suitable promoters and other transcription control regions are disclosed herein.

A variety of transcription control regions are known to those skilled in the art. These include, without limitation, transcription control regions that function in vertebrate cells, such as, but not limited to, promoter and enhancer segments from cytomegaloviruses (the immediate early promoter, in conjunction with intron-A), simian virus 40 (the early promoter), and retroviruses (such as Rous sarcoma virus). Other transcription control regions include those derived from vertebrate genes such as actin, heat shock protein, bovine growth hormone and rabbit β-globin, as well as other sequences capable of controlling gene expression in eukaryotic cells. Additional suitable transcription control regions include tissue-specific promoters and enhancers as well as lymphokine-inducible promoters (e.g., promoters inducible by interferons or interleukins).

Similarly, a variety of translation control elements are known to those of ordinary skill in the art. These include, but are not limited to, ribosome binding sites, translation initiation and termination codons, and elements derived from picornaviruses (particularly an internal ribosome entry site, or IRES, also referred to as a CITE sequence).

In other embodiments, a polynucleotide of the present invention is RNA, for example, in the form of messenger RNA (mRNA).

Polynucleotide and nucleic acid coding regions of the present invention may be associated with additional coding regions that encode secretory or signal peptides, which direct the secretion of a polypeptide encoded by a polynucleotide of the present invention. According to the signal hypothesis, proteins secreted by mammalian cells have a signal peptide or secretory leader sequence that is cleaved from the mature protein once export of the growing protein chain across the rough endoplasmic reticulum has been initiated. Those of ordinary skill in the art are aware that polypeptides secreted by vertebrate cells generally have a signal peptide fused to the N-terminus of the polypeptide, which is cleaved from the complete or "full length" polypeptide to produce a secreted or "mature" form of the polypeptide. In certain embodiments, the native signal peptide, e.g., an immunoglobulin heavy chain or light chain signal peptide is used, or a functional derivative of that sequence that retains the ability to direct the secretion of the polypeptide that is operably associated with it. Alternatively, a heterologous mammalian signal peptide, or a functional derivative thereof, may be used. For example, the wild-type leader sequence may be substituted with the leader sequence of human tissue plasminogen activator (TPA) or mouse β-glucuronidase.

The present invention is directed to certain anti-CD100 antibodies, or antigen-binding fragments, variants, or derivatives thereof. Unless specifically referring to full-sized antibodies such as naturally occurring antibodies, the term "anti-CD100 antibodies" encompasses full-sized antibodies as well as antigen-binding fragments, variants, analogs, or derivatives of such antibodies, e.g., naturally occurring antibody or immunoglobulin molecules or engineered antibody molecules or fragments that bind antigen in a manner similar to antibody molecules.

The terms "antibody" and "immunoglobulin" are used interchangeably herein. An antibody or immunoglobulin comprises at least the variable domain of a heavy chain, and normally comprises at least the variable domains of a heavy chain and a light chain. Basic immunoglobulin structures in vertebrate systems are relatively well understood. See, e.g., Harlow et al. (1988) *Antibodies: A Laboratory Manual* (2nd ed.; Cold Spring Harbor Laboratory Press).

As will be discussed in more detail below, the term "immunoglobulin" comprises various broad classes of polypeptides that can be distinguished biochemically. Those skilled in the art will appreciate that heavy chains are classified as gamma, mu, alpha, delta, or epsilon, (γ, μ, α, δ, ε) with some subclasses among them (e.g., γ1-γ4). It is the nature of this chain that determines the "class" of the antibody as IgG, IgM, IgA, IgD, or IgE, respectively. The immunoglobulin subclasses (isotypes) e.g., $IgG_1$, $IgG_2$, $IgG_3$, $IgG_4$, $IgA_1$, etc., are well characterized and are known to confer functional specialization. Modified versions of each of these classes and isotypes are readily discernable to the skilled artisan in view of the instant disclosure and, accordingly, are within the scope of the instant invention. Although all immunoglobulin classes are clearly within the scope of the present invention, the following discussion will generally be directed to the IgG class of immunoglobulin molecules. With regard to IgG, a standard immunoglobulin molecule comprises two identical light chain polypeptides of molecular weight approximately 23,000 Daltons, and two identical heavy chain polypeptides of molecular weight 53,000-70,000 Daltons. The four chains are typically joined by disulfide bonds in a "Y" configuration wherein the light chains bracket the heavy chains starting at the mouth of the "Y" and continuing through the variable region.

Light chains are classified as either kappa or lambda (κ, λ). Each heavy chain class may be bound with either a kappa or lambda light chain. In general, the light and heavy chains are covalently bonded to each other, and the "tail" portions of the two heavy chains are bonded to each other by covalent disulfide linkages or non-covalent linkages when the immunoglobulins are generated either by hybridomas, B cells, or genetically engineered host cells. In the heavy chain, the amino acid sequences run from an N-terminus at the forked ends of the Y configuration to the C-terminus at the bottom of each chain.

Both the light and heavy chains are divided into regions of structural and functional homology referred to as the "constant region" and the "variable region." The terms "constant" and "variable" are used functionally. In this regard, it will be appreciated that the variable domains of both the light ($V_L$) and heavy ($V_H$) chain portions determine antigen recognition and specificity. Conversely, the constant domains of the light chain ($C_L$) and the heavy chain ($C_H1$, $C_H2$, or $C_H3$) confer important biological properties such as secretion, transplacental mobility, Fc receptor binding, complement binding, and the like. By convention the numbering of the constant region domains increases as they become more distal from the antigen binding site or amino-terminus of the antibody. The N-terminal portion is a variable region and at the C-terminal portion is a constant region; the $C_H3$ and $C_L$ domains actually comprise the carboxy-terminus of the heavy and light chain, respectively.

As indicated above, the variable region allows the antibody to selectively recognize and specifically bind epitopes on antigens. That is, the $V_L$ domain and $V_H$ domain, or subset of the complementarity determining regions (CDRs) within these variable domains, of an antibody combine to form the variable region that defines a three dimensional antigen binding site. This quaternary antibody structure forms the antigen binding site present at the end of each arm of the Y. More specifically, the antigen binding site is defined by three CDRs on each of the $V_H$ and $V_L$ chains. In some instances, e.g., certain immunoglobulin molecules derived from camelid species or engineered based on camelid immunoglobulins, a complete immunoglobulin molecule may consist of heavy chains only, with no light chains. See, e.g., Hamers-Casterman et al. (1993) Nature 363:446-448.

In naturally occurring antibodies, the six "complementarity determining regions" or "CDRs" present in each antigen binding domain are short, non-contiguous sequences of amino acids that are specifically positioned to form the antigen binding domain as the antibody assumes its three dimensional configuration in an aqueous environment. The remainder of the amino acids in the antigen binding domains, referred to as "framework" regions, show less inter-molecular variability. The framework regions largely adopt a β-sheet conformation and the CDRs form loops that connect, and in some cases form part of, the β-sheet structure. Thus, framework regions act to form a scaffold that provides for positioning the CDRs in correct orientation by inter-chain, non-covalent interactions. The antigen binding domain formed by the positioned CDRs defines a surface complementary to the epitope on the immunoreactive antigen. This complementary surface promotes the non-covalent binding of the antibody to its cognate epitope. The amino acids comprising the CDRs and the framework regions, respectively, can be readily identified for any given heavy or light chain variable domain by one of ordinary skill in the art, since they have been precisely defined (see, "Sequences of Proteins of Immunological Interest," Kabat et al. (1983) U.S. Department of Health and Human Services; and Chothia and Lesk (1987) J. Mol. Biol., 196:901-917, which are incorporated herein by reference in their entireties).

In the case where there are two or more definitions of a term that is used and/or accepted within the art, the definition of the term as used herein is intended to include all such meanings unless explicitly stated to the contrary. A specific example is the use of the term "complementarity determining region" ("CDR") to describe the non-contiguous antigen combining sites found within the variable region of both heavy and light chain polypeptides. This particular region has been described by Kabat et al. (1983) U.S. Dept. of Health and Human Services, "Sequences of Proteins of Immunological Interest" and by Chothia and Lesk (1987) J. Mol. Biol. 196:901-917, which are incorporated herein by reference, where the definitions include overlapping or subsets of amino acid residues when compared against each other. Nevertheless, application of either definition to refer to a CDR of an antibody or variants thereof is intended to be within the scope of the term as defined and used herein. The appropriate amino acid residues that encompass the CDRs as defined by each of the above cited references are set forth below in Table I as a comparison. The exact residue numbers that encompass a particular CDR will vary depending on the sequence and size of the CDR. Those skilled in the art can routinely determine which residues comprise a particular CDR given the variable region amino acid sequence of the antibody.

TABLE 1

CDR Definitions[1]

| | Kabat | Chothia |
|---|---|---|
| $V_H$ CDR1 | 31-35 | 26-32 |
| $V_H$ CDR2 | 50-65 | 52-58 |
| $V_H$ CDR3 | 95-102 | 95-102 |
| $V_L$ CDR1 | 24-34 | 26-32 |
| $V_L$ CDR2 | 50-56 | 50-52 |
| $V_L$ CDR3 | 89-97 | 91-96 |

[1]Numbering of all CDR definitions in Table 1 is according to the numbering conventions set forth by Kabat et al. (see below).

Kabat et al. also defined a numbering system for variable domain sequences that is applicable to any antibody. One of ordinary skill in the art can unambiguously assign this system of "Kabat numbering" to any variable domain sequence, without reliance on any experimental data beyond the sequence itself. As used herein, "Kabat numbering" refers to the numbering system set forth by Kabat et al. (1983) U.S. Dept. of Health and Human Services, "Sequence of Proteins of Immunological Interest." Unless otherwise specified, references to the numbering of specific amino acid residue positions in an anti-CD100 antibody or antigen-binding fragment, variant, or derivative thereof of the present invention are according to the Kabat numbering system.

In camelid species, the heavy chain variable region, referred to as $V_H H$, forms the entire antigen-binding domain. The main differences between camelid $V_H H$ variable regions and those derived from conventional antibodies ($V_H$) include (a) more hydrophobic amino acids in the light chain contact surface of $V_H$ as compared to the corresponding region in $V_H H$, (b) a longer CDR3 in $V_H H$, and (c) the frequent occurrence of a disulfide bond between CDR1 and CDR3 in $V_H H$.

Antibodies or antigen-binding fragments, variants, or derivatives thereof of the invention include, but are not limited to, polyclonal, monoclonal, multispecific, human, humanized, primatized, or chimeric antibodies, single-chain antibodies, epitope-binding fragments, e.g., Fab, Fab' and F(ab')$_2$, Fd, Fvs, single-chain Fvs (scFv), disulfide-linked Fvs (sdFv), fragments comprising either a $V_L$ or $V_H$ domain, fragments produced by a Fab expression library, and anti-idiotypic (anti-Id) antibodies (including, e.g., anti-Id antibodies to anti-CD100 antibodies disclosed herein). ScFv molecules are known in the art and are described, e.g., in U.S. Pat. No. 5,892,019. Immunoglobulin or antibody molecules of the invention can be of any type (e.g., IgG, IgE, IgM, IgD, IgA, and IgY), class (e.g., IgG1, IgG2, IgG3, IgG4, IgA1, and IgA2, etc.), or subclass of immunoglobulin molecule.

Antibody fragments, including single-chain antibodies, may comprise the variable region(s) alone or in combination with the entirety or a portion of the following: hinge region, $C_H1$, $C_H2$, and $C_H3$ domains. Also included in the invention are antigen-binding fragments also comprising any combination of variable region(s) with a hinge region, $C_H1$, $C_H2$, and $C_H3$ domains. Antibodies or immunospecific fragments thereof for use in the diagnostic and therapeutic methods disclosed herein may be derived from any animal origin including birds and mammals. Preferably, the antibodies are derived from human, murine, donkey, rabbit, goat, guinea pig, camel, llama, horse, or chicken antibodies. In another embodiment, the variable region may be condricthoid in origin (e.g., from sharks). As used herein, "human" antibodies include antibodies having the amino acid sequence of a human immunoglobulin and include antibodies isolated from human immunoglobulin libraries or from animals transgenic for one or more human immunoglobulins and that do not express endogenous immunoglobulins, as described infra and, for example in, U.S. Pat. No. 5,939,598 by Kucherlapati et al.

As used herein, the term "heavy chain portion" includes amino acid sequences derived from an immunoglobulin heavy chain. A polypeptide comprising a heavy chain portion comprises at least one of: a $C_H1$ domain, a hinge (e.g., upper, middle, and/or lower hinge region) domain, a $C_H2$ domain, a $C_H3$ domain, or a variant or fragment thereof. For example, a binding polypeptide for use in the invention may comprise a polypeptide chain comprising a $C_H1$ domain; a polypeptide chain comprising a $C_H1$ domain, at least a portion of a hinge domain, and a $C_H2$ domain; a polypeptide chain comprising a $C_H1$ domain and a $C_H3$ domain; a polypeptide chain comprising a $C_H1$ domain, at least a portion of a hinge domain, and a $C_H3$ domain, or a polypeptide chain comprising a $C_H1$ domain, at least a portion of a hinge domain, a $C_H2$ domain, and a $C_H3$ domain. In another embodiment, a polypeptide of the invention comprises a polypeptide chain comprising a $C_H3$ domain. Further, a binding polypeptide for use in the invention may lack at least a portion of a $C_H2$ domain (e.g., all or part of a $C_H2$ domain). As set forth above, it will be understood by one of ordinary skill in the art that these domains (e.g., the heavy chain portions) may be modified such that they vary in amino acid sequence from the naturally occurring immunoglobulin molecule.

In certain anti-CD100 antibodies, or antigen-binding fragments, variants, or derivatives thereof disclosed herein, the heavy chain portions of one polypeptide chain of a multimer are identical to those on a second polypeptide chain of the multimer. Alternatively, heavy chain portion-containing monomers of the invention are not identical. For example, each monomer may comprise a different target binding site, forming, for example, a bispecific antibody.

The heavy chain portions of a binding polypeptide for use in the diagnostic and treatment methods disclosed herein may be derived from different immunoglobulin molecules. For example, a heavy chain portion of a polypeptide may comprise a $C_H1$ domain derived from an IgG1 molecule and a hinge region derived from an IgG3 molecule. In another example, a heavy chain portion can comprise a hinge region derived, in part, from an IgG1 molecule and, in part, from an IgG3 molecule. In another example, a heavy chain portion can comprise a chimeric hinge derived, in part, from an IgG1 molecule and, in part, from an IgG4 molecule.

As used herein, the term "light chain portion" includes amino acid sequences derived from an immunoglobulin light chain. Preferably, the light chain portion comprises at least one of a $V_L$ or $C_L$ domain.

Anti-CD100 antibodies, or antigen-binding fragments, variants, or derivatives thereof disclosed herein may be described or specified in terms of the epitope(s) or portion(s) of an antigen, e.g., a target polypeptide (CD100) that they recognize or specifically bind. The portion of a target polypeptide that specifically interacts with the antigen binding domain of an antibody is an "epitope," or an "antigenic determinant." A target polypeptide may comprise a single epitope, but typically comprises at least two epitopes, and can include any number of epitopes, depending on the size, conformation, and type of antigen. Furthermore, it should be noted that an "epitope" on a target polypeptide may be or include non-polypeptide elements, e.g., an epitope may include a carbohydrate side chain.

The minimum size of a peptide or polypeptide epitope for an antibody is thought to be about four to five amino acids. Peptide or polypeptide epitopes preferably contain at least seven, more preferably at least nine and most preferably between at least about 15 to about 30 amino acids. Since a CDR can recognize an antigenic peptide or polypeptide in its tertiary form, the amino acids comprising an epitope need not be contiguous, and in some cases, may not even be on the same peptide chain. In the present invention, peptide or polypeptide epitope recognized by anti-CD100 antibodies of the present invention contains a sequence of at least 4, at least 5, at least 6, at least 7, more preferably at least 8, at least 9, at least 10, at least 15, at least 20, at least 25, or between about 15 to about 30 contiguous or non-contiguous amino acids of CD100.

By "specifically binds," it is generally meant that an antibody binds to an epitope via its antigen binding domain, and that the binding entails some complementarity between the antigen binding domain and the epitope. According to this definition, an antibody is said to "specifically bind" to an epitope when it binds to that epitope, via its antigen binding domain more readily than it would bind to a random, unrelated epitope. The term "specificity" is used herein to qualify the relative affinity by which a certain antibody binds to a certain epitope. For example, antibody "A" may be deemed to have a higher specificity for a given epitope than antibody "B," or antibody "A" may be said to bind to epitope "C" with a higher specificity than it has for related epitope "D."

By "preferentially binds," it is meant that the antibody specifically binds to an epitope more readily than it would bind to a related, similar, homologous, or analogous epitope. Thus, an antibody that "preferentially binds" to a given epitope would more likely bind to that epitope than to a related epitope, even though such an antibody may cross-react with the related epitope.

By way of non-limiting example, an antibody may be considered to bind a first epitope preferentially if it binds said first epitope with a dissociation constant ($K_D$) that is less than the antibody's $K_D$ for the second epitope. In another non-limiting example, an antibody may be considered to bind a first antigen preferentially if it binds the first epitope with an affinity that is at least one order of magnitude less than the antibody's $K_D$ for the second epitope. In another non-limiting example, an antibody may be considered to bind a first epitope preferentially if it binds the first epitope with an affinity that is at least two orders of magnitude less than the antibody's $K_D$ for the second epitope.

In another non-limiting example, an antibody may be considered to bind a first epitope preferentially if it binds the first epitope with an off rate (k(off)) that is less than the antibody's k(off) for the second epitope. In another non-limiting example, an antibody may be considered to bind a first epitope preferentially if it binds the first epitope with an affinity that is at least one order of magnitude less than the antibody's k(off) for the second epitope. In another non-limiting example, an antibody may be considered to bind a first epitope preferentially if it binds the first epitope with an affinity that is at least two orders of magnitude less than the antibody's k(off) for the second epitope.

An antibody or antigen-binding fragment, variant, or derivative disclosed herein may be said to bind a target polypeptide disclosed herein or a fragment or variant thereof with an off rate (k(off)) of less than or equal to $5 \times 10^{-2}$ $\sec^{-1}$, $10^{-2}$ $\sec^{-1}$, $5 \times 10^{-3}$ $\sec^{-1}$, or $10^{-3}$ $\sec^{-1}$. More preferably, an antibody of the invention may be said to bind a target polypeptide disclosed herein or a fragment or variant thereof with an off rate (k(off)) less than or equal to $5 \times 10^{-4}$ $\sec^{-1}$, $10^{-4}$ $\sec^{-1}$, $5 \times 10^{-5}$ $\sec^{-1}$, or $10^{-5}$ $\sec^{-1}$, $5 \times 10^{-6}$ $\sec^{-1}$, $10^{-6}$ $\sec^{-1}$, $5 \times 10^{-7}$ $\sec^{-1}$, or $10^{-7}$ $\sec^{-1}$.

An antibody or antigen-binding fragment, variant, or derivative thereof disclosed herein may be said to bind a target polypeptide disclosed herein or a fragment or variant thereof with an on rate (k(on)) of greater than or equal to $10^3$ $M^{-1}$ $\sec^{-1}$, $5 \times 10^3$ $M^{-1}$ $\sec^{-1}$, $10^4$ $M^{-1}$ $\sec^{-1}$, or $5 \times 10^4$ $M^{-1}$ $\sec^{-1}$. More preferably, an antibody of the invention may be said to bind a target polypeptide disclosed herein or a fragment or variant thereof with an on rate (k(on)) greater than or equal to $10^5$ $M^{-1}$ $\sec^{-1}$, $5 \times 10^5$ $M^{-1}$ $\sec^{-1}$, $10^6$ $M^{-1}$ $\sec^{-1}$, $5 \times 10^6$ $M^{-1}$ $\sec^{-1}$, or $10^7$ $M^{-1}$ $\sec^{-1}$.

An antibody is said to competitively inhibit binding of a reference antibody to a given epitope if it preferentially binds to that epitope to the extent that it blocks, to some degree, binding of the reference antibody to the epitope. Competitive inhibition may be determined by any method known in the art, for example, competition ELISA assays. An antibody may be said to competitively inhibit binding of the reference antibody to a given epitope by at least 90%, at least 80%, at least 70%, at least 60%, or at least 50%.

As used herein, the term "affinity" refers to a measure of the strength of the binding of an individual epitope with the CDR of an immunoglobulin molecule. See, e.g., Harlow et al. (1988) *Antibodies: A Laboratory Manual* (Cold Spring Harbor Laboratory Press, 2nd ed.) pages 27-28. As used herein, the term "avidity" refers to the overall stability of the complex between a population of immunoglobulins and an antigen, that is, the functional combining strength of an immunoglobulin mixture with the antigen. See, e.g., Harlow at pages 29-34. Avidity is related to both the affinity of individual immunoglobulin molecules in the population with specific epitopes, and also the valencies of the immunoglobulins and the antigen. For example, the interaction between a bivalent monoclonal antibody and an antigen with a highly repeating epitope structure, such as a polymer, would be one of high avidity.

Anti-CD100 antibodies or antigen-binding fragments, variants, or derivatives thereof of the invention may also be described or specified in terms of their cross-reactivity. As used herein, the term "cross-reactivity" refers to the ability of an antibody, specific for one antigen, to react with a second antigen; a measure of relatedness between two different antigenic substances. Thus, an antibody is cross reactive if it binds to an epitope other than the one that induced its formation. The cross reactive epitope generally contains many of the same complementary structural features as the inducing epitope, and in some cases, may actually fit better than the original.

For example, certain antibodies have some degree of cross-reactivity, in that they bind related, but non-identical epitopes, e.g., epitopes with at least 95%, at least 90%, at least 85%, at least 80%, at least 75%, at least 70%, at least 65%, at least 60%, at least 55%, and at least 50% identity (as calculated using methods known in the art and described herein) to a reference epitope. An antibody may be said to have little or no cross-reactivity if it does not bind epitopes with less than 95%, less than 90%, less than 85%, less than 80%, less than 75%, less than 70%, less than 65%, less than 60%, less than 55%, and less than 50% identity (as calculated using methods known in the art and described herein) to a reference epitope. An antibody may be deemed "highly specific" for a certain epitope, if it does not bind any other analog, ortholog, or homolog of that epitope.

Anti-CD100 antibodies or antigen-binding fragments, variants or derivatives thereof of the invention may also be described or specified in terms of their binding affinity to a polypeptide of the invention. Preferred binding affinities include those with a dissociation constant or Kd less than $5 \times 10^{-2}$ M, $10^{-2}$ M, $5 \times 10^{-3}$ M, $10^{-3}$ M, $5 \times 10^{-4}$ M, $10^{-4}$ M, $5 \times 10^{-5}$ M, $10^{-5}$ M, $5 \times 10^{-6}$ M, $10^{-6}$ M, $5 \times 10^{-7}$ M, $10^{-7}$ M, $5 \times 10^{-8}$ M, $10^{-8}$ M, $5 \times 10^{-9}$ M, $10^{-9}$ M, $5 \times 10^{-10}$ M, $10^{-10}$ M, $5 \times 10^{-11}$ M, $10^{-11}$ M, $5 \times 10^{-12}$ M, $10^{-12}$ M, $5 \times 10^{-13}$ M, $10^{-13}$ M, $5 \times 10^{-14}$ M, $10^{-14}$ M, $5 \times 10^{-15}$ M, or $10^{-15}$ M.

Anti-CD100 antibodies or antigen-binding fragments, variants or derivatives thereof of the invention may be "multispecific," e.g., bispecific, trispecific, or of greater multispecificity, meaning that it recognizes and binds to two or more different epitopes present on one or more different antigens (e.g., proteins) at the same time. Thus, whether an anti-CD100 antibody is "monospecific" or "multispecific," e.g., "bispecific," refers to the number of different epitopes with which a binding polypeptide reacts. Multispecific antibodies may be specific for different epitopes of a target polypeptide described herein or may be specific for a target polypeptide as well as for a heterologous epitope, such as a heterologous polypeptide or solid support material.

As used herein the term "valency" refers to the number of potential binding domains, e.g., antigen binding domains, present in an anti-CD100 antibody, binding polypeptide, or antibody. Each binding domain specifically binds one epitope. When an anti-CD100 antibody, binding polypeptide, or antibody comprises more than one binding domain, each binding domain may specifically bind the same epitope, for an antibody with two binding domains, termed "bivalent monospecific," or to different epitopes, for an antibody with two binding domains, termed "bivalent bispecific." An antibody may also be bispecific and bivalent for each specificity (termed "bispecific tetravalent antibodies"). In another embodiment, tetravalent minibodies or domain deleted antibodies can be made.

Bispecific bivalent antibodies, and methods of making them, are described, for instance in U.S. Pat. Nos. 5,731,168; 5,807,706; 5,821,333; and U.S. Patent Appl. Publ. Nos. 2003/020734 and 2002/0155537, the disclosures of all of which are incorporated by reference herein. Bispecific tetravalent antibodies, and methods of making them are described, for instance, in WO 02/096948 and WO 00/44788, the disclosures of both of which are incorporated by reference herein. See generally, PCT publications WO 93/17715; WO 92/08802; WO 91/00360; WO 92/05793; Tutt et al. (1991) *J. Immunol.* 147:60-69; U.S. Pat. Nos. 4,474,893; 4,714,681; 4,925,648; 5,573,920; 5,601,819; Kostelny et al. (1992) *J. Immunol.* 148: 1547-1553.

As previously indicated, the subunit structures and three dimensional configuration of the constant regions of the various immunoglobulin classes are well known. As used herein, the term "$V_H$ domain" includes the amino terminal variable domain of an immunoglobulin heavy chain and the term "$C_H1$ domain" includes the first (most amino terminal) constant region domain of an immunoglobulin heavy chain. The $C_H1$ domain is adjacent to the $V_H$ domain and is amino terminal to the hinge region of an immunoglobulin heavy chain molecule.

As used herein the term "$C_H2$ domain" includes the portion of a heavy chain molecule that extends, e.g., from about residue 244 to residue 360 of an antibody using conventional numbering schemes (residues 244 to 360, Kabat numbering system; and residues 231-340, EU numbering system; see Kabat E A et al. op. cit. The $C_H2$ domain is unique in that it is not closely paired with another domain. Rather, two N-linked branched carbohydrate chains are interposed between the two $C_H2$ domains of an intact native IgG molecule. It is also well documented that the $C_H3$ domain extends from the $C_H2$ domain to the C-terminal of the IgG molecule and comprises approximately $10^8$ residues.

As used herein, the term "hinge region" includes the portion of a heavy chain molecule that joins the $C_H1$ domain to the $C_H2$ domain. This hinge region comprises approximately 25 residues and is flexible, thus allowing the two N-terminal antigen binding regions to move independently. Hinge regions can be subdivided into three distinct domains: upper, middle, and lower hinge domains (Roux et al. (1998) *J. Immunol.* 161:4083).

As used herein the term "disulfide bond" includes the covalent bond formed between two sulfur atoms. The amino acid cysteine comprises a thiol group that can form a disulfide bond or bridge with a second thiol group. In most naturally occurring IgG molecules, the $C_H1$ and $C_L$ regions are linked by a disulfide bond and the two heavy chains are linked by two disulfide bonds at positions corresponding to 239 and 242 using the Kabat numbering system (position 226 or 229, EU numbering system).

As used herein, the term "chimeric antibody" will be held to mean any antibody wherein the immunoreactive region or site is obtained or derived from a first species and the constant region (which may be intact, partial or modified in accordance with the instant invention) is obtained from a second species. In preferred embodiments the target binding region or site will be from a non-human source (e.g., mouse or primate) and the constant region is human (for example, monoclonal antibody (MAb) 301 and MAb 1893 described herein).

As used herein, the term "engineered antibody" refers to an antibody in which the variable domain in either the heavy or light chain or both is altered by at least partial replacement of one or more CDRs from an antibody of known specificity and, if necessary, by partial framework region replacement and sequence changing. Although the CDRs may be derived from an antibody of the same class or even subclass as the antibody from which the framework regions are derived, it is envisaged that the CDRs will be derived from an antibody of different class and preferably from an antibody from a different species. An engineered antibody in which one or more "donor" CDRs from a non-human antibody of known specificity is grafted into a human heavy or light chain framework region is referred to herein as a "humanized antibody." It may not be necessary to replace all of the CDRs with the complete CDRs from the donor variable domain to transfer the antigen binding capacity of one variable domain to another. Rather, it may only be necessary to transfer those residues that are necessary to maintain the activity of the target binding site.

It is further recognized that the framework regions within the variable domain in a heavy or light chain, or both, of a humanized antibody may comprise solely residues of human origin, in which case these framework regions of the humanized antibody are referred to as "fully human framework regions" (for example, MAb 1656 and MAb 1808). Alternatively, one or more residues of the framework region(s) of the donor variable domain can be engineered within the corresponding position of the human framework region(s) of a variable domain in a heavy or light chain, or both, of a humanized antibody if necessary to maintain proper binding or to enhance binding to the CD100 antigen (for example, MAb 657 and MAb 1807). A human framework region that has been engineered in this manner would thus comprise a mixture of human and donor framework residues, and is referred to herein as a "partially human framework region." Given the explanations set forth in, e.g., U.S. Pat. Nos. 5,585,089, 5,693,761, 5,693,762, and 6,180,370, it will be well within the competence of those skilled in the art, either by carrying out routine experimentation or by trial and error testing to obtain a functional engineered or humanized antibody.

For example, humanization of an anti-CD100 antibody can be essentially performed following the method of Winter and co-workers (Jones et al. (1986) *Nature* 321:522-525; Riechmann et al. (1988) *Nature* 332:323-327; Verhoeyen et al. (1988) *Science* 239:1534-1536), by substituting rodent or mutant rodent CDRs or CDR sequences for the corresponding sequences of a human anti-CD100 antibody. See also U.S. Pat. Nos. 5,225,539; 5,585,089; 5,693,761; 5,693,762; 5,859, 205; herein incorporated by reference. The resulting humanized anti-CD100 antibody would comprise at least one rodent or mutant rodent CDR within the fully human framework regions of the variable domain of the heavy and/or light chain of the humanized antibody. In some instances, residues within the framework regions of one or more variable domains of the humanized anti-CD100 antibody are replaced by corresponding non-human (for example, rodent) residues (see, for example, U.S. Pat. Nos. 5,585,089; 5,693,761; 5,693,762; and 6,180,370), in which case the resulting humanized anti-CD100 antibody would comprise partially human framework regions within the variable domain of the heavy and/or light chain.

Furthermore, humanized antibodies may comprise residues that are not found in the recipient antibody or in the donor antibody. These modifications are made to further refine antibody performance (e.g., to obtain desired affinity). In general, the humanized antibody will comprise substantially all of at least one, and typically two, variable domains, in which all or substantially all of the CDRs correspond to those of a non-human immunoglobulin and all or substantially all of the framework regions are those of a human immunoglobulin sequence. The humanized antibody optionally also will comprise at least a portion of an immunoglobulin constant region (Fc), typically that of a human immunoglobulin. For further details see Jones et al. (1986) *Nature* 331:522-525; Riechmann et al. (1988) *Nature* 332:323-329; and Presta (1992) *Curr. Op. Struct. Biol.* 2:593-596; herein incorporated by reference. Accordingly, such "humanized" antibodies may include antibodies wherein substantially less than an intact human variable domain has been substituted by the corresponding sequence from a non-human species. In practice, humanized antibodies are typically human antibodies in which some CDR residues and possibly some framework residues are substituted by residues from analogous sites in rodent antibodies. See, for example, U.S. Pat. Nos. 5,225,539; 5,585,089; 5,693,761; 5,693,762; 5,859,205. See also U.S. Pat. No. 6,180,370, and International Publication No. WO 01/27160, where humanized antibodies and techniques for producing humanized antibodies having improved affinity for a predetermined antigen are disclosed.

As used herein the term "properly folded polypeptide" includes polypeptides (e.g., anti-CD100 antibodies) in which all of the functional domains comprising the polypeptide are distinctly active. As used herein, the term "improperly folded polypeptide" includes polypeptides in which at least one of the functional domains of the polypeptide is not active. In one embodiment, a properly folded polypeptide comprises polypeptide chains linked by at least one disulfide bond and, conversely, an improperly folded polypeptide comprises polypeptide chains not linked by at least one disulfide bond.

As used herein the term "engineered" includes manipulation of nucleic acid or polypeptide molecules by synthetic means (e.g., by recombinant techniques, in vitro peptide synthesis, by enzymatic or chemical coupling of peptides or some combination of these techniques).

As used herein, the terms "linked," "fused," or "fusion" are used interchangeably. These terms refer to the joining together of two more elements or components, by whatever means including chemical conjugation or recombinant means. An "in-frame fusion" refers to the joining of two or more polynucleotide open reading frames (ORFs) to form a continuous longer ORF, in a manner that maintains the correct translational reading frame of the original ORFs. Thus, a recombinant fusion protein is a single protein containing two or more segments that correspond to polypeptides encoded by the original ORFs (which segments are not normally so joined in nature). Although the reading frame is thus made continuous throughout the fused segments, the segments may be physically or spatially separated by, for example, in-frame linker sequence. For example, polynucleotides encoding the CDRs of an immunoglobulin variable region may be fused, in-frame, but be separated by a polynucleotide encoding at least one immunoglobulin framework region or additional CDR regions, as long as the "fused" CDRs are co-translated as part of a continuous polypeptide.

In the context of polypeptides, a "linear sequence" or a "sequence" is an order of amino acids in a polypeptide in an amino to carboxyl terminal direction in which residues that neighbor each other in the sequence are contiguous in the primary structure of the polypeptide.

The term "expression" as used herein refers to a process by which a gene produces a biochemical, for example, a polypeptide. The process includes any manifestation of the functional presence of the gene within the cell including, without limitation, gene knockdown as well as both transient expression and stable expression. It includes without limitation transcription of the gene into messenger RNA (mRNA), and the translation of such mRNA into polypeptide(s). If the final desired product is a biochemical, expression includes the creation of that biochemical and any precursors. Expression of a gene produces a "gene product." As used herein, a gene product can be either a nucleic acid, e.g., a messenger RNA produced by transcription of a gene, or a polypeptide which is translated from a transcript. Gene products described herein further include nucleic acids with post transcriptional modifications, e.g., polyadenylation, or polypeptides with post translational modifications, e.g., methylation, glycosylation, the addition of lipids, association with other protein subunits, proteolytic cleavage, and the like.

As used herein, the terms "treat" or "treatment" refer to both therapeutic treatment and prophylactic or preventative measures, wherein the object is to prevent or slow down (lessen) an undesired physiological change or disorder, such as the progression of multiple sclerosis. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

By "subject" or "individual" or "animal" or "patient" or "mammal," is meant any subject, particularly a mammalian subject, for whom diagnosis, prognosis, or therapy is desired. Mammalian subjects include humans, domestic animals, farm animals, and zoo, sports, or pet animals such as dogs, cats, guinea pigs, rabbits, rats, mice, horses, cattle, cows, and so on.

As used herein, phrases such as "a subject that would benefit from administration of an anti-CD100 antibody" and "an animal in need of treatment" includes subjects, such as mammalian subjects, that would benefit from administration of an anti-CD100 antibody used, e.g., for detection of an anti-CD100 polypeptide (e.g., for a diagnostic procedure) and/or from treatment, i.e., palliation or prevention of a disease, with an anti-CD100 antibody. As described in more detail herein, the anti-CD100 antibody can be used in unconjugated form or can be conjugated, e.g., to a drug, prodrug, or an isotope.

II. Target Polypeptide Description

The human CD100 protein is a homodimeric transmembrane protein consisting of two polypeptide chains of 150 kDa (SEQ ID NO: 50). Each polypeptide chain of CD100 consists of a signal sequence of about 13 amino acids followed by a semaphorin domain of about 512 amino acids, an immunoglobulin-like (Ig-like) domain of about 65 amino acids, a lysine-rich stretch of 104 amino acids, a hydrophobic transmembrane region of about 19 amino acids, and a cytoplasmic tail of 110 amino acids. A consensus site for tyrosine phosphorylation (corresponding to amino acid residues 808-813 of SEQ ID NO:50) in the cytoplasmic tail supports the predicted association of CD100 with a tyrosine kinase (Schlossman, et al., Eds. (1995) *Leucocyte Typing V* (Oxford University Press, Oxford).

The semaphorin domain is an extracellular domain of approximately 500 amino acids containing 14-16 cysteines found specifically in proteins belonging to the semaphorin protein family. The phylogenetically conserved semaphorins have been characterized in insect, chicken, mouse and human nervous systems (Kolodkin et al. (1992) *Neuron* 9:831; Luo et al (1993) *Cell* 75:217; Kolodkin et al. (1993) *Cell* 75:1389; Puschel et al. (1995) *Neuron* 14:941; Messersmith et al. (1995) *Neuron* 14:949; published PCT patent application number PCT/US94/10151). Proteins having a semaphorin domain have also been found in vaccinia virus, variola virus (Kolodkin et al. (1993) *Cell* 75:1389), and herpes virus (Ensser and Fleckenstein (1995) *J. Gen. Virol.* 76: 1063). However the viral semaphorins are only distantly related to the previously identified mammalian and insect semaphorins.

CD100 belongs to the semaphorin family of cell surface receptors and is also referred to as SEMA4D. CD100 is expressed abundantly on the surface of resting T cells and weakly on B cells and antigen presenting cells (APCs). Cellular activation increases the surface expression of CD100 as well as the generation of soluble CD100 (sCD100). CD100 has been shown to promote B cell activation, aggregation and survival; enhance CD40-induced proliferation and antibody production; enhance antibody response to T cell dependent antigens; increase T cell proliferation; enhance dendritic cell maturation and ability to stimulate T cells; and is directly implicated in demyelination and axonal degeneration (Shi et al. (2000) *Immunity* 13:633-642; Kumanogoh et al. (2002) *J Immunol* 169:1175-1181; and Watanabe et al. (2001) *J Immunol* 167:4321-4328).

Mice deficient in CD100 fail to develop experimental autoimmune encephalomyelitis induced by myelin oligodendrocyte glycoprotein peptide, because myelin oligodendrocyte glycoprotein-specific T cells are not generated in the absence of CD100 (Kumanogoh, 2002 supra). Soluble CD100 is also detected in the sera of MRL/lpr mice (model of systemic autoimmune diseases such as SLE), but not in normal mice. Further, the levels of sCD100 correlate with levels of auto-antibodies and increase with age (Wang et al. (2001) *Blood* 97:3498-3504). Soluble CD100 has also been shown to accumulate in the cerebral spinal fluid and sera of patients with demyelinating disease, and sCD100 induces apoptosis of human pluripotent neural precursors (Dev cells), and both inhibits process extension and induces apoptosis of rat oligodendrocytes in vitro (Giraudon et al. (2004) *J Immunol* 172 (2):1246-1255). This apoptosis is blocked by an anti-CD100 MAb.

III. Anti-CD100 Antibodies

The antibodies of the invention are optimized based on the monoclonal antibodies (mAb) BD16 and BB18, murine anti-CD100 antibodies as disclosed in International Patent Application WO 93/14125 and Herold et al. (1995) *Int. Immunol.* 7(1): 1-8, both of which are herein incorporated by reference.

The anti-CD100 antibodies of the invention comprise humanized CD100 antibodies that bind to human CD100. In some embodiments, the anti-CD100 antibodies of the invention comprise at least one optimized complementarity-determining region (CDR). By "optimized CDR" is intended that the CDR has been modified and optimized sequences selected based on the sustained or improved binding affinity and/or anti-CD100 activity that is imparted to an anti-CD100 antibody comprising the optimized CDR. "Anti-CD100 activity" or "CD100 blocking activity" can include activity which modulates one or more of the following activities associated with CD100: B cell activation, aggregation and survival; CD40-induced proliferation and antibody production; antibody response to T cell dependent antigens; T cell or other immune cell proliferation; dendritic cell maturation; demyelination and axonal degeneration; apoptosis of pluripotent neural precursors and/or oligodendrocytes; induction of endothelial cell migration; inhibition of spontaneous monocyte migration; binding to cell surface plexin B1; or any other activity association with soluble CD100 or CD100 that is expressed on the surface of CD100+ cells. Anti-CD100 activity can also be attributed to a decrease in incidence or severity of diseases associated with CD100 expression, including, but not limited to, certain types of lymphomas, autoimmune diseases, inflammatory diseases including central nervous system (CNS) and peripheral nervous system (PNS) inflammatory diseases, transplant rejections, and invasive angiogenesis.

The modifications involve replacement of amino acid residues within the CDR such that an anti-CD100 antibody retains specificity for the CD100 antigen and has improved binding affinity and/or improved anti-CD100 activity. Anti-CD100 activity of an anti-CD100 antibody of the invention is improved as compared to BD16 or BB18 in a functional assay as described herein and in International Patent Application WO 93/14125, herein incorporated by reference. The novel anti-CD100 antibodies of the invention and suitable antigen-binding fragments, variants, and derivatives thereof also exhibit anti-CD100 activity that is at least similar to that exhibited by BD16 or BB18, as measured in standard assays, for example, those described herein and in International Patent Application WO 93/14125. The optimized CDRs of the invention are utilized in $V_H$ and $V_L$ domains of the heavy and light chains, respectively, of anti-CD100 antibodies. Exemplary anti-CD100 antibodies of the invention comprise a $V_H$ domain selected from the group consisting of SEQ ID NO:1, 2, 6, and 27-54 (SEQ ID NO:1, 2, and 6 are respectively designated H1235, H1651, and H1751) and/or a $V_L$ domain selected from the group consisting of SEQ ID NO:4, 5, and 7 (respectively designated L284, L124 and L458).

The anti-CD100 antibodies of the invention comprise at least one optimized complementarity-determining region (CDR). By "optimized CDR" is intended that the CDR has been modified and optimized sequences selected based on the improved binding affinity and/or improved CDC activity that is imparted to an anti-CD100 antibody comprising the optimized CDR. The modifications involve replacement of amino acid residues within the CDR such that an anti-CD100 antibody retains specificity for the CD100 antigen and has improved or sustained binding affinity and/or anti-CD100 activity. Anti-CD100 activity of an anti-CD100 antibody of the invention is improved or sustained as compared to BD16 or BB18 in a functional assay as described above, or in International Patent Application WO 93/14125. The optimized CDRs of the invention are utilized in $V_H$ and $V_L$ domains of the heavy and light chains, respectively, of anti-human CD100 antibodies. Exemplary anti-CD100 antibodies of the invention comprise a $V_H$ domain selected from the group consisting of SEQ ID NO:1, 2, 6, and 27-54 and/or a $V_L$ domain selected from SEQ ID NO:4, 5, and 7.

In some embodiments, the anti-CD100 antibodies of the invention comprise optimized CDRs. That is, the anti-CD100 antibodies of the invention comprise at least one optimized CDR amino acid sequence selected from the group consisting of SEQ ID NO:14-26 or amino acid sequences having at least about 65%, about 70%, about 75%, about 80%, about 85%, about 90%, about 95%, about 96%, about 97%, about 98%, about 99%, or 100% sequence identity to a sequence selected from the group consisting of SEQ ID NO:14-26. That is, the optimized CDRs comprise the sequences set forth in SEQ ID NO:14-26 and the sequences of SEQ ID NO:14-26 having at least one, two, three, four, or five amino acid substitutions, depending upon the CDR involved.

Thus, in some embodiments, the anti-CD100 antibodies of the invention comprise a $V_H$ domain having at least one optimized CDR selected from the group consisting of:

a) a CDR1 comprising the amino acid sequence set forth in SEQ ID NO:14;

b) a CDR1 comprising an amino acid sequence having at least 85% sequence identity to the amino acid sequence set forth in SEQ ID NO:14, wherein said CDR1 comprises the lysine (Lys) residue at the position corresponding to residue 6 of SEQ ID NO:14, or a conservative substitution thereof;

c) a CDR2 comprising the amino acid selected from the group consisting of SEQ ID NO:15-24;

d) a CDR2 comprising an amino acid sequence having at least 85% sequence identity to the amino acid sequence set forth in SEQ ID NO:15, 16, or 17, wherein said CDR2 comprises the phenylalanine (Phe), tryptophan (Trp), or tyrosine (Tyr) residue at the position corresponding to residue 8 of SEQ ID NO:15, 16, or 17, respectively, or a conservative substitution thereof;

e) a CDR2 comprising an amino acid sequence having at least 85% sequence identity to the amino acid sequence set forth in SEQ ID NO:18, wherein said CDR2 comprises the glycine (Gly) residue at the position corresponding to residue 9 of SEQ ID NO:18, or a conservative substitution thereof;

f) a CDR2 comprising an amino acid sequence having at least 85% sequence identity to the amino acid sequence set forth in SEQ ID NO:19, 20, or 21, wherein said CDR2 comprises the phenylalanine (Phe), valine (Val), or tryptophan (Trp) residue at the position corresponding to residue 10 of SEQ ID NO:19, 20, or 21, respectively, or a conservative substitution thereof;

g) a CDR2 comprising an amino acid sequence having at least 85% sequence identity to the amino acid sequence set forth in SEQ ID NO:22, 23, or 24, wherein said CDR2 comprises the phenylalanine (Phe), proline (Pro), or valine (Val) residue at the position corresponding to residue 11 of SEQ ID NO:22, 23, or 24, respectively, or a conservative substitution thereof;

h) a CDR3 comprising the amino acid sequence set forth in SEQ ID NO:25 or 26;

i) a CDR3 comprising an amino acid sequence having at least 85% sequence identity to the amino acid sequence set forth in SEQ ID NO:25, wherein said CDR2 comprises the aspartic acid (Asp) residue at the position corresponding to residue 2 of SEQ ID NO:25, or a conservative substitution thereof; and, j) a CDR3 comprising an amino acid sequence having at least 85% sequence identity to the amino acid sequence set forth in SEQ ID NO:26, wherein said CDR2 comprises the threonine (Thr) residue at the position corresponding to residue 6 of SEQ ID NO:26, or a conservative substitution thereof.

In another embodiment, the anti-CD100 antibodies of the invention comprise a $V_H$ domain comprising at least one framework region selected from the group consisting of:

a) a FWR1 comprising the amino acid sequence set forth in SEQ ID NO:12 or 13;

b) a FWR1 comprising an amino acid sequence having at least 85% sequence identity to the amino acid sequence set forth in SEQ ID NO:12, wherein said FWR1 comprises the alanine (Ala) residue at the position corresponding to residue 6 of SEQ ID NO:12, or a conservative substitution thereof; and, c) a FWR1 comprising an amino acid sequence having at least 85% sequence identity to the amino acid sequence set forth in SEQ ID NO:13, wherein said FWR1 comprises the threonine (Thr) residue at the position corresponding to residue 23 of SEQ ID NO:13, or a conservative substitution thereof.

In other embodiments, the anti-CD100 antibodies of the invention comprise an immunoglobulin light chain comprising a variable domain selected from the group consisting of SEQ ID NO:4, 5, and 7.

In yet other embodiments, the anti-CD100 antibodies of the invention comprise a $V_H$ domain having an optimized CDR selected from the group recited in items (a) through (p) supra; and an immunoglobulin light chain comprising a variable domain selected from the group consisting of SEQ ID NO:4, 5, and 7.

In some embodiments, the anti-CD100 antibodies comprising at least one of the optimized CDRs of the invention are IgG1 kappa immunoglobulins. In such embodiments, the IgG1 kappa immunoglobulin can comprise a human IgG1 constant region within a heavy chain of the immunoglobulin and a human kappa constant region within a light chain of the immunoglobulin. In particular embodiments, the IgG1 kappa immunoglobulin comprises fully or partially human framework regions within the variable domain of the heavy chain and within the variable domain of the light chain. In other embodiments, the IgG1 kappa immunoglobulin comprises murine framework regions within the variable domain of the heavy chain and within the variable domain of the light chain.

In other embodiments, the anti-CD100 antibodies comprising at least one of the optimized CDRs of the invention are IgG4, IgG3, or IgG2 kappa immunoglobulins. In such embodiments, the IgG4, IgG3, or IgG2 kappa immunoglobulins can comprise a human IgG4, IgG3, or IgG4 constant region, respectively, within a heavy chain of the immunoglobulin and a human kappa constant region within a light chain of the immunoglobulin. In particular embodiments, the IgG4, IgG3, or IgG2 kappa immunoglobulin comprises fully or partially human framework regions within the variable domain of the heavy chain and within the variable domain of the light chain. In other embodiments, the IgG4, IgG3, or IgG2 kappa immunoglobulin comprises murine framework regions within the variable domain of the heavy chain and within the variable domain of the light chain.

In further embodiments of the invention, the anti-CD100 antibodies of the invention comprise a $V_H$ domain having an amino acid sequence selected from the group consisting of SEQ ID NO:1, 2, 6, and 27-54 and/or a $V_L$ domain having an amino acid sequence selected from SEQ ID NO:4, 5, and 7, or amino acid sequences having at least about 80%, 85%, about 90%, about 91%, about 92%, about 93%, about 94%, about 95%, about 96%, about 97%, about 98%, about 99% or 100% sequence identity to a sequence set forth in SEQ ID NO:1, 2, 6, and 27-54.

In yet other embodiments of the invention, the anti-CD100 antibodies of the invention comprise a $V_H$ domain, where the $V_H$ domain is selected from the group consisting of:

a) a $V_H$ domain comprising an amino acid sequence having at least 90% sequence identity to an amino acid sequence selected from the group consisting of SEQ ID NO:27-54;

b) a $V_H$ domain comprising an amino acid sequence having at least 85% sequence identity to the amino acid sequence set forth in SEQ ID NO:27, wherein said $V_H$ domain comprises the alanine (Ala) residue at the position corresponding to residue 6 of SEQ ID NO:27, or a conservative substitution thereof;

c) a $V_H$ domain comprising an amino acid sequence having at least 85% sequence identity to the amino acid sequence set forth in SEQ ID NO:28, wherein said $V_H$ domain comprises the threonine (Thr) residue at the position corresponding to residue 23 of SEQ ID NO:28, or a conservative substitution thereof;

d) a $V_H$ domain comprising an amino acid sequence having at least 85% sequence identity to the amino acid sequence set forth in SEQ ID NO:29, wherein said $V_H$ domain comprises the lysine (Lys) residue at the position corresponding to residue 31 of SEQ ID NO:29, or a conservative substitution thereof;

e) a $V_H$ domain comprising an amino acid sequence having at least 85% sequence identity to the amino acid sequence set forth in SEQ ID NO:30, 31, or 32, wherein said $V_H$ domain comprises the phenylalanine (Phe), tryptophan (Trp), or tyrosine (Tyr) residue at the position corresponding to residue 57 of SEQ ID NO:30, 31, or 32, respectively, or a conservative substitution thereof;

f) a $V_H$ domain comprising an amino acid sequence having at least 85% sequence identity to the amino acid sequence set forth in SEQ ID NO:33, wherein said V$_H$ domain comprises the glycine (Gly) residue at the position corresponding to residue 58 of SEQ ID NO:33, or a conservative substitution thereof;

g) a V$_H$ domain comprising an amino acid sequence having at least 85% sequence identity to the amino acid sequence set forth in SEQ ID NO:34, 35, or 36, wherein said V$_H$ domain comprises the phenylalanine (Phe), valine (Val), or tryptophan (Trp) residue at the position corresponding to residue 59 of SEQ ID NO:34, 35, or 36, respectively, or a conservative substitution thereof;

h) a V$_H$ domain comprising an amino acid sequence having at least 85% sequence identity to the amino acid sequence set forth in SEQ ID NO:37, 38, or 39, wherein said V$_H$ domain comprises the phenylalanine (Phe), proline (Pro), or valine (Val) residue at the position corresponding to residue 60 of SEQ ID NO: 37, 38, or 39, respectively, or a conservative substitution thereof;

i) a V$_H$ domain comprising an amino acid sequence having at least 85% sequence identity to the amino acid sequence set forth in SEQ ID NO:40, wherein said V$_H$ domain comprises the aspartic acid (Asp) residue at the position corresponding to residue 100 of SEQ ID NO:40, or a conservative substitution thereof;

j) a V$_H$ domain comprising an amino acid sequence having at least 85% sequence identity to the amino acid sequence set forth in SEQ ID NO:41, wherein said V$_H$ domain comprises the threonine (Thr) residue at the position corresponding to residue 104 of SEQ ID NO:41, or a conservative substitution thereof;

k) a V$_H$ domain comprising an amino acid sequence having at least 85% sequence identity to the amino acid sequence set forth in SEQ ID NO:42, wherein said V$_H$ domain comprises the alanine (Ala) residue at the position corresponding to residue 6 of SEQ ID NO:42, or a conservative substitution thereof, and the lysine (Lys) at the position corresponding to residue 31 of SEQ ID NO:42, or a conservative substitution thereof;

l) a V$_H$ domain comprising an amino acid sequence having at least 85% sequence identity to the amino acid sequence set forth in SEQ ID NO:43, wherein said V$_H$ domain comprises the threonine (Thr) residue at the position corresponding to residue 23 of SEQ ID NO:43, or a conservative substitution thereof, and the lysine (Lys) at the position corresponding to residue 31 of SEQ ID NO:43, or a conservative substitution thereof;

m) a V$_H$ domain comprising an amino acid sequence having at least 85% sequence identity to the amino acid sequence set forth in SEQ ID NO:44, wherein said V$_H$ domain comprises the alanine (Ala) residue at the position corresponding to residue 6 of SEQ ID NO:44, or a conservative substitution thereof, and the phenylalanine (Phe) at the position corresponding to residue 57 of SEQ ID NO:44, or a conservative substitution thereof;

n) a V$_H$ domain comprising an amino acid sequence having at least 85% sequence identity to the amino acid sequence set forth in SEQ ID NO:45, wherein said V$_H$ domain comprises the alanine (Ala) residue at the position corresponding to residue 6 of SEQ ID NO:45, or a conservative substitution thereof, and the tyrosine (Tyr) at the position corresponding to residue 57 of SEQ ID NO:45, or a conservative substitution thereof;

o) a V$_H$ domain comprising an amino acid sequence having at least 85% sequence identity to the amino acid sequence set forth in SEQ ID NO:46, wherein said V$_H$ domain comprises the alanine (Ala) residue at the position corresponding to residue 6 of SEQ ID NO:46, or a conservative substitution thereof, and the phenylalanine (Phe) at the position corresponding to residue 59 of SEQ ID NO:46, or a conservative substitution thereof;

p) a V$_H$ domain comprising an amino acid sequence having at least 85% sequence identity to the amino acid sequence set forth in SEQ ID NO:47, wherein said V$_H$ domain comprises the alanine (Ala) residue at the position corresponding to residue 6 of SEQ ID NO:47, or a conservative substitution thereof, and the phenylalanine (Phe) at the position corresponding to residue 60 of SEQ ID NO:47, or a conservative substitution thereof;

q) a V$_H$ domain comprising an amino acid sequence having at least 85% sequence identity to the amino acid sequence set forth in SEQ ID NO:48, wherein said V$_H$ domain comprises the alanine (Ala) residue at the position corresponding to residue 6 of SEQ ID NO:48, or a conservative substitution thereof, and the valine (Val) at the position corresponding to residue 60 of SEQ ID NO:48, or a conservative substitution thereof;

r) a V$_H$ domain comprising an amino acid sequence having at least 85% sequence identity to the amino acid sequence set forth in SEQ ID NO:49, wherein said V$_H$ domain comprises the threonine (Thr) residue at the position corresponding to residue 23 of SEQ ID NO:49, or a conservative substitution thereof, and the phenylalanine (Phe) at the position corresponding to residue 57 of SEQ ID NO:49, or a conservative substitution thereof;

s) a V$_H$ domain comprising an amino acid sequence having at least 85% sequence identity to the amino acid sequence set forth in SEQ ID NO:50, wherein said V$_H$ domain comprises the threonine (Thr) residue at the position corresponding to residue 23 of SEQ ID NO:50, or a conservative substitution thereof, and the tyrosine (Tyr) at the position corresponding to residue 57 of SEQ ID NO:50, or a conservative substitution thereof;

t) a V$_H$ domain comprising an amino acid sequence having at least 85% sequence identity to the amino acid sequence set forth in SEQ ID NO:51, wherein said V$_H$ domain comprises the threonine (Thr) residue at the position corresponding to residue 23 of SEQ ID NO:51, or a conservative substitution thereof, and the phenylalanine (Phe) at the position corresponding to residue 59 of SEQ ID NO:51, or a conservative substitution thereof;

u) a V$_H$ domain comprising an amino acid sequence having at least 85% sequence identity to the amino acid sequence set forth in SEQ ID NO:52, wherein said V$_H$ domain comprises the threonine (Thr) residue at the position corresponding to residue 23 of SEQ ID NO:52, or a conservative substitution thereof, and the phenylalanine (Phe) at the position corresponding to residue 60 of SEQ ID NO:52, or a conservative substitution thereof;

v) a V$_H$ domain comprising an amino acid sequence having at least 85% sequence identity to the amino acid sequence set forth in SEQ ID NO:53, wherein said V$_H$ domain comprises the threonine (Thr) residue at the position corresponding to residue 23 of SEQ ID NO:53, or a conservative substitution thereof, and the valine at the position corresponding to residue 60 of SEQ ID NO:53, or a conservative substitution thereof; and, w) a V$_H$ domain comprising an amino acid sequence having at least 85% sequence identity to the amino acid sequence set forth in SEQ ID NO:54, wherein said V$_H$ domain comprises the threonine (Thr) residue at the position corresponding to residue 23 of SEQ ID NO:54, or a conservative substitution thereof, and the tyrosine at the position corresponding to residue 104 of SEQ ID NO:54, or a conservative substitution thereof.

Anti-CD100 antibody sequences are known in the art. See, for example, International Patent Application WO 93/14125 and Herold et al. (1995) *Int. Immunol.* 7(1): 1-8, each of which is herein incorporated by reference. It is recognized that the modifications described here can be made to any of the anti-CD100 antibodies known in the art or combinations thereof. Thus murine anti-CD100 antibodies, chimeric anti-CD100 antibodies, and humanized anti-CD100 antibodies comprising at least one of the framework regions described herein are contemplated by the present invention. Anti-CD100 antibodies engineered with these modifications and combinations can be tested for the enhanced activity by assays known in the art and described herein. Methods for measuring anti-CD100 antibody binding specificity include, but are not limited to, standard competitive binding assays, assays for monitoring immunoglobulin secretion by T cells or B cells, T cell proliferation assays, apoptosis assays, ELISA assays, and the like. See, for example, such assays disclosed in WO 93/14125; Shi et al. (2000) *Immunity* 13:633-642; Kumanogoh et al. (2002) *J Immunol* 169:1175-1181; Watanabe et al. (2001) *J Immunol* 167:4321-4328; Wang et al. (2001) *Blood* 97:3498-3504; and Giraudon et al. (2004) *J Immunol* 172(2):1246-1255, all of which are herein incorporated by reference.

Suitable biologically active variants of the anti-CD100 antibodies can be used in the methods of the present invention. Such variants will retain the desired binding properties of the parent anti-CD100 antibody. Methods for making antibody variants are generally available in the art.

For example, amino acid sequence variants of an anti-CD100 antibody, an antibody region, for example the CDRs (SEQ ID NO:14-26), or an antibody variable domain of a heavy or light chain, for example the $V_H$ domain set forth in any one of SEQ ID NO:27-54 or the $V_L$ domain set forth in SEQ ID NO:4, 5, or 7, described herein, can be prepared by mutations in the cloned DNA sequence encoding the amino acid sequence of interest. Methods for mutagenesis and nucleotide sequence alterations are well known in the art. See, for example, Walker and Gaastra, eds. (1983) *Techniques in Molecular Biology* (MacMillan Publishing Company, New York); Kunkel (1985) *Proc. Natl. Acad. Sci. USA* 82:488-492; Kunkel et al. (1987) *Methods Enzymol.* 154:367-382; Sambrook et al. (1989) *Molecular Cloning: A Laboratory Manual* (Cold Spring Harbor, N.Y.); U.S. Pat. No. 4,873,192; and the references cited therein; herein incorporated by reference. Guidance as to appropriate amino acid substitutions that do not affect biological activity of the polypeptide of interest may be found in the model of Dayhoff et al. (1978) in *Atlas of Protein Sequence and Structure* (Natl. Biomed. Res. Found., Washington, D.C.), pp. 345-352, herein incorporated by reference in its entirety. The model of Dayhoff et al. uses the Point Accepted Mutation (PAM) amino acid similarity matrix (PAM 250 matrix) to determine suitable conservative amino acid substitutions. Conservative substitutions, such as exchanging one amino acid with another having similar properties, may be preferred. Examples of conservative amino acid substitutions as taught by the PAM 250 matrix of the Dayhoff et al. model include, but are not limited to, Gly⇔Ala, Val⇔Ile⇔Leu, Asp⇔Glu, Lys⇔Arg, Asn⇔Gln, and Phe⇔Trp⇔Tyr.

In constructing variants of the anti-CD100 antibody polypeptides of interest, modifications are made such that variants continue to possess the desired properties, i.e., being capable of specifically binding to a human CD100 antigen expressed on the surface of or secreted by a human cell, and having CD100 blocking activity, as described herein. Obviously, any mutations made in the DNA encoding the variant polypeptide must not place the sequence out of reading frame and preferably will not create complementary regions that could produce secondary mRNA structure. See EP Patent Application Publication No. 75,444.

In addition, the constant region of an anti-CD100 antibody can be mutated to alter effector function in a number of ways. For example, see U.S. Pat. No. 6,737,056B1 and U.S. Patent Application Publication No. 2004/0132101A1, which disclose Fc mutations that optimize antibody binding to Fc receptors.

Preferably, variants of a reference anti-CD100 antibody have amino acid sequences that have at least about 80%, about 85%, about 88%, about 90%, about 91%, about 92%, about 93%, about 94%, or about 95% sequence identity to the amino acid sequence for the reference anti-CD100 antibody molecule or to a shorter portion of the reference antibody molecule. More preferably, the molecules share at least about 96%, about 97%, about 98%, or about 99% sequence identity. When discussed herein, whether any particular polypeptide, including the constant regions, CDRs, $V_H$ domains, and $V_L$ domains disclosed herein, is at least about 65%, about 70%, about 75%, about 80%, about 85%, about 90%, about 91%, about 92%, about 93%, about 94%, about 95%, about 96%, about 97%, about 98%, about 99%, or even about 100% identical to another polypeptide can be determined using methods and computer programs/software known in the art such as, but not limited to, the BESTFIT program (Wisconsin Sequence Analysis Package, Version 8 for Unix, Genetics Computer Group, University Research Park, 575 Science Drive, Madison, Wis. 53711). BESTFIT uses the local homology algorithm of Smith and Waterman (1981) *Adv. Appl. Math.* 2:482-489, to find the best segment of homology between two sequences. When using BESTFIT or any other sequence alignment program to determine whether a particular sequence is, for example, 95% identical to a reference sequence according to the present invention, the parameters are set, of course, such that the percentage of identity is calculated over the full length of the reference polypeptide sequence and that gaps in homology of up to 5% of the total number of amino acids in the reference sequence are allowed.

For purposes of the present invention, percent sequence identity is determined using the Smith-Waterman homology search algorithm using an affine gap search with a gap open penalty of 12 and a gap extension penalty of 2, BLOSUM matrix of 62. The Smith-Waterman homology search algorithm is taught in Smith and Waterman (1981) *Adv. Appl. Math.* 2:482-489. A variant may, for example, differ from the reference anti-CD100 antibody by as few as 1 to 15 amino acid residues, as few as 1 to 10 amino acid residues, such as 6-10, as few as 5, as few as 4, 3, 2, or even 1 amino acid residue.

With respect to optimal alignment of two amino acid sequences, the contiguous segment of the variant amino acid sequence may have additional amino acid residues or deleted amino acid residues with respect to the reference amino acid sequence. The contiguous segment used for comparison to the reference amino acid sequence will include at least 20 contiguous amino acid residues, and may be 30, 40, 50, or more amino acid residues. Corrections for sequence identity associated with conservative residue substitutions or gaps can be made (see Smith-Waterman homology search algorithm).

When any two polypeptide sequences are optimally aligned for comparison, it is recognized that residues appearing opposite of one another within the alignment occupy positions within their respective polypeptides that correspond to one another. Such positions are referred to herein as "corresponding positions" and the residues residing at corresponding positions are referred to as "corresponding residues" or residues that "correspond" to one another. Thus, for example, where a polypeptide of interest is optimally aligned to a reference polypeptide sequence having, for example, 10 residues, the residue within the polypeptide of interest appearing opposite residue 5 of the reference sequence is referred to as the "residue at the position corresponding to residue 5" of the reference sequence.

The precise chemical structure of a polypeptide capable of specifically binding CD100 and retaining the desired CD100 blocking activity depends on a number of factors. As ionizable amino and carboxyl groups are present in the molecule, a particular polypeptide may be obtained as an acidic or basic salt, or in neutral form. All such preparations that retain their biological activity when placed in suitable environmental conditions are included in the definition of anti-CD100 antibodies as used herein. Further, the primary amino acid sequence of the polypeptide may be augmented by derivatization using sugar moieties (glycosylation) or by other supplementary molecules such as lipids, phosphate, acetyl groups and the like. It may also be augmented by conjugation with saccharides. Certain aspects of such augmentation are accomplished through post-translational processing systems of the producing host; other such modifications may be introduced in vitro. In any event, such modifications are included in the definition of an anti-CD100 antibody used herein so long as the desired properties of the anti-CD100 antibody are not destroyed. It is expected that such modifications may quantitatively or qualitatively affect the activity, either by enhancing or diminishing the activity of the polypeptide, in the various assays. Further, individual amino acid residues in the chain may be modified by oxidation, reduction, or other derivatization, and the polypeptide may be cleaved to obtain fragments that retain activity. Such alterations that do not destroy the desired properties (i.e., binding specificity for CD100 and CD100 blocking activity) do not remove the polypeptide sequence from the definition of anti-CD100 antibodies of interest as used herein.

The art provides substantial guidance regarding the preparation and use of polypeptide variants. In preparing the anti-CD100 antibody variants, one of skill in the art can readily determine which modifications to the native protein nucleotide or amino acid sequence will result in a variant that is suitable for use as a therapeutically active component of a pharmaceutical composition used in the methods of the present invention.

In certain anti-CD100 antibodies, the Fc portion may be mutated to decrease effector function using techniques known in the art. For example, the deletion or inactivation (through point mutations or other means) of a constant region domain may reduce Fc receptor binding of the circulating modified antibody thereby increasing tumor localization. In other cases it may be that constant region modifications consistent with the instant invention moderate complement binding and thus reduce the serum half life and nonspecific association of a conjugated cytotoxin. Yet other modifications of the constant region may be used to modify disulfide linkages or oligosaccharide moieties that allow for enhanced localization due to increased antigen specificity or antibody flexibility. The resulting physiological profile, bioavailability and other biochemical effects of the modifications, such as tumor localization, biodistribution and serum half-life, may easily be measured and quantified using well known immunological techniques without undue experimentation.

Anti-CD100 antibodies of the invention also include derivatives that are modified, e.g., by the covalent attachment of any type of molecule to the antibody such that covalent attachment does not prevent the antibody from specifically binding to its cognate epitope. For example, but not by way of limitation, the antibody derivatives include antibodies that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, etc. Additionally, the derivative may contain one or more non-classical amino acids.

A "conservative amino acid substitution" is one in which the amino acid residue is replaced with an amino acid residue having a side chain with a similar charge. Families of amino acid residues having side chains with similar charges have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity (e.g., the ability to bind an anti-CD100 polypeptide).

For example, it is possible to introduce mutations only in framework regions or only in CDR regions of an antibody molecule. Introduced mutations may be silent or neutral missense mutations, i.e., have no, or little, effect on an antibody's ability to bind antigen. These types of mutations may be useful to optimize codon usage, or improve a hybridoma's antibody production. Alternatively, non-neutral missense mutations may alter an antibody's ability to bind antigen. The location of most silent and neutral missense mutations is likely to be in the framework regions, while the location of most non-neutral missense mutations is likely to be in CDR, though this is not an absolute requirement. One of skill in the art would be able to design and test mutant molecules with desired properties such as no alteration in antigen binding activity or alteration in binding activity (e.g., improvements in antigen binding activity or change in antibody specificity). Following mutagenesis, the encoded protein may routinely be expressed and the functional and/or biological activity of the encoded protein, (e.g., ability to immunospecifically bind at least one epitope of a CD100 polypeptide) can be determined using techniques described herein or by routinely modifying techniques known in the art.

IV. Polynucleotides Encoding Anti-CD100 Antibodies

The present invention also provides for nucleic acid molecules encoding anti-CD100 antibodies of the invention, or antigen-binding fragments, variants, or derivatives thereof.

In one embodiment, the present invention provides an isolated polynucleotide comprising, consisting essentially of, or consisting of a nucleic acid encoding an immunoglobulin heavy chain variable domain ($V_H$ domain), where at least one of the CDRs of the $V_H$ domain has an amino acid sequence that is at least about 80%, about 85%, about 90%, about 95%, about 96%, about 97%, about 98%, about 99%, or identical to any one of SEQ ID NO:14-26.

In other embodiments, the present invention provides an isolated polynucleotide comprising, consisting essentially of, or consisting of a nucleic acid encoding an immunoglobulin $V_H$ domain, where at least one of the CDRs of the $V_H$ domain is selected from the group consisting of: a) a CDR1 comprising the amino acid sequence set forth in SEQ ID NO:14;

b) a CDR1 comprising an amino acid sequence having at least 85% sequence identity to the amino acid sequence set forth in SEQ ID NO:14, wherein said CDR1 comprises the lysine (Lys) residue at the position corresponding to residue 6 of SEQ ID NO:14, or a conservative substitution thereof;

c) a CDR2 comprising the amino acid selected from the group consisting of SEQ ID NO:15-25;

d) a CDR2 comprising an amino acid sequence having at least 85% sequence identity to the amino acid sequence set forth in SEQ ID NO:15, 16, or 17, wherein said CDR2 comprises the phenylalanine (Phe), tryptophan (Trp), or tyrosine (Tyr) residue at the position corresponding to residue 8 of SEQ ID NO:15, 16, or 17, respectively, or a conservative substitution thereof;

e) a CDR2 comprising an amino acid sequence having at least 85% sequence identity to the amino acid sequence set forth in SEQ ID NO:18, wherein said CDR2 comprises the glycine (Gly) residue at the position corresponding to residue 9 of SEQ ID NO:18, or a conservative substitution thereof;

f) a CDR2 comprising an amino acid sequence having at least 85% sequence identity to the amino acid sequence set forth in SEQ ID NO:19, 20, or 21, wherein said CDR2 comprises the phenylalanine (Phe), valine (Val), or tryptophan (Trp) residue at the position corresponding to residue 10 of SEQ ID NO:19, 20, or 21, respectively, or a conservative substitution thereof;

g) a CDR2 comprising an amino acid sequence having at least 85% sequence identity to the amino acid sequence set forth in SEQ ID NO:22, 23, or 24, wherein said CDR2 comprises the phenylalanine (Phe), proline (Pro), or valine (Val) residue at the position corresponding to residue 11 of SEQ ID NO:22, 23, or 24, respectively, or a conservative substitution thereof;

h) a CDR3 comprising the amino acid sequence set forth in SEQ ID NO:25 or 26;

i) a CDR3 comprising an amino acid sequence having at least 85% sequence identity to the amino acid sequence set forth in SEQ ID NO:25, wherein said CDR2 comprises the aspartic acid (Asp) residue at the position corresponding to residue 2 of SEQ ID NO:25, or a conservative substitution thereof; and, j) a CDR3 comprising an amino acid sequence having at least 85% sequence identity to the amino acid sequence set forth in SEQ ID NO:26, wherein said CDR2 comprises the threonine (Thr) residue at the position corresponding to residue 6 of SEQ ID NO:26, or a conservative substitution thereof.

In another embodiment, the present invention provides an isolated polynucleotide comprising, consisting essentially of, or consisting of a nucleic acid encoding a $V_H$ domain comprising at least one framework region selected from the group consisting of:

a) a FWR1 comprising the amino acid sequence set forth in SEQ ID NO:12 or 13;

b) a FWR1 comprising an amino acid sequence having at least 85% sequence identity to the amino acid sequence set forth in SEQ ID NO:12, wherein said FWR1 comprises the alanine (Ala) residue at the position corresponding to residue 6 of SEQ ID NO:12, or a conservative substitution thereof; and, c) a FWR1 comprising an amino acid sequence having at least 85% sequence identity to the amino acid sequence set forth in SEQ ID NO:13, wherein said FWR1 comprises the threonine (Thr) residue at the position corresponding to residue 23 of SEQ ID NO:13, or a conservative substitution thereof.

In a further embodiment, the present invention includes an isolated polynucleotide comprising, consisting essentially of, or consisting of a nucleic acid encoding a $V_H$ domain that has an amino acid sequence that is at least about 80%, about 85%, about 90%, about 91%, about 92%, about 93%, about 94%, about 95%, about 96%, about 97%, about 98%, about 99%, or 100% identical to a reference $V_H$ domain polypeptide sequence selected from the group consisting of SEQ ID NO:1, 2, 6, and 27-54, wherein an anti-CD100 antibody comprising the encoded $V_H$ domain specifically or preferentially binds to CD100.

In yet other embodiments, the present invention includes an isolated polynucleotide comprising, consisting essentially of, or consisting of a nucleic acid encoding a $V_H$ domain selected from the group consisting of: a) a $V_H$ domain comprising an amino acid sequence having at least 90% sequence identity to an amino acid sequence selected from the group consisting of SEQ ID NO:27-54;

b) a $V_H$ domain comprising an amino acid sequence having at least 85% sequence identity to the amino acid sequence set forth in SEQ ID NO:27, wherein said $V_H$ domain comprises the alanine (Ala) residue at the position corresponding to residue 6 of SEQ ID NO:27, or a conservative substitution thereof;

c) a $V_H$ domain comprising an amino acid sequence having at least 85% sequence identity to the amino acid sequence set forth in SEQ ID NO:28, wherein said $V_H$ domain comprises the threonine (Thr) residue at the position corresponding to residue 23 of SEQ ID NO:28, or a conservative substitution thereof;

d) a $V_H$ domain comprising an amino acid sequence having at least 85% sequence identity to the amino acid sequence set forth in SEQ ID NO:29, wherein said $V_H$ domain comprises the lysine (Lys) residue at the position corresponding to residue 31 of SEQ ID NO:29, or a conservative substitution thereof;

e) a $V_H$ domain comprising an amino acid sequence having at least 85% sequence identity to the amino acid sequence set forth in SEQ ID NO:30, 31, or 32, wherein said $V_H$ domain comprises the phenylalanine (Phe), tryptophan (Trp), or tyrosine (Tyr) residue at the position corresponding to residue 57 of SEQ ID NO:30, 31, or 32, respectively, or a conservative substitution thereof;

f) a $V_H$ domain comprising an amino acid sequence having at least 85% sequence identity to the amino acid sequence set forth in SEQ ID NO:33, wherein said $V_H$ domain comprises the glycine (Gly) residue at the position corresponding to residue 58 of SEQ ID NO:33, or a conservative substitution thereof;

g) a $V_H$ domain comprising an amino acid sequence having at least 85% sequence identity to the amino acid sequence set forth in SEQ ID NO:34, 35, or 36, wherein said $V_H$ domain comprises the phenylalanine (Phe), valine (Val), or tryptophan (Trp) residue at the position corresponding to residue 59 of SEQ ID NO:34, 35, or 36, respectively, or a conservative substitution thereof;

h) a $V_H$ domain comprising an amino acid sequence having at least 85% sequence identity to the amino acid sequence set forth in SEQ ID NO:37, 38, or 39, wherein said $V_H$ domain comprises the phenylalanine (Phe), proline (Pro), or valine (Val) residue at the position corresponding to residue 60 of SEQ ID NO: 37, 38, or 39, respectively, or a conservative substitution thereof;

i) a $V_H$ domain comprising an amino acid sequence having at least 85% sequence identity to the amino acid sequence set forth in SEQ ID NO:40, wherein said $V_H$ domain comprises the aspartic acid (Asp) residue at the position corresponding to residue 100 of SEQ ID NO:40, or a conservative substitution thereof;

j) a $V_H$ domain comprising an amino acid sequence having at least 85% sequence identity to the amino acid sequence set forth in SEQ ID NO:41, wherein said $V_H$ domain comprises the threonine (Thr) residue at the position corresponding to residue 104 of SEQ ID NO:41, or a conservative substitution thereof;

k) a $V_H$ domain comprising an amino acid sequence having at least 85% sequence identity to the amino acid sequence set forth in SEQ ID NO:42, wherein said $V_H$ domain comprises the alanine (Ala) residue at the position corresponding to residue 6 of SEQ ID NO:42, or a conservative substitution thereof, and the lysine (Lys) at the position corresponding to residue 31 of SEQ ID NO:42, or a conservative substitution thereof;

l) a $V_H$ domain comprising an amino acid sequence having at least 85% sequence identity to the amino acid sequence set forth in SEQ ID NO:43, wherein said $V_H$ domain comprises the threonine (Thr) residue at the position corresponding to residue 23 of SEQ ID NO:43, or a conservative substitution thereof, and the lysine (Lys) at the position corresponding to residue 31 of SEQ ID NO:43, or a conservative substitution thereof;

m) a $V_H$ domain comprising an amino acid sequence having at least 85% sequence identity to the amino acid sequence set forth in SEQ ID NO:44, wherein said $V_H$ domain comprises the alanine (Ala) residue at the position corresponding to residue 6 of SEQ ID NO:44, or a conservative substitution thereof, and the phenylalanine (Phe) at the position corresponding to residue 57 of SEQ ID NO:44, or a conservative substitution thereof;

n) a $V_H$ domain comprising an amino acid sequence having at least 85% sequence identity to the amino acid sequence set forth in SEQ ID NO:45, wherein said $V_H$ domain comprises the alanine (Ala) residue at the position corresponding to residue 6 of SEQ ID NO:45, or a conservative substitution thereof, and the tyrosine (Tyr) at the position corresponding to residue 57 of SEQ ID NO:45, or a conservative substitution thereof;

o) a $V_H$ domain comprising an amino acid sequence having at least 85% sequence identity to the amino acid sequence set forth in SEQ ID NO:46, wherein said $V_H$ domain comprises the alanine (Ala) residue at the position corresponding to residue 6 of SEQ ID NO:46, or a conservative substitution thereof, and the phenylalanine (Phe) at the position corresponding to residue 59 of SEQ ID NO:46, or a conservative substitution thereof;

p) a $V_H$ domain comprising an amino acid sequence having at least 85% sequence identity to the amino acid sequence set forth in SEQ ID NO:47, wherein said $V_H$ domain comprises the alanine (Ala) residue at the position corresponding to residue 6 of SEQ ID NO:47, or a conservative substitution thereof, and the phenylalanine (Phe) at the position corresponding to residue 60 of SEQ ID NO:47, or a conservative substitution thereof;

q) a $V_H$ domain comprising an amino acid sequence having at least 85% sequence identity to the amino acid sequence set forth in SEQ ID NO:48, wherein said $V_H$ domain comprises the alanine (Ala) residue at the position corresponding to residue 6 of SEQ ID NO:48, or a conservative substitution thereof, and the valine (Val) at the position corresponding to residue 60 of SEQ ID NO:48, or a conservative substitution thereof;

r) a $V_H$ domain comprising an amino acid sequence having at least 85% sequence identity to the amino acid sequence set forth in SEQ ID NO:49, wherein said $V_H$ domain comprises the threonine (Thr) residue at the position corresponding to residue 23 of SEQ ID NO:49, or a conservative substitution thereof, and the phenylalanine (Phe) at the position corresponding to residue 57 of SEQ ID NO:49, or a conservative substitution thereof;

s) a $V_H$ domain comprising an amino acid sequence having at least 85% sequence identity to the amino acid sequence set forth in SEQ ID NO:50, wherein said $V_H$ domain comprises the threonine (Thr) residue at the position corresponding to residue 23 of SEQ ID NO:50, or a conservative substitution thereof, and the tyrosine (Tyr) at the position corresponding to residue 57 of SEQ ID NO:50, or a conservative substitution thereof;

t) a $V_H$ domain comprising an amino acid sequence having at least 85% sequence identity to the amino acid sequence set forth in SEQ ID NO:51, wherein said $V_H$ domain comprises the threonine (Thr) residue at the position corresponding to residue 23 of SEQ ID NO:51, or a conservative substitution thereof, and the phenylalanine (Phe) at the position corresponding to residue 59 of SEQ ID NO:51, or a conservative substitution thereof;

u) a $V_H$ domain comprising an amino acid sequence having at least 85% sequence identity to the amino acid sequence set forth in SEQ ID NO:52, wherein said $V_H$ domain comprises the threonine (Thr) residue at the position corresponding to residue 23 of SEQ ID NO:52, or a conservative substitution thereof, and the phenylalanine (Phe) at the position corresponding to residue 60 of SEQ ID NO:52, or a conservative substitution thereof;

v) a $V_H$ domain comprising an amino acid sequence having at least 85% sequence identity to the amino acid sequence set forth in SEQ ID NO:53, wherein said $V_H$ domain comprises the threonine (Thr) residue at the position corresponding to residue 23 of SEQ ID NO:53, or a conservative substitution thereof, and the valine at the position corresponding to residue 60 of SEQ ID NO:53, or a conservative substitution thereof; and, w) a $V_H$ domain comprising an amino acid sequence having at least 85% sequence identity to the amino acid sequence set forth in SEQ ID NO:54, wherein said $V_H$ domain comprises the threonine (Thr) residue at the position corresponding to residue 23 of SEQ ID NO:54, or a conservative substitution thereof, and the tyrosine at the position corresponding to residue 104 of SEQ ID NO:54, or a conservative substitution thereof.

In a further embodiment, the present invention includes an isolated polynucleotide comprising, consisting essentially of, or consisting of a nucleic acid encoding a $V_H$ domain, where the nucleic acid has a sequence that has at least about 80%, about 85%, about 90%, about 91%, about 92%, about 93%, about 94%, about 95%, about 96%, about 97%, about 98%, about 99%, or 100% sequence identity to a nucleotide sequence selected from the group consisting of SEQ ID NOS: 59-61, and wherein an anti-CD100 antibody comprising the encoded $V_H$ domain specifically or preferentially binds to anti-CD100.

In further embodiments, the present invention includes an isolated polynucleotide comprising, consisting essentially of, or consisting of a nucleic acid encoding a $V_L$ domain of an immunoglobulin light chain, where the $V_L$ domain is selected from the group consisting of SEQ ID NO:4, 5, or 7.

In yet a further embodiment, the present invention includes an isolated polynucleotide comprising, consisting essentially of, or consisting of a nucleic acid encoding a $V_L$ domain that has an amino acid sequence that is at least about 80%, about 85%, about 90%, about 95%, about 96%, about 97%, about 98%, about 99%, or 100% identical to a reference $V_L$ domain polypeptide sequence set forth in SEQ ID NO:4, 5, or 7, wherein an anti-CD100 antibody comprising the encoded $V_L$ domain specifically or preferentially binds to CD100.

Any of the polynucleotides described above may further include additional nucleic acids, encoding, e.g., a signal peptide to direct secretion of the encoded polypeptide, antibody constant regions as described herein, or other heterologous polypeptides as described herein. Also, as described in more detail elsewhere herein, the present invention includes compositions comprising one or more of the polynucleotides described above. In one embodiment, the invention includes compositions comprising a first polynucleotide and second polynucleotide wherein said first polynucleotide encodes a $V_H$ domain as described herein and wherein said second polynucleotide encodes a $V_L$ domain as described herein. Specifically a composition which comprises, consists essentially of, or consists of a $V_H$ domain-encoding polynucleotide, as set forth in any one of SEQ ID NO:59-61, and a $V_L$ domain-encoding polynucleotide, for example, a polynucleotide encoding the $V_L$ domain as set forth in SEQ ID NO:62-64.

The present invention also includes fragments of the polynucleotides of the invention, as described elsewhere. Additionally polynucleotides that encode fusion polypolypeptides, Fab fragments, and other derivatives, as described herein, are also contemplated by the invention.

The polynucleotides may be produced or manufactured by any method known in the art. For example, if the nucleotide sequence of the antibody is known, a polynucleotide encoding the antibody may be assembled from chemically synthesized oligonucleotides (e.g., as described in Kutmeier et al. (1994) *Bio Techniques* 17:242), which, briefly, involves the synthesis of overlapping oligonucleotides containing portions of the sequence encoding the antibody, annealing and ligating of those oligonucleotides, and then amplification of the ligated oligonucleotides by PCR.

Alternatively, a polynucleotide encoding an anti-CD100 antibody, or antigen-binding fragment, variant, or derivative thereof, may be generated from nucleic acid from a suitable source. If a clone containing a nucleic acid encoding a particular antibody is not available, but the sequence of the antibody molecule is known, a nucleic acid encoding the antibody may be chemically synthesized or obtained from a suitable source (e.g., an antibody cDNA library, or a cDNA library generated from, or nucleic acid, preferably poly A+RNA, isolated from, any tissue or cells expressing the antibody or other anti-CD100 antibody, such as hybridoma cells selected to express an antibody) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody or other anti-CD100 antibody. Amplified nucleic acids generated by PCR may then be cloned into replicable cloning vectors using any method well known in the art.

Once the nucleotide sequence and corresponding amino acid sequence of the anti-CD100 antibody, or antigen-binding fragment, variant, or derivative thereof is determined, its nucleotide sequence may be manipulated using methods well known in the art for the manipulation of nucleotide sequences, e.g., recombinant DNA techniques, site directed mutagenesis, PCR, etc. (see, for example, the techniques described in Sambrook et al. (1990) *Molecular Cloning, A Laboratory Manual* (2nd ed.; Cold Spring Harbor Laboratory, Cold Spring Harbor, N.Y.) and Ausubel et al., eds. (1998) *Current Protocols in Molecular Biology* (John Wiley & Sons, NY), which are both incorporated by reference herein in their entireties), to generate antibodies having a different amino acid sequence, for example to create amino acid substitutions, deletions, and/or insertions.

A polynucleotide encoding an anti-CD100 antibody, or antigen-binding fragment, variant, or derivative thereof, can be composed of any polyribonucleotide or polydeoxyribonucleotide, which may be unmodified RNA or DNA or modified RNA or DNA. For example, a polynucleotide encoding anti-CD100 antibody, or antigen-binding fragment, variant, or derivative thereof can be composed of single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, a polynucleotide encoding an anti-CD100 antibody, or antigen-binding fragment, variant, or derivative thereof can be composed of triple-stranded regions comprising RNA or DNA or both RNA and DNA. A polynucleotide encoding an anti-CD100 antibody, or antigen-binding fragment, variant, or derivative thereof, may also contain one or more modified bases or DNA or RNA backbones modified for stability or for other reasons. "Modified" bases include, for example, tritylated bases and unusual bases such as inosine. A variety of modifications can be made to DNA and RNA; thus, "polynucleotide" embraces chemically, enzymatically, or metabolically modified forms.

An isolated polynucleotide encoding a non-natural variant of a polypeptide derived from an immunoglobulin (e.g., an immunoglobulin heavy chain portion or light chain portion) can be created by introducing one or more nucleotide substitutions, additions or deletions into the nucleotide sequence of the immunoglobulin such that one or more amino acid substitutions, additions or deletions are introduced into the encoded protein. Mutations may be introduced by standard techniques, such as site-directed mutagenesis and PCR-mediated mutagenesis. Preferably, conservative amino acid substitutions are made at one or more non-essential amino acid residues.

V. Fusion Proteins and Antibody Conjugates

As discussed in more detail elsewhere herein, anti-CD100 antibodies of the invention, or antigen-binding fragments, variants, or derivatives thereof, may further be recombinantly fused to a heterologous polypeptide at the N- or C-terminus or chemically conjugated (including covalent and non-covalent conjugations) to polypeptides or other compositions. For example, anti-CD100 antibodies may be recombinantly fused or conjugated to molecules useful as labels in detection assays and effector molecules such as heterologous polypeptides, drugs, radionuclides, or toxins. See, e.g., PCT publications WO 92/08495; WO 91/14438; WO 89/12624; U.S. Pat. No. 5,314,995; and EP 396,387.

Anti-CD100 antibodies of the invention, or antigen-binding fragments, variants, or derivatives thereof, include derivatives that are modified, i.e., by the covalent attachment of any type of molecule to the antibody such that covalent attachment does not prevent the antibody binding anti-CD100. For example, but not by way of limitation, the antibody derivatives include antibodies that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, etc. Additionally, the derivative may contain one or more non-classical amino acids.

Anti-CD100 antibodies of the invention, or antigen-binding fragments, variants, or derivatives thereof, can be composed of amino acids joined to each other by peptide bonds or modified peptide bonds, i.e., peptide isosteres, and may contain amino acids other than the 20 gene-encoded amino acids. Anti-CD100 antibodies may be modified by natural processes, such as posttranslational processing, or by chemical modification techniques that are well known in the art. Such modifications are well described in basic texts and in more detailed monographs, as well as in a voluminous research literature. Modifications can occur anywhere in the anti-CD100 antibody, including the peptide backbone, the amino acid side-chains and the amino or carboxyl termini, or on moieties such as carbohydrates. It will be appreciated that the same type of modification may be present in the same or varying degrees at several sites in a given anti-CD100 antibody. Also, a given anti-CD100 antibody may contain many types of modifications. Anti-CD100 antibodies may be branched, for example, as a result of ubiquitination, and they may be cyclic, with or without branching. Cyclic, branched, and branched cyclic anti-CD100 antibodies may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination. (See, for instance, *Proteins—Structure and Molecular Properties*, T. E. Creighton, W. H. Freeman and Company, NY; 2nd ed. (1993); Johnson, ed. (1983) *Posttranslational Covalent Modification of Proteins* (Academic Press, NY), pgs. 1-12; Seifter et al. (1990) *Meth. Enzymol.* 182:626-646; Rattan et al. (1992) *Ann. NY Acad. Sci.* 663:48-62).

The present invention also provides for fusion proteins comprising an anti-CD100 antibody, or antigen-binding fragment, variant, or derivative thereof, and a heterologous polypeptide. The heterologous polypeptide to which the antibody is fused may be useful for function or is useful to target the anti-CD100 polypeptide expressing cells. In one embodiment, a fusion protein of the invention comprises, consists essentially of, or consists of, a polypeptide having the amino acid sequence of any one or more of the $V_H$ domains of an antibody of the invention or the amino acid sequence of any one or more of the $V_L$ domains of an antibody of the invention or fragments or variants thereof, and a heterologous polypeptide sequence. In another embodiment, a fusion protein for use in the diagnostic and treatment methods disclosed herein comprises, consists essentially of, or consists of a polypeptide having the amino acid sequence of any one, two, three of the CDRs of the $V_H$ domain of an anti-CD100 antibody, or fragments, variants, or derivatives thereof, or the amino acid sequence of any one, two, three of the CDRs of the $V_L$ domain an anti-CD100 antibody, or fragments, variants, or derivatives thereof, and a heterologous polypeptide sequence. In one embodiment, a fusion protein comprises a polypeptide having the amino acid sequence of at least one $V_H$ domain of an anti-CD100 antibody of the invention and the amino acid sequence of at least one $V_L$ domain of an anti-CD100 antibody of the invention or fragments, derivatives or variants thereof, and a heterologous polypeptide sequence. Preferably, the $V_H$ and $V_L$ domains of the fusion protein correspond to a single source antibody (or scFv or Fab fragment) that specifically binds at least one epitope of CD100. In yet another embodiment, a fusion protein for use in the diagnostic and treatment methods disclosed herein comprises a polypeptide having the amino acid sequence of any one, two, three or more of the CDRs of the $V_H$ domain of an anti-CD100 antibody and the amino acid sequence of any one, two, three or more of the CDRs of the $V_L$ domain of an anti-CD100 antibody, or fragments or variants thereof, and a heterologous polypeptide sequence. Preferably, two, three, four, five, six, or more of the CDR(s) of the $V_H$ domain or $V_L$ domain correspond to single source antibody (or scFv or Fab fragment) of the invention. Nucleic acid molecules encoding these fusion proteins are also encompassed by the invention.

Exemplary fusion proteins reported in the literature include fusions of the T cell receptor (Gascoigne et al. (1987) *Proc. Natl. Acad. Sci. USA* 84:2936-2940); CD4 (Capon et al. (1989) *Nature* 337:525-531; Traunecker et al. (1989) *Nature* 339:68-70; Zettmeissl et al. (1990) *DNA Cell Biol. USA* 9:347-353; and Byrn et al. (1990) *Nature* 344:667-670); L-selectin (homing receptor) (Watson et al. (1990) *J. Cell. Biol.* 110:2221-2229; and Watson et al. (1991) *Nature* 349:164-167); CD44 (Aruffo et al. (1990) *Cell* 61:1303-1313); CD28 and B7 (Linsley et al. (1991) *J. Exp. Med.* 173:721-730); CTLA-4 (Lisley et al. (1991) *J. Exp. Med.* 174:561-569); CD22 (Stamenkovic et al. (1991) *Cell* 66:1133-1144); TNF receptor (Ashkenazi et al. (1991) *Proc. Natl. Acad. Sci. USA* 88:10535-10539; Lesslauer et al. (1991) *Eur. J. Immunol.* 27:2883-2886; and Peppel et al. (1991) *J. Exp. Med.* 174: 1483-1489); and IgE receptor a (Ridgway and Gorman (1991) *J. Cell. Biol.* Vol. 115, Abstract No. 1448).

As discussed elsewhere herein, anti-CD100 antibodies of the invention, or antigen-binding fragments, variants, or derivatives thereof, may be fused to heterologous polypeptides to increase the in vivo half life of the polypeptides or for use in immunoassays using methods known in the art. For example, in one embodiment, PEG can be conjugated to the anti-CD100 antibodies of the invention to increase their half-life in vivo. See Leong et al. (2001) *Cytokine* 16:106; *Adv. in Drug Deliv. Rev.* (2002) 54:531; or Weir et al. (2002) *Biochem. Soc. Transactions* 30:512.

Moreover, anti-CD100 antibodies of the invention, or antigen-binding fragments, variants, or derivatives thereof, can be fused to marker sequences, such as a peptide to facilitate their purification or detection. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al. (1989) *Proc. Natl. Acad. Sci. USA* 86:821-824, for instance, hexa-histidine provides for convenient purification of the fusion protein. Other peptide tags useful for purification include, but are not limited to, the "HA" tag, which corresponds to an epitope derived from the influenza hemagglutinin protein (Wilson et al. (1984) Cell 37:767) and the "flag" tag.

Fusion proteins can be prepared using methods that are well known in the art (see for example U.S. Pat. Nos. 5,116,964 and 5,225,538). The precise site at which the fusion is made may be selected empirically to optimize the secretion or binding characteristics of the fusion protein. DNA encoding the fusion protein is then transfected into a host cell for expression.

Anti-CD100 antibodies of the present invention, or antigen-binding fragments, variants, or derivatives thereof, may be used in non-conjugated form or may be conjugated to at least one of a variety of molecules, e.g., to improve the therapeutic properties of the molecule, to facilitate target detection, or for imaging or therapy of the patient. Anti-CD100 antibodies of the invention, or antigen-binding fragments, variants, or derivatives thereof, can be labeled or conjugated either before or after purification, or when purification is performed.

In particular, anti-CD100 antibodies of the invention, or antigen-binding fragments, variants, or derivatives thereof, may be conjugated to therapeutic agents, prodrugs, peptides, proteins, enzymes, viruses, lipids, biological response modifiers, pharmaceutical agents, or PEG.

Those skilled in the art will appreciate that conjugates may also be assembled using a variety of techniques depending on the selected agent to be conjugated. For example, conjugates with biotin are prepared, e.g., by reacting a binding polypeptide with an activated ester of biotin such as the biotin N-hydroxysuccinimide ester. Similarly, conjugates with a fluorescent marker may be prepared in the presence of a coupling agent, e.g. those listed herein, or by reaction with an isothiocyanate, preferably fluorescein-isothiocyanate. Conjugates of the anti-CD100 antibodies of the invention, or antigen-binding fragments, variants, or derivatives thereof, are prepared in an analogous manner.

The present invention further encompasses anti-CD100 antibodies of the invention, or antigen-binding fragments, variants, or derivatives thereof, conjugated to a diagnostic or therapeutic agent. The anti-CD100 antibodies, including antigen-binding fragments, variants, and derivatives thereof, can be used diagnostically to, for example, monitor the development or progression of a disease as part of a clinical testing procedure to, e.g., determine the efficacy of a given treatment and/or prevention regimen. Detection can be facilitated by coupling the anti-CD100 antibody, or antigen-binding fragment, variant, or derivative thereof, to a detectable substance. Examples of detectable substances include various enzymes, prosthetic groups, fluorescent materials, luminescent materials, bioluminescent materials, radioactive materials, positron emitting metals using various positron emission tomographies, and nonradioactive paramagnetic metal ions. See, for example, U.S. Pat. No. 4,741,900 for metal ions which can be conjugated to antibodies for use as diagnostics according to the present invention. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include $^{125}I$, $^{131}I$, $^{111}In$, $^{90}Y$, or $^{99}Tc$.

An anti-CD100 antibody, or antigen-binding fragment, variant, or derivative thereof, may be conjugated to a therapeutic moiety such as a cytotoxin, a therapeutic agent or a radioactive metal ion. A cytotoxin or cytotoxic agent includes any agent that is detrimental to cells. Examples include selenium, taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine). The conjugates of the invention can be used for modifying a given biological response. The drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, alpha-interferon, beta-interferon, nerve growth factor, platelet derived growth factor, tissue plasminogen activator; or, biological response modifiers such as, for example, lymphokines, interleukin-1 ("IL-1"), interleukin-2 ("IL-2"), interleukin-6 ("IL-6"), granulocyte macrophase colony stimulating factor ("GM-CSF"), granulocyte colony stimulating factor ("G-CSF"), or other growth factors.

An anti-CD100 antibody, or antigen-binding fragment, variant, or derivative thereof, also can be detectably labeled by coupling it to a chemiluminescent compound. The presence of the chemiluminescent-tagged anti-CD100 antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

One of the ways in which an anti-CD100 antibody, or antigen-binding fragment, variant, or derivative thereof, can be detectably labeled is by linking the same to an enzyme and using the linked product in an enzyme immunoassay (EIA) (Voller, A., "The Enzyme Linked Immunosorbent Assay (ELISA)" *Microbiological Associates Quarterly Publication*, Walkersville, Md.; *Diagnostic Horizons* (1978) 2:1-7; Voller et al. (1978) *J. Clin. Pathol.* 31:507-520; Butler (1981) *Meth. Enzymol.* 73:482-523; Maggio, ed. (1980) *Enzyme Immunoassay*, CRC Press, Boca Raton, Fla.; Ishikawa et al., eds. (1981) *Enzyme Immunoassay* (Kgaku Shoin, Tokyo). The enzyme, which is bound to the anti-CD100 antibody will react with an appropriate substrate, preferably a chromogenic substrate, in such a manner as to produce a chemical moiety which can be detected, for example, by spectrophotometric, fluorimetric or by visual means. Enzymes which can be used to detectably label the antibody include, but are not limited to, malate dehydrogenase, staphylococcal nuclease, delta-5-steroid isomerase, yeast alcohol dehydrogenase, alpha-glycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. Additionally, the detection can be accomplished by colorimetric methods which employ a chromogenic substrate for the enzyme. Detection may also be accomplished by visual comparison of the extent of enzymatic reaction of a substrate in comparison with similarly prepared standards.

Detection may also be accomplished using any of a variety of other immunoassays. For example, by radioactively labeling the anti-CD100 antibody, or antigen-binding fragment, variant, or derivative thereof, it is possible to detect the antibody through the use of a radioimmunoassay (RIA) (see, for example, Weintraub (March, 1986) *Principles of Radioimmunoassays, Seventh Training Course on Radioligand Assay Techniques* (The Endocrine Society), which is incorporated by reference herein). The radioactive isotope can be detected by means including, but not limited to, a gamma counter, a scintillation counter, or autoradiography.

An anti-CD100 antibody, or antigen-binding fragment, variant, or derivative thereof, can also be detectably labeled using fluorescence emitting metals such as 152Eu, or others of the lanthanide series. These metals can be attached to the antibody using such metal chelating groups as diethylenetriaminepentacetic acid (DTPA) or ethylenediaminetetraacetic acid (EDTA).

Techniques for conjugating various moieties to an anti-CD100 antibody, or antigen-binding fragment, variant, or derivative thereof, are well known, see, e.g., Amon et al. (1985) "Monoclonal Antibodies for Immunotargeting of Drugs in Cancer Therapy," in *Monoclonal Antibodies and Cancer Therapy*, ed. Reisfeld et al. (Alan R. Liss, Inc.), pp. 243-56; Hellstrom et al. (1987) "Antibodies for Drug Delivery," in *Controlled Drug Delivery*, ed. Robinson et al. (2nd ed.; Marcel Dekker, Inc.), pp. 623-53); Thorpe (1985) "Antibody Carriers of Cytotoxic Agents in Cancer Therapy: A Review," in *Monoclonal Antibodies '84: Biological and Clinical Applications*, ed. Pinchera et al., pp. 475-506; "Analysis, Results, and Future Prospective of the Therapeutic Use of Radiolabeled Antibody in Cancer Therapy," in *Monoclonal Antibodies for Cancer Detection and Therapy*, ed. Baldwin et al., Academic Press, pp. 303-16 (1985); and Thorpe et al. (1982) "The Preparation and Cytotoxic Properties of Antibody-Toxin Conjugates," *Immunol. Rev.* 62:119-58.

VI. Expression of Antibody Polypeptides

DNA sequences that encode the light and the heavy chains of the antibody may be made, either simultaneously or separately, using reverse transcriptase and DNA polymerase in accordance with well known methods. PCR may be initiated by consensus constant region primers or by more specific primers based on the published heavy and light chain DNA and amino acid sequences. As discussed above, PCR also may be used to isolate DNA clones encoding the antibody light and heavy chains. In this case the libraries may be screened by consensus primers or larger homologous probes, such as mouse constant region probes.

DNA, typically plasmid DNA, may be isolated from the cells using techniques known in the art, restriction mapped and sequenced in accordance with standard, well known techniques set forth in detail, e.g., in the foregoing references relating to recombinant DNA techniques. Of course, the DNA may be synthetic according to the present invention at any point during the isolation process or subsequent analysis.

Following manipulation of the isolated genetic material to provide anti-CD100 antibodies, or antigen-binding fragments, variants, or derivatives thereof, of the invention, the polynucleotides encoding the anti-CD100 antibodies are typically inserted in an expression vector for introduction into host cells that may be used to produce the desired quantity of anti-CD100 antibody.

Recombinant expression of an antibody, or fragment, derivative or analog thereof, e.g., a heavy or light chain of an antibody that binds to a target molecule described herein, e.g., CD100, requires construction of an expression vector containing a polynucleotide that encodes the antibody. Once a polynucleotide encoding an antibody molecule or a heavy or light chain of an antibody, or portion thereof (preferably containing the heavy or light chain variable domain), of the invention has been obtained, the vector for the production of the antibody molecule may be produced by recombinant DNA technology using techniques well known in the art. Thus, methods for preparing a protein by expressing a polynucleotide containing an antibody encoding nucleotide sequence are described herein. Methods that are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. The invention, thus, provides replicable vectors comprising a nucleotide sequence encoding an antibody molecule of the invention, or a heavy or light chain thereof, or a heavy or light chain variable domain, operably linked to a promoter. Such vectors may include the nucleotide sequence encoding the constant region of the antibody molecule (see, e.g., PCT Publication WO 86/05807; PCT Publication WO 89/01036; and U.S. Pat. No. 5,122,464) and the variable domain of the antibody may be cloned into such a vector for expression of the entire heavy or light chain.

The term "vector" or "expression vector" is used herein to mean vectors used in accordance with the present invention as a vehicle for introducing into and expressing a desired gene in a host cell. As known to those skilled in the art, such vectors may easily be selected from the group consisting of plasmids, phages, viruses and retroviruses. In general, vectors compatible with the instant invention will comprise a selection marker, appropriate restriction sites to facilitate cloning of the desired gene and the ability to enter and/or replicate in eukaryotic or prokaryotic cells.

For the purposes of this invention, numerous expression vector systems may be employed. For example, one class of vector utilizes DNA elements that are derived from animal viruses such as bovine papilloma virus, polyoma virus, adenovirus, vaccinia virus, baculovirus, retroviruses (RSV, MMTV or MOMLV) or SV40 virus. Others involve the use of polycistronic systems with internal ribosome binding sites. Additionally, cells that have integrated the DNA into their chromosomes may be selected by introducing one or more markers which allow selection of transfected host cells. The marker may provide for prototrophy to an auxotrophic host, biocide resistance (e.g., antibiotics) or resistance to heavy metals such as copper. The selectable marker gene can either be directly linked to the DNA sequences to be expressed, or introduced into the same cell by cotransformation. Additional elements may also be needed for optimal synthesis of mRNA. These elements may include signal sequences, splice signals, as well as transcriptional promoters, enhancers, and termination signals.

In particularly preferred embodiments the cloned variable region genes are inserted into an expression vector along with the heavy and light chain constant region genes (preferably human) synthesized as discussed above. Of course, any expression vector that is capable of eliciting expression in eukaryotic cells may be used in the present invention. Examples of suitable vectors include, but are not limited to plasmids pcDNA3, pHCMV/Zeo, pCR3.1, pEF 1/His, pIND/GS, pRc/HCMV2, pSV40/Zeo2, pTRACER-HCMV, pUB6/V5-His, pVAX1, and pZeoSV2 (available from Invitrogen, San Diego, Calif.), and plasmid pCI (available from Promega, Madison, Wis.). In general, screening large numbers of transformed cells for those that express suitably high levels if immunoglobulin heavy and light chains is routine experimentation that can be carried out, for example, by robotic systems.

More generally, once the vector or DNA sequence encoding a monomeric subunit of the anti-CD100 antibody has been prepared, the expression vector may be introduced into an appropriate host cell. Introduction of the plasmid into the host cell can be accomplished by various techniques well known to those of skill in the art. These include, but are not limited to, transfection (including electrophoresis and electroporation), protoplast fusion, calcium phosphate precipitation, cell fusion with enveloped DNA, microinjection, and infection with intact virus. See, Ridgway (1988) "Mammalian Expression Vectors" in Vectors, ed. Rodriguez and Denhardt (Butterworths, Boston, Mass.), Chapter 24.2, pp. 470-472. Typically, plasmid introduction into the host is via electroporation. The host cells harboring the expression construct are grown under conditions appropriate to the production of the light chains and heavy chains, and assayed for heavy and/or light chain protein synthesis. Exemplary assay techniques include enzyme-linked immunosorbent assay (ELISA), radioimmunoassay (RIA), or fluorescence-activated cell sorter analysis (FACS), immunohistochemistry and the like.

The expression vector is transferred to a host cell by conventional techniques, and the transfected cells are then cultured by conventional techniques to produce an antibody for use in the methods described herein. Thus, the invention includes host cells containing a polynucleotide encoding an antibody of the invention, or a heavy or light chain thereof, operably linked to a heterologous promoter. In preferred embodiments for the expression of double-chained antibodies, vectors encoding both the heavy and light chains may be co-expressed in the host cell for expression of the entire immunoglobulin molecule, as detailed below.

As used herein, "host cells" refers to cells that harbor vectors constructed using recombinant DNA techniques and encoding at least one heterologous gene. In descriptions of processes for isolation of antibodies from recombinant hosts, the terms "cell" and "cell culture" are used interchangeably to denote the source of antibody unless it is clearly specified otherwise. In other words, recovery of polypeptide from the "cells" may mean either from spun down whole cells, or from the cell culture containing both the medium and the suspended cells.

A variety of host-expression vector systems may be utilized to express antibody molecules for use in the methods described herein. Such host-expression systems represent vehicles by which the coding sequences of interest may be produced and subsequently purified, but also represent cells that may, when transformed or transfected with the appropriate nucleotide coding sequences, express an antibody molecule of the invention in situ. These include, but are not limited to, microorganisms such as bacteria (e.g., *E. coli, B. subtilis*) transformed with recombinant bacteriophage DNA, plasmid DNA or cosmid DNA expression vectors containing antibody coding sequences; yeast (e.g., *Saccharomyces, Pichia*) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BLK, 293, 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Preferably, bacterial cells such as *Escherichia coli*, and more preferably, eukaryotic cells, especially for the expression of whole recombinant antibody molecule, are used for the expression of a recombinant antibody molecule. For example, mammalian cells such as Chinese hamster ovary cells (CHO), in conjunction with a vector such as the major intermediate early gene promoter element from human cytomegalovirus is an effective expression system for antibodies (Foecking et al. (1986) *Gene* 45:101; Cockett et al. (1990) *Bio/Technology* 8:2).

The host cell line used for protein expression is often of mammalian origin; those skilled in the art are credited with ability to preferentially determine particular host cell lines that are best suited for the desired gene product to be expressed therein. Exemplary host cell lines include, but are not limited to, CHO (Chinese Hamster Ovary), DG44 and DUXB11 (Chinese Hamster Ovary lines, DHFR minus), HELA (human cervical carcinoma), CVI (monkey kidney line), COS (a derivative of CVI with SV40 T antigen), VERY, BHK (baby hamster kidney), MDCK, 293, WI38, R1610 (Chinese hamster fibroblast) BALBC/3T3 (mouse fibroblast), HAK (hamster kidney line), SP2/O (mouse myeloma), P3x63-Ag3.653 (mouse myeloma), BFA-1c1BPT (bovine endothelial cells), RAJI (human lymphocyte) and 293 (human kidney). Host cell lines are typically available from commercial services, the American Tissue Culture Collection or from published literature.

In addition, a host cell strain may be chosen that modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells that possess the cellular machinery for proper processing of the primary transcript, glycosylation, and phosphorylation of the gene product may be used.

For long-term, high-yield production of recombinant proteins, stable expression is preferred. For example, cell lines that stably express the antibody molecule may be engineered. Rather than using expression vectors that contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which stably express the antibody molecule.

A number of selection systems may be used, including, but not limited to, the herpes simplex virus thymidine kinase (Wigler et al. (1977) *Cell* 11:223), hypoxanthine-guanine phosphoribosyltransferase (Szybalska and Szybalski (1992) *Proc. Natl. Acad. Sci. USA* 48:202), and adenine phosphoribosyltransferase (Lowy et al. (1980) *Cell* 22:817) genes can be employed in tk-, hgprt- or aprt-cells, respectively. Also, antimetabolite resistance can be used as the basis of selection for the following genes: dhfr, which confers resistance to methotrexate (Wigler et al. (1980) *Natl. Acad. Sci. USA* 77:357; O'Hare et al. (1981) *Proc. Natl. Acad. Sci. USA* 78:1527); gpt, which confers resistance to mycophenolic acid (Mulligan and Berg (1981) *Proc. Natl. Acad. Sci. USA* 78:2072); neo, which confers resistance to the aminoglycoside G-418 Clinical Pharmacy 12:488-505; Wu and Wu (1991) *Biotherapy* 3:87-95; Tolstoshev (1993) *Ann. Rev. Pharmacol. Toxicol.* 32:573-596; Mulligan (1993) *Science* 260:926-932; and Morgan and Anderson (1993) *Ann. Rev. Biochem.* 62:191-217 (1993); *TIB TECH* 11(5):155-215 (May, 1993); and hygro, which confers resistance to hygromycin (Santerre et al. (1984) *Gene* 30:147. Methods commonly known in the art of recombinant DNA technology which can be used are described in Ausubel et al. (1993) *Current Protocols in Molecular Biology* (John Wiley & Sons, NY); Kriegler (1990) "Gene Transfer and Expression" in A Laboratory Manual (Stockton Press, NY); Dracopoli et al. (eds) (1994) *Current Protocols in Human Genetics* (John Wiley & Sons, NY) Chapters 12 and 13; Colberre-Garapin et al. (1981) *J. Mol. Biol.* 150:1, which are incorporated by reference herein in their entireties.

The expression levels of an antibody molecule can be increased by vector amplification (for a review, see Bebbington and Hentschel (1987) "The Use of Vectors Based on Gene Amplification for the Expression of Cloned Genes in Mammalian Cells in DNA Cloning" (Academic Press, NY) Vol. 3. When a marker in the vector system expressing antibody is amplifiable, increase in the level of inhibitor present in culture of host cell will increase the number of copies of the marker gene. Since the amplified region is associated with the antibody gene, production of the antibody will also increase (Crouse et al. (1983) *Mol. Cell. Biol.* 3:257).

In vitro production allows scale-up to give large amounts of the desired polypeptides. Techniques for mammalian cell cultivation under tissue culture conditions are known in the art and include homogeneous suspension culture, e.g. in an airlift reactor or in a continuous stirrer reactor, or immobilized or entrapped cell culture, e.g. in hollow fibers, microcapsules, on agarose microbeads or ceramic cartridges. If necessary and/or desired, the solutions of polypeptides can be purified by the customary chromatography methods, for example gel filtration, ion-exchange chromatography, chromatography over DEAE-cellulose or (immuno-)affinity chromatography, e.g., after preferential biosynthesis of a synthetic hinge region polypeptide or prior to or subsequent to the HIC chromatography step described herein.

Genes encoding anti-CD100 antibodies, or antigen-binding fragments, variants, or derivatives thereof of the invention can also be expressed in non-mammalian cells such as bacteria or yeast or plant cells. Bacteria that readily take up nucleic acids include members of the enterobacteriaceae, such as strains of *Escherichia coli* or *Salmonella*; Bacillaceae, such as *Bacillus subtilis*; *Pneumococcus*; *Streptococcus*, and *Haemophilus influenzae*. It will further be appreciated that, when expressed in bacteria, the heterologous polypeptides typically become part of inclusion bodies. The heterologous polypeptides must be isolated, purified and then assembled into functional molecules. Where tetravalent forms of antibodies are desired, the subunits will then self-assemble into tetravalent antibodies (WO 02/096948A2).

In bacterial systems, a number of expression vectors may be advantageously selected depending upon the use intended for the antibody molecule being expressed. For example, when a large quantity of such a protein is to be produced, for the generation of pharmaceutical compositions of an antibody molecule, vectors which direct the expression of high levels of fusion protein products that are readily purified may be desirable. Such vectors include, but are not limited, to the *E. coli* expression vector pUR278 (Ruther et al. (1983) *EMBO J.* 2:1791), in which the antibody coding sequence may be ligated individually into the vector in frame with the lacZ coding region so that a fusion protein is produced; pIN vectors (Inouye and Inouye (1985) *Nucleic Acids Res.* 13:3101-3109; Van Heeke and Schuster (1989) *J. Biol. Chem.* 24:5503-5509); and the like. pGEX vectors may also be used to express foreign polypeptides as fusion proteins with glutathione S-transferase (GST). In general, such fusion proteins are soluble and can easily be purified from lysed cells by adsorption and binding to a matrix glutathione-agarose beads followed by elution in the presence of free glutathione. The pGEX vectors are designed to include thrombin or factor Xa protease cleavage sites so that the cloned target gene product can be released from the GST moiety.

In addition to prokaryotes, eukaryotic microbes may also be used. *Saccharomyces cerevisiae*, or common baker's yeast, is the most commonly used among eukaryotic microorganisms although a number of other strains are commonly available, e.g., *Pichia pastoris*.

For expression in *Saccharomyces*, the plasmid YRp7, for example, (Stinchcomb et al. (1979) *Nature* 282:39; Kingsman et al. (1979) *Gene* 7:141; Tschemper et al. (1980) *Gene* 10:157) is commonly used. This plasmid already contains the TRP1 gene, which provides a selection marker for a mutant strain of yeast lacking the ability to grow in tryptophan, for example ATCC No. 44076 or PEP4-1 (Jones (1977) *Genetics* 85:12). The presence of the trp1 lesion as a characteristic of the yeast host cell genome then provides an effective environment for detecting transformation by growth in the absence of tryptophan.

In an insect system, *Autographa californica* nuclear polyhedrosis virus (AcNPV) is typically used as a vector to express foreign genes. The virus grows in *Spodoptera frugiperda* cells. The antibody coding sequence may be cloned individually into non-essential regions (for example the polyhedrin gene) of the virus and placed under control of an AcNPV promoter (for example the polyhedrin promoter).

Once an antibody molecule of the invention has been recombinantly expressed, it may be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. Alternatively, a preferred method for increasing the affinity of antibodies of the invention is disclosed in U.S. Patent Application Publication No. 2002 0123057 A1.

VII. Treatment Methods Using Therapeutic Anti-CD100 Antibodies

Methods of the invention are directed to the use of anti-CD100 antibodies, including antigen-binding fragments, variants, and derivatives thereof, to treat patients having a disease associated with soluble CD100 secreted from or expressed on CD100-expressing cells. By "CD100-expressing cell" is intended normal and malignant cells expressing CD100 antigen. Methods for detecting CD100 expression in cells are well known in the art and include, but are not limited to, PCR techniques, immunohistochemistry, flow cytometry, Western blot, ELISA, and the like.

Though the following discussion refers to diagnostic methods and treatment of various diseases and disorders with an anti-CD100 antibody of the invention, the methods described herein are also applicable to the antigen-binding fragments, variants, and derivatives of these anti-CD100 antibodies that retain the desired properties of the anti-CD100 antibodies of the invention, i.e., capable of specifically binding CD100 and having anti-CD100 activity.

"Treatment" is herein defined as the application or administration of an anti-CD100 antibody to a patient, or application or administration of an anti-CD100 antibody to an isolated tissue or cell line from a patient, where the patient has a disease, a symptom of a disease, or a predisposition toward a disease, where the purpose is to cure, heal, alleviate, relieve, alter, remedy, ameliorate, improve, or affect the disease, the symptoms of the disease, or the predisposition toward the disease. By "treatment" is also intended the application or administration of a pharmaceutical composition comprising the anti-CD100 antibody to a patient, or application or administration of a pharmaceutical composition comprising the anti-CD100 antibody to an isolated tissue or cell line from a patient, who has a disease, a symptom of a disease, or a predisposition toward a disease, where the purpose is to cure, heal, alleviate, relieve, alter, remedy, ameliorate, improve, or affect the disease, the symptoms of the disease, or the predisposition toward the disease.

The antibodies of the present invention are useful for the treatment of various malignant and non-malignant tumors. By "anti-tumor activity" is intended a reduction in the rate of malignant CD100-expressing cell proliferation or accumulation, and hence a decline in growth rate of an existing tumor or in a tumor that arises during therapy, and/or destruction of existing neoplastic (tumor) cells or newly formed neoplastic cells, and hence a decrease in the overall size of a tumor during therapy. Therapy with at least one anti-CD100 antibody causes a physiological response that is beneficial with respect to treatment of disease states associated with CD100-expressing cells in a human.

It has been shown that some lymphomas are characterized by high expression of CD100. In this manner, the methods of the invention find use in the treatment of non-Hodgkin's lymphomas related to abnormal, uncontrollable B cell proliferation or accumulation. For purposes of the present invention, such lymphomas will be referred to according to the Working Formulation classification scheme, that is those B cell lymphomas categorized as low grade, intermediate grade, and high grade (see "The Non-Hodgkin's Lymphoma Pathologic Classification Project" in *Cancer* 49:2112-2135 (1982)). Thus, low-grade B cell lymphomas include small lymphocytic, follicular small-cleaved cell, and follicular mixed small-cleaved and large cell lymphomas; intermediate-grade lymphomas include follicular large cell, diffuse small cleaved cell, diffuse mixed small and large cell, and diffuse large cell lymphomas; and high-grade lymphomas include large cell immunoblastic, lymphoblastic, and small non-cleaved cell lymphomas of the Burkitt's and non-Burkitt's type.

It is recognized that the methods of the invention are useful in the therapeutic treatment of B cell lymphomas that are classified according to the Revised European and American Lymphoma Classification (REAL) system. Such B cell lymphomas include, but are not limited to, lymphomas classified as precursor B cell neoplasms, such as B lymphoblastic leukemia/lymphoma; peripheral B cell neoplasms, including B cell chronic lymphocytic leukemia/small lymphocytic lymphoma, lymphoplasmacytoid lymphoma/immunocytoma, mantle cell lymphoma (MCL), follicle center lymphoma (follicular) (including diffuse small cell, diffuse mixed small and large cell, and diffuse large cell lymphomas), marginal zone B cell lymphoma (including extranodal, nodal, and splenic types), hairy cell leukemia, plasmacytoma/myeloma, diffuse large cell B cell lymphoma of the subtype primary mediastinal (thymic), Burkitt's lymphoma, and Burkitt's like high grade B cell lymphoma; acute leukemias; acute lymphocytic leukemias; myeloblastic leukemias; acute myelocytic leukemias; promyelocytic leukemia; myelomonocytic leukemia; monocytic leukemia; erythroleukemia; granulocytic leukemia (chronic myelocytic leukemia); chronic lymphocytic leukemia; polycythemia vera; multiple myeloma; Waldenstrom's macroglobulinemia; heavy chain disease; and unclassifiable low-grade or high-grade B cell lymphomas.

It is recognized that the methods of the invention may be useful in preventing further tumor outgrowths arising during therapy. The methods of the invention are particularly useful in the treatment of subjects having low-grade B cell lymphomas, particularly those subjects having relapses following standard chemotherapy. Low-grade B cell lymphomas are more indolent than the intermediate- and high-grade B cell lymphomas and are characterized by a relapsing/remitting course. Thus, treatment of these lymphomas is improved using the methods of the invention, as relapse episodes are reduced in number and severity.

The antibodies of the present invention can be used therapeutically to block a T cell response, such as T cell proliferation, for the treatment of T cell neoplasms, including T cell prolymphocytic leukemia, T cell large granular lymphocytic leukemia, aggressive NK cell leukemia, adult T cell leukemia/lymphoma, extranodal NK/T cell lymphoma, enteropathy-type T cell lymphoma, hepatosplenic T cell lymphoma, blastic NK cell lymphoma, mycosis fungoides/Sezary syndrome, primary cutaneous CD30-positive T cell lymphoproliferative disorders (including primary cutaneous anaplastic large cell lymphoma and lymphomatoid papulosis), angioimmunoblastic T cell lymphoma, peripheral T cell lymphoma, anaplastic large cell lymphoma.

The antibodies of the present invention are also useful for the treatment of epithelial cell carcinomas, including, for example, squamous cell carcinomas, basal cell carcinomas, transitional cell carcinomas, adenocarcinomas, adnexal carcinomas, mucoepidermoid carcinomas, mucinous carcinomas, serous carcinomas, ductal carcinomas, lobular carcinomas, medullary carcinomas, acinar cell carcinomas, and melanomas.

Further, antibodies of the present invention can also be used to inhibit angiogenesis for the treatment of pathological conditions dependent upon the formation of new blood vessels, including tumor development and macular degeneration. Angiogenesis is a complex multistep morphogenetic event during which endothelial cells, stimulated by major determinants of vascular remodeling, dynamically modify their cell-to-cell and cell-to-matrix contacts and move directionally to be reorganized into a mature vascular tree (Bussolino et al. (1997) *Trends Biochem Sci.* 22:251-256; Risau (1997) *Nature* 386:671-674; Jain (2003) *Nat. Med.* 9:685-693). The formation of new blood vessels is a key step during embryo development, but it also occurs in adults in physiologic and in pathologic conditions, such as retinopathy, rheumatoid arthritis, ischemia, and particularly tumor growth and metastasis (Carmeliet (2003) *Nat. Med.* 9:653-660). This pathological formation of new blood vessels is herein referred to as "invasive angiogenesis." Basile et al. ((2006) *PNAS* 103(24):9017-9022) demonstrated that, when shed from HNSCC cells, CD100 stimulates endothelial cell migration, which was prevented by CD100-blocking antibodies and by CD100 knockdown. CD100 overexpression was also noted in prostate, colon, breast, and lung cancers, suggesting that expression of CD100 is a frequently used strategy by which a wide variety of carcinomas may promote angiogenesis.

In accordance with the methods of the present invention, at least one anti-CD100 antibody as defined elsewhere herein is used to promote a positive therapeutic response with respect to a malignant human cell. By "positive therapeutic response" with respect to cancer treatment is intended an improvement in the disease in association with the anti-tumor activity of these antibodies or fragments thereof, and/or an improvement in the symptoms associated with the disease. That is, an anti-proliferative effect, the prevention of further tumor outgrowths, a reduction in tumor size, a decrease in tumor vasculature, a reduction in the number of cancer cells, and/or a decrease in one or more symptoms associated with the disease can be observed. Thus, for example, an improvement in the disease may be characterized as a complete response. By "complete response" is intended an absence of clinically detectable disease with normalization of any previously abnormal radiographic studies, bone marrow, and cerebrospinal fluid (CSF). Such a response must persist for at least one month following treatment according to the methods of the invention. Alternatively, an improvement in the disease may be categorized as being a partial response. By "partial response" is intended at least about a 50% decrease in all measurable tumor burden (i.e., the number of tumor cells present in the subject) in the absence of new lesions and persisting for at least one month. Such a response is applicable to measurable tumors only.

Tumor response can be assessed for changes in tumor morphology (i.e., overall tumor burden, tumor cell count, and the like) using screening techniques such as bioluminescent imaging, for example, luciferase imaging, bone scan imaging, and tumor biopsy sampling including bone marrow aspiration (BMA). In addition to these positive therapeutic responses, the subject undergoing therapy with the anti-CD100 antibody may experience the beneficial effect of an improvement in the symptoms associated with the disease. For example, the subject may experience a decrease in the so-called B symptoms, i.e., night sweats, fever, weight loss, and/or urticaria.

The anti-CD100 antibodies described herein may also find use in the treatment of inflammatory diseases and deficiencies or disorders of the immune system that are associated with CD100 expressing cells. Inflammatory diseases are characterized by inflammation and tissue destruction, or a combination thereof. By "anti-inflammatory activity" is intended a reduction or prevention of inflammation. "Inflammatory disease" includes any inflammatory immune-mediated process where the initiating event or target of the immune response involves non-self antigen(s), including, for example, alloantigens, xenoantigens, viral antigens, bacterial antigens, unknown antigens, or allergens.

Further, for purposes of the present invention, the term "inflammatory disease(s)" includes "autoimmune disease(s) ." As used herein, the term "autoimmunity" is generally understood to encompass inflammatory immune-mediated processes involving "self" antigens. In autoimmune diseases, self antigen(s) trigger host immune responses.

Also, the present invention includes treatment of inflammation associated with tissue transplant rejection. "Transplant rejection" or "graft rejection" refers to any host-mounted immune response against a graft including but not limited to HLA antigens, blood group antigens, and the like.

The invention can also be used to treat graft versus host disease, such as that associated with bone marrow transplantation, for example. In such graft versus host disease, the donor bone marrow includes lymphocytes and cells that mature into lymphocytes. The donor's lymphocytes recognize the recipient's antigens as non-self and mount an inflammatory immune response. Hence, as used herein, "graft versus host disease" or "graft versus host reaction" refers to any T cell mediated immune response in which donor lymphocytes react to the host's antigens.

The anti-CD100 described herein can be used in accordance with the methods of the invention to treat autoimmune and/or inflammatory disorders including, but not limited to, systemic lupus erythematosus (SLE), CREST syndrome, inflammatory myositis, Sjogren's syndrome, mixed connective tissue disease, multiple sclerosis, inflammatory bowel disease, acute respiratory distress syndrome, pulmonary inflammation, idiopathic pulmonary fibrosis, osteoporosis, delayed type hypersensitivity, asthma, primary biliary cirrhosis, and idiopathic thrombocytopenic purpura, discoid lupus, lupus nephritis, sarcoidosis, inflammatory arthritis, including juvenile arthritis, rheumatoid arthritis, psoriatic arthritis, Reiter's syndrome, ankylosing spondylitis, and gouty arthritis, rejection of an organ or tissue transplant, hyperacute, acute, or chronic rejection and/or graft versus host disease, multiple sclerosis, hyper IgE syndrome, polyarteritis nodosa, primary biliary cirrhosis, inflammatory bowel disease, Crohn's disease, celiac's disease (gluten-sensitive enteropathy), autoimmune hepatitis, pernicious anemia, autoimmune hemolytic anemia, psoriasis, scleroderma, myasthenia gravis, autoimmune thrombocytopenic purpura, autoimmune thyroiditis, Grave's disease, Hasimoto's thyroiditis, immune complex disease, chronic fatigue immune dysfunction syndrome (CFIDS), polymyositis and dermatomyositis, cryoglobulinemia, thrombolysis, cardiomyopathy, pemphigus vulgaris, pulmonary interstitial fibrosis, Type I and Type II diabetes mellitus, type 1, 2, 3, and 4 delayed-type hypersensitivity, allergy or allergic disorders, unwanted/unintended immune responses to therapeutic proteins (see for example, U.S. Patent Application No. US 2002/0119151 and Koren, et al. (2002) *Curr. Pharm. Biotechnol.* 3:349-60), asthma, Churg-Strauss syndrome (allergic granulomatosis), atopic dermatitis, allergic and irritant contact dermatitis, urtecaria, IgE-mediated allergy, atherosclerosis, vasculitis, idiopathic inflammatory myopathies, hemolytic disease, Alzheimer's disease, chronic inflammatory demyelinating polyneuropathy, and the like.

Additional central nervous system (CNS) and peripheral nervous system (PNS) inflammatory disorders encompassed by the present invention include any myelin disorder or disease that affects oligodendrocytes or other myelinating cells, e.g. peripheral myelinating cells, HTLV-1 associated myelopathy, oligodendrogliomas and leucodystrophies, Guillain-Barre syndrome, Alexander disease, Canavan disease, Krabbe disease, Pelizaeus-Merzbacher disease, Zellweger disease, Refsum disease, CACH disease, X-linked adrenoleucodystrophy, adrenoleucodystrophy, adrenomyeloneuropathy or leucodystrophies of undetermined origin, or polyradiculoneuritis as well as chronic polyradiculoneuritis. In another aspect of the invention, the disorder is a post-trauma myelin disorder, as well as CNS or PNS lesions, for example caused by spinal cord injury or stroke.

In some other embodiments, the anti-CD100 antibodies of the invention are useful in treating pulmonary inflammation including but not limited to lung graft rejection, asthma, sarcoidosis, emphysema, cystic fibrosis, idiopathic pulmonary fibrosis, chronic bronchitis, allergic rhinitis and allergic diseases of the lung such as hypersensitivity pneumonitis, eosinophilic pneumonia, bronchiolitis obliterans due to bone marrow and/or lung transplantation or other causes, graft atherosclerosis/graft phlebosclerosis, as well as pulmonary fibrosis resulting from collagen, vascular, and autoimmune diseases such as rheumatoid arthritis and lupus erythematosus.

In accordance with the methods of the present invention, at least one anti-CD100 antibody as defined elsewhere herein is used to promote a positive therapeutic response with respect to treatment or prevention of an autoimmune disease and/or inflammatory disease. By "positive therapeutic response" with respect to an autoimmune disease and/or inflammatory disease is intended an improvement in the disease in association with the anti-inflammatory activity, anti-angiogenic activity, anti-apoptotic activity, or the like, of these antibodies, and/or an improvement in the symptoms associated with the disease. That is, an anti-proliferative effect, the prevention of further proliferation of the CD100-expressing cell, a reduction in the inflammatory response including but not limited to reduced secretion of inflammatory cytokines, adhesion molecules, proteases, immunoglobulins (in instances where the CD100 bearing cell is a B cell), combinations thereof, and the like, increased production of anti-inflammatory proteins, a reduction in the number of autoreactive cells, an increase in immune tolerance, inhibition of autoreactive cell survival, reduction in apoptosis, reduction in endothelial cell migration, increase in spontaneous monocyte migration, reduction in and/or a decrease in one or more symptoms mediated by stimulation of sCD100 or CD100-expressing cells can be observed. Such positive therapeutic responses are not limited to the route of administration and may comprise administration to the donor, the donor tissue (such as for example organ perfusion), the host, any combination thereof, and the like.

Clinical response can be assessed using screening techniques such as magnetic resonance imaging (MRI) scan, x-radiographic imaging, computed tomography (CT) scan, flow cytometry or fluorescence-activated cell sorter (FACS) analysis, histology, gross pathology, and blood chemistry, including but not limited to changes detectable by ELISA, RIA, chromatography, and the like. In addition to these positive therapeutic responses, the subject undergoing therapy with the anti-CD100 antibody or antigen-binding fragment thereof may experience the beneficial effect of an improvement in the symptoms associated with the disease.

By "therapeutically effective dose or amount" or "effective amount" is intended an amount of anti-CD100 that when administered brings about a positive therapeutic response with respect to treatment of a patient with a disease associated with CD100-expressing cells. In some embodiments of the invention, a therapeutically effective dose of the anti-CD100 antibody is in the range from about 0.01 mg/kg to about 40 mg/kg, from about 0.01 mg/kg to about 30 mg/kg, from about 0.1 mg/kg to about 30 mg/kg, from about 1 mg/kg to about 30 mg/kg, from about 3 mg/kg to about 30 mg/kg, from about 3 mg/kg to about 25 mg/kg, from about 3 mg/kg to about 20 mg/kg, from about 5 mg/kg to about 15 mg/kg, or from about 7 mg/kg to about 12 mg/kg. It is recognized that the method of treatment may comprise a single administration of a therapeutically effective dose or multiple administrations of a therapeutically effective dose of the anti-CD100 antibody.

The anti-CD100 antibodies can be used in combination with known chemotherapeutics and cytokines for the treatment of disease states comprising CD100-expressing cells. For example, the anti-CD100 antibodies of the invention can be used in combination with cytokines such as interleukin-2. In another embodiment, the anti-CD100 antibodies of the invention can be used in combination with BD16 or BB18.

In this manner, the anti-CD100 antibodies described herein are administered in combination with at least one other cancer therapy, including, but not limited to, surgery or surgical procedures (e.g. splenectomy, hepatectomy, lymphadenectomy, leukophoresis, bone marrow transplantation, and the like); radiation therapy; chemotherapy, optionally in combination with autologous bone marrow transplant, where suitable chemotherapeutic agents include, but are not limited to, fludarabine or fludarabine phosphate, chlorambucil, vincristine, pentostatin, 2-chlorodeoxyadenosine (cladribine), cyclophosphamide, doxorubicin, prednisone, and combinations thereof, for example, anthracycline-containing regimens such as CAP (cyclophosphamide, doxorubicin plus prednisone), CHOP (cyclophosphamide, vincristine, prednisone plus doxorubicin), VAD (vincritsine, doxorubicin, plus dexamethasone), MP (melphalan plus prednisone), and other cytotoxic and/or therapeutic agents used in chemotherapy such as mitoxantrone, daunorubicin, idarubicin, asparaginase, and antimetabolites, including, but not limited to, cytarabine, methotrexate, 5-fluorouracil decarbazine, 6-thioguanine, 6-mercaptopurine, and nelarabine; other anti-cancer monoclonal antibody therapy (for example, alemtuzumab (Campath®) or other anti-CD52 antibody targeting the CD52 cell-surface glycoprotein on malignant B cells; rituximab (Rituxan®), the fully human antibody HuMax-CD20, R-1594, IMMU-106, TRU-015, AME-133, tositumomab/1-131 tositumomab (Bexxar®)), ibritumomab tiuxetan (Zevalin®), or any other therapeutic anti-CD20 antibody targeting the CD20 antigen on malignant B cells; anti-CD19 antibody (for example, MT103, a bispecific antibody); anti-CD22 antibody (for example, the humanized monoclonal antibody epratuzumab); bevacizumab (Avastin®) or other anti-cancer antibody targeting human vascular endothelial growth factor; anti-CD22 antibody targeting the CD22 antigen on malignant B cells (for example, the monoclonal antibody BL-22, an alphaCD22 toxin); α-M-CSF antibody targeting macrophage colony stimulating factor; antibodies targeting the receptor activator of nuclear factor-kappaB (RANK) and its ligand (RANKL), which are overexpressed in multiple myeloma; anti-CD23 antibody targeting the CD23 antigen on malignant B cells (for example, IDEC-152); anti-CD80 antibody targeting the CD80 antigen (for example, IDEC-114); anti-CD38 antibody targeting the CD38 antigen on malignant B cells; antibodies targeting major histocompatibility complex class II receptors (anti-MHC antibodies) expressed on malignant B cells; anti-CD40 antibodies (for example, SGN-40) targeting the CD40 antigen on malignant B cells; and antibodies targeting tumor necrosis factor-related apoptosis-inducing ligand receptor 1 (TRAIL-R1) (for example, the agonistic human monoclonal antibody HGS-ETR1) and TRAIL-R2 expressed on a number of solid tumors and tumors of hematopoietic origin); small molecule-based cancer therapy, including, but not limited to, microtubule and/or topoisomerase inhibitors (for example, the mitotic inhibitor dolastatin and dolastatin analogues; the tubulin-binding agent T900607; XL119; and the topoisomerase inhibitor aminocamptothecin), SDX-105 (bendamustine hydrochloride), ixabepilone (an epothilone analog, also referred to as BMS-247550), protein kinase C inhibitors, for example, midostaurin ((PKC-412, CGP 41251, N-benzoylstaurosporine), pixantrone, eloxatin (an antineoplastic agent), ganite (gallium nitrate), Thalomid® (thalidomide), immunomodulatory derivatives of thalidomide (for example, revlimid (formerly revimid)), Affinitak™ (antisense inhibitor of protein kinase C-alpha), SDX-101 (R-etodolac, inducing apoptosis of malignant lymphocytes), second-generation purine nucleoside analogs such as clofarabine, inhibitors of production of the protein Bcl-2 by cancer cells (for example, the antisense agents oblimersen and Genasense®, proteasome inhibitors (for example, Velcade™ (bortezomib)), small molecule kinase inhibitors (for example, CHIR-258), small molecule VEGF inhibitors (for example, ZD-6474), small molecule inhibitors of heat shock protein (HSP) 90 (for example, 17-AAG), small molecule inhibitors of histone deacetylases (for example, hybrid/polar cytodifferentiation HPC) agents such as suberanilohydroxamic acid (SAHA), and FR-901228) and apoptotic agents such as Trisenox® (arsenic trioxide) and Xcytrin® (motexafin gadolinium); vaccine /immunotherapy-based cancer therapies, including, but not limited to, vaccine approaches (for example, Id-KLH, oncophage, vitalethine), personalized immunotherapy or active idiotype immunotherapy (for example, MyVax® Personalized Immunotherapy, formally designated GTOP-99), Promune® (CpG 7909, a synthetic agonist for toll-like receptor 9 (TLR9)), interferon-alpha therapy, interleukin-2 (IL-2) therapy, IL-12 therapy, IL-15 therapy, and IL-21 therapy; steroid therapy; or other cancer therapy; where the additional cancer therapy is administered prior to, during, or subsequent to the anti-CD100 antibody therapy.

Thus, where the combined therapies comprise administration of an anti-CD100 antibody in combination with administration of another therapeutic agent, as with chemotherapy, radiation therapy, other anti-cancer antibody therapy, small molecule-based cancer therapy, or vaccine/immunotherapy-based cancer therapy, the methods of the invention encompass coadministration, using separate formulations or a single pharmaceutical formulation, or and consecutive administration in either order. Where the methods of the present invention comprise combined therapeutic regimens, these therapies can be given simultaneously, i.e., the anti-CD100 antibody is administered concurrently or within the same time frame as the other cancer therapy (i.e., the therapies are going on concurrently, but the anti-CD100 antibody is not administered precisely at the same time as the other cancer therapy). Alternatively, the anti-CD100 antibody of the present invention may also be administered prior to or subsequent to the other cancer therapy. Sequential administration of the different cancer therapies may be performed regardless of whether the treated subject responds to the first course of therapy to decrease the possibility of remission or relapse. Where the combined therapies comprise administration of the anti-CD100 antibody in combination with administration of a cytotoxic agent, preferably the anti-CD100 antibody is administered prior to administering the cytotoxic agent.

In some embodiments of the invention, the anti-CD100 antibodies described herein are administered in combination with chemotherapy, and optionally in combination with autologous bone marrow transplantation, wherein the antibody and the chemotherapeutic agent(s) may be administered sequentially, in either order, or simultaneously (i.e., concurrently or within the same time frame). Examples of suitable chemotherapeutic agents include, but are not limited to, fludarabine or fludarabine phosphate, chlorambucil, vincristine, pentostatin, 2-chlorodeoxyadenosine (cladribine), cyclophosphamide, doxorubicin, prednisone, and combinations thereof, for example, anthracycline-containing regimens such as CAP (cyclophosphamide, doxorubicin plus prednisone), CHOP (cyclophosphamide, vincristine, prednisone plus doxorubicin), VAD (vincritsine, doxorubicin, plus dexamethasone), MP (melphalan plus prednisone), and other cytotoxic and/or therapeutic agents used in chemotherapy such as mitoxantrone, daunorubicin, idarubicin, asparaginase, and antimetabolites, including, but not limited to, cytarabine, methotrexate, 5-fluorouracil decarbazine, 6-thioguanine, 6-mercaptopurine, and nelarabine. In some embodiments, the anti-CD100 antibody is administered prior to treatment with the chemotherapeutic agent. In alternative embodiments, the anti-CD100 antibody is administered after treatment with the chemotherapeutic agent. In yet other embodiments, the chemotherapeutic agent is administered simultaneously with the anti-CD100 antibody.

Thus, for example, in some embodiments, the anti-CD100 antibody is administered in combination with fludarabine or fludarabine phosphate. In one such embodiment, the anti-CD100 antibody is administered prior to administration of fludarabine or fludarabine phosphate. In alternative embodiments, the anti-CD100 antibody is administered after treatment with fludarabine or fludarabine phosphate. In yet other embodiments, the fludarabine or fludarabine phosphate is administered simultaneously with the anti-CD100 antibody.

In other embodiments of the invention, chlorambucil, an alkylating drug, is administered in combination with an anti-CD100 antibody described herein. In one such embodiment, the anti-CD100 antibody is administered prior to administration of chlorambucil. In alternative embodiments, the anti-CD100 antibody is administered after treatment with chlorambucil. In yet other embodiments, the chlorambucil is administered simultaneously with the anti-CD100 antibody.

In yet other embodiments, anthracycline-containing regimens such as CAP (cyclophosphamide, doxorubicin plus prednisone) and CHOP (cyclophosphamide, vincristine, prednisone plus doxorubicin) may be combined with administration of an anti-CD100 antibody described herein. In one such embodiment, the anti-CD100 antibody is administered prior to administration of anthracycline-containing regimens. In other embodiments, the anti-CD100 antibody is administered after treatment with anthracycline-containing regimens. In yet other embodiments, the anthracycline-containing regimen is administered simultaneously with the anti-CD100 antibody.

In alternative embodiments, an anti-CD100 antibody described herein is administered in combination with a small molecule-based cancer therapy, including, but not limited to, microtubule and/or topoisomerase inhibitors (for example, the mitotic inhibitor dolastatin and dolastatin analogues; the tubulin-binding agent T900607; XL119; and the topoisomerase inhibitor aminocamptothecin), SDX-105 (bendamustine hydrochloride), ixabepilone (an epothilone analog, also referred to as BMS-247550), protein kinase C inhibitors, for example, midostaurin ((PKC-412, CGP 41251, N-benzoylstaurosporine), pixantrone, eloxatin (an antineoplastic agent), ganite (gallium nitrate), Thalomid® (thalidomide), immunomodulatory derivatives of thalidomide (for example, revlimid (formerly revimid)), Affinitak™ (antisense inhibitor of protein kinase C-alpha), SDX-101 (R-etodolac, inducing apoptosis of malignant lymphocytes), second-generation purine nucleoside analogs such as clofarabine, inhibitors of production of the protein Bcl-2 by cancer cells (for example, the antisense agents oblimersen and Genasense®, proteasome inhibitors (for example, Velcade™ (bortezomib)), small molecule kinase inhibitors (for example, CHIR-258), small molecule VEGF inhibitors (for example, ZD-6474), small molecule inhibitors of heat shock protein (HSP) 90 (for example, 17-AAG), small molecule inhibitors of histone deacetylases (for example, hybrid/polar cytodifferentiation HPC) agents such as suberanilohydroxamic acid (SAHA), and FR-901228) and apoptotic agents such as Trisenox® (arsenic trioxide) and Xcytrin® (motexafin gadolinium). In one such embodiment, the anti-CD100 antibody is administered prior to administration of the small molecule-based cancer therapy. In other embodiments, the anti-CD100 antibody is administered after treatment with the small molecule-based cancer therapy. In yet other embodiments, the small molecule-based cancer therapy is administered simultaneously with the anti-CD100 antibody.

In yet other embodiments, an anti-CD100 antibody described herein can be used in combination with vaccine/immunotherapy-based cancer therapy, including, but not limited to, vaccine approaches (for example, Id-KLH, oncophage, vitalethine), personalized immunotherapy or active idiotype immunotherapy (for example, MyVax® Personalized Immunotherapy, formally designated GTOP-99), Promune® (CpG 7909, a synthetic agonist for toll-like receptor 9 (TLR9)), interferon-alpha therapy, interleukin-2 (IL-2) therapy, IL-12 therapy, IL-15 therapy, or IL-21 therapy; or steroid therapy. In one such embodiment, the anti-CD100 antibody is administered prior to administration of the vaccine/immunotherapy-based cancer therapy. In other embodiments, the anti-CD100 antibody is administered after treatment with the vaccine/immunotherapy-based cancer therapy. In yet other embodiments, the vaccine/immunotherapy-based cancer therapy is administered simultaneously with the anti-CD100 antibody.

The anti-CD100 antibodies of the invention can be used in combination with any known therapies for autoimmune and inflammatory diseases, including any agent or combination of agents that are known to be useful, or which have been used or are currently in use, for treatment of autoimmune and inflammatory diseases. Such therapies and therapeutic agents include, but are not limited to, surgery or surgical procedures (e.g., splenectomy, lymphadenectomy, thyroidectomy, plasmaphoresis, leukophoresis, cell, tissue, or organ transplantation, intestinal procedures, organ perfusion, and the like), radiation therapy, therapy such as steroid therapy and non-steroidal therapy, hormone therapy, cytokine therapy, therapy with dermatological agents (for example, topical agents used to treat skin conditions such as allergies, contact dermatitis, and psoriasis), immunosuppressive therapy, and other anti-inflammatory monoclonal antibody therapy, and the like. In this manner, the anti-CD100 antibodies described herein are administered in combination with at least one other therapy, including, but not limited to, surgery, organ perfusion, radiation therapy, steroid therapy, non-steroidal therapy, antibiotic therapy, antifungal therapy, hormone therapy, cytokine therapy, therapy with dermatological agents (for example, topical agents used to treat skin conditions such as allergies, contact dermatitis, and psoriasis), immunosuppressive therapy, other anti-inflammatory monoclonal antibody therapy, combinations thereof, and the like. Thus, where the combined therapies comprise administration of an anti-CD100 antibody in combination with administration of another therapeutic agent, as with steroids as one example, the methods of the invention encompass coadministration, using separate formulations or a single pharmaceutical formulation, and consecutive administration in either order.

Where the methods of the present invention comprise combined therapeutic regimens, these therapies can be given simultaneously, i.e., the anti-CD100 antibody is administered concurrently or within the same time frame as the other therapy (i.e., the therapies are going on concurrently, but the anti-CD100 antibody is not administered precisely at the same time as the other therapy). Alternatively, the anti-CD100 antibody of the present invention may also be administered prior to or subsequent to the other therapy. Sequential administration of the different therapies may be performed regardless of whether the treated subject responds to the first course of therapy to decrease the possibility of remission or relapse.

In some embodiments of the invention, the anti-CD100 antibodies described herein are administered in combination with immunosuppressive drugs or anti-inflammatory drugs, wherein the antibody and the therapeutic agent(s) may be administered sequentially, in either order, or simultaneously (i.e., concurrently or within the same time frame). Examples of suitable immunosuppressive drugs that can be administered in combination with the anti-CD100 antibodies of the invention include, but are not limited to, methotrexate, cyclophosphamide, mizoribine, chlorambucil, cyclosporine, such as, for example, aerosolized cyclosporine (see, U.S. Patent Application Publication No. US20020006901, herein incorporated by reference in its entirety), tacrolimus (FK506; Pro-Graf™), mycophenolate mofetil, and azathioprine (6-mercaptopurine), sirolimus (rapamycin), deoxyspergualin, leflunomide and its malononitriloamide analogs; and immunosuppressive proteins, including, for example, anti-CTLA4 antibodies and Ig fusions, anti-B lymphocyte stimulator antibodies (e.g., LYMPHOSTAT-B™) and Ig fusions (BLyS-Ig), anti-CD80 antibodies and etanercept (Enbrel™), as well as anti-T cell antibodies such as anti-CD3 (OKT3), anti-CD4, and the like. Examples of suitable anti-inflammatory agents include, but are not limited to, corticosteroids such as, for example, clobetasol, halobetasol, hydrocortisone, triamcinolone, betamethasone, fluocinole, fluocinonide, prednisone, prednisolone, methylprednisolone; non-steroidal anti-inflammatory drugs (NSAIDs) such as, for example, sulfasalazine, medications containing mesalamine (known as 5-ASA agents), celecoxib, diclofenac, etodolac, fenprofen, flurbiprofen, ibuprofen, ketoprofen, meclofamate, meloxicam, nabumetone, naproxen, oxaprozin, piroxicam, rofecoxib, salicylates, sulindac, and tolmetin; anti-inflammatory antibodies such as adalimumab (HUMIRA®, a TNF-α antagonist) and infliximab (Remicade®, a TNF-α antagonist), and the like.

Transplant rejection and graft versus host disease can be hyperacute (humoral), acute (T cell mediated), or chronic (unknown etiology), or a combination thereof. Thus, the anti-CD100 antibodies of the invention are used in some embodiments to prevent and/or ameliorate rejection and/or symptoms associated with hyperacute, acute, and/or chronic transplant rejection of any tissue, including, but not limited to, liver, kidney, pancreas, pancreatic islet cells, small intestine, lung, heart, corneas, skin, blood vessels, bone, heterologous or autologous bone marrow, and the like. Graft tissues may be obtained from any donor and transplanted into any recipient host, and thus the transplant procedure may comprise transplanting animal tissue to humans (e.g., xenografts), transplanting tissue from one human to another human (e.g., allografts), and/or transplanting tissue from one part of a human's body to another (e.g., autografts). Treatment with the antibodies of the invention may also reduce transplantation sequelae such as fever, anorexia, hemodynamic abnormalities, leukopenia, white cell infiltration of the transplanted organ/tissue, as well as opportunistic infections.

In some embodiments, the anti-CD100 antibodies of the invention may be used alone or in combination with immunosuppressive drugs to treat and/or prevent transplant rejection such as hyperacute, acute, and/or chronic rejection and/or graft versus host disease. Thus, in some embodiments where the anti-CD100 antibodies of the invention are used to treat graft rejection, the antibodies may used in combination with suitable immunosuppressive drugs, including, but not limited, to methotrexate; cyclophosphamide; mizoribine; chlorambucil; cyclosporine, such as, for example, aerosolized cyclosporine (see, U.S. Patent Application Publication No. US20020006901, herein incorporated by reference in its entirety), tacrolimus (FK506; ProGraf™), mycophenolate mofetil, and azathioprine (6-mercaptopurine), sirolimus (rapamycin), deoxyspergualin, leflunomide and its malononitriloamide analogs; and immunosuppressive proteins, including, for example, anti-CTLA antibodies and Ig fusions, anti-B lymphocyte stimulator antibodies (e.g., LYMPHOSTAT-B™) and Ig fusions (BLyS-Ig), anti-CD80 antibodies and etanercept (Enbrel®), as well as anti-T cell antibodies such as anti-CD3 (OKT3), anti-CD4, and the like.

As such, it is specifically contemplated that the compositions and methods of the invention are used in combination with other drugs to further improve symptoms and outcomes in transplant recipients, such as those receiving lung grafts, for example. Thus, in some embodiments, the anti-CD100 antibodies of the invention are used to treat transplant rejection (such as, for example hyperacute, acute, and/or chronic rejection or graft versus host disease in lung transplant recipients) alone or in combination with parenterally and/or non-parenterally administered cyclosporine, including for example oral cyclosporine, injectable cyclosporine, aerosolized (e.g., inhaled) cyclosporine, and combinations thereof. In some embodiments where at least a component of the therapy is aerosolized cyclosporine, the cyclosporine is delivered to the lung of the recipient by inhalation of cyclosporine in aerosol spray form using, for example, a pressurized delivery device or nebulizer. The cyclosporine may be administered in either dry powder or wet form.

In some other embodiments, the anti-CD100 antibodies of the invention may be used alone or in combination with immunosuppressive drugs to treat and/or prevent rheumatoid arthritis. Thus in some embodiments where the anti-CD100 antibodies of the invention are used to treat rheumatoid arthritis, the antibodies may used in combination with suitable immunosuppressive drugs, including, but not limited to, methotrexate, cyclophosphamide, mizoribine, chlorambucil, cyclosporine, tacrolimus (FK506; PROGRAF™), mycophenolate mofetil, and azathioprine (6-mercaptopurine), sirolimus (rapamycin), deoxyspergualin, leflunomide and its malononitriloamide analogs; and immunosuppressive proteins, including, for example, anti-CTLA antibodies and Ig fusions, anti-B lymphocyte stimulator antibodies (e.g., LYMPHOSTAT-B™) and Ig fusions (BLyS-Ig), other anti-CD100 antibodies (e.g., BD16 or BB18); anti-CD80 antibodies, and etanercept (ENBREL®), as well as anti-T cell antibodies such as anti-CD3 (OKT3), anti-CD4, and the like. As discussed above, treatment effectiveness may be assessed using any means and includes, but is not limited to, effectiveness as measured by clinical responses defined by the American College of Rheumatology criteria, the European League of Rheumatism criteria, or any other criteria. See for example, Felson et al. (1995) *Arthritis. Rheum.* 38:727-35 and van Gestel et al. (1996) *Arthritis Rheum.* 39:34-40.

In yet other embodiments, the anti-CD100 antibodies of the invention may be used alone or in combination with immunosuppressive drugs to treat and/or prevent multiple sclerosis. Thus in some embodiments where the anti-CD100 antibodies of the invention are used to treat multiple sclerosis, the antibodies may used in combination with suitable immunosuppressive drugs, including, but not limited to, methotrexate, cyclophosphamide, mizoribine, chlorambucil, cyclosporine, tacrolimus (FK506; PROGRAF™), mycophenolate mofetil, and azathioprine (6-mercaptopurine), sirolimus (rapamycin), deoxyspergualin, leflunomide and its malononitriloamide analogs; and immunosuppressive proteins, including, for example, anti-CTLA antibodies and Ig fusions, anti-B lymphocyte stimulator antibodies (e.g., LYMPHOSTAT-B™) and Ig fusions (BLyS-Ig), other anti-CD100 antibodies (e.g., BD16 or BB18); anti-CD80 antibodies, and etanercept (ENBREL®), as well as anti-T cell antibodies such as anti-CD3 (OKT3), anti-CD4, and the like.

Further, combination therapy with two or more therapeutic agents and an anti-CD100 antibody described herein can also be used for treatment of disease states associated with CD100-expressing cells, for example, T cell-related cancers, and autoimmune and/or inflammatory disorders. Without being limiting, examples include triple combination therapy, where two chemotherapeutic agents are administered in combination with an anti-CD100 antibody described herein, and where a chemotherapeutic agent and another anti-cancer monoclonal antibody (for example, alemtuzumab, rituximab, or anti-CD23 antibody) are administered in combination with an anti-CD100 antibody described herein. Examples of such combinations include, but are not limited to, combinations of fludarabine, cyclophosphamide, and the anti-CD100 antibody; and combinations of fludarabine, another anti-CD100 antibody, for example, BD16 or BB18, and an anti-CD100 antibody of the invention.

A further embodiment of the invention is the use of anti-CD100 antibodies for diagnostic monitoring of protein levels in tissue as part of a clinical testing procedure, e.g., to determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include $^{125}I$, $^{131}I$, $^{35}S$, or $^{3}H$.

VIII. Pharmaceutical Compositions and Administration Methods

Methods of preparing and administering the anti-CD100 antibodies, or antigen-binding fragments, variants, or derivatives thereof of the invention to a subject in need thereof are well known to or are readily determined by those skilled in the art. The route of administration of the anti-CD100 antibody, or antigen-binding fragment, variant, or derivative thereof may be, for example, oral, parenteral, by inhalation or topical. The term parenteral as used herein includes, e.g., intravenous, intraarterial, intraperitoneal, intramuscular, subcutaneous, rectal, or vaginal administration. While all these forms of administration are clearly contemplated as being within the scope of the invention, a form for administration would be a solution for injection, in particular for intravenous or intraarterial injection or drip. Usually, a suitable pharmaceutical composition for injection may comprise a buffer (e.g. acetate, phosphate or citrate buffer), a surfactant (e.g. polysorbate), optionally a stabilizer agent (e.g. human albumin), etc. However, in other methods compatible with the teachings herein, anti-CD100 antibodies, or antigen-binding fragments, variants, or derivatives thereof of the invention can be delivered directly to the site of the adverse cellular population thereby increasing the exposure of the diseased tissue to the therapeutic agent.

As previously discussed, anti-CD100 antibodies, or antigen-binding fragments, variants, or derivatives thereof, of the invention may be administered in a pharmaceutically effective amount for the in vivo treatment of CD100-expressing cell-mediated diseases such as certain types of lymphomas, autoimmune diseases, inflammatory diseases including central nervous system (CNS) and peripheral nervous system (PNS) inflammatory diseases, and invasive angiogenesis. In this regard, it will be appreciated that the disclosed antibodies will be formulated so as to facilitate administration and promote stability of the active agent. Preferably, pharmaceutical compositions in accordance with the present invention comprise a pharmaceutically acceptable, non-toxic, sterile carrier such as physiological saline, non-toxic buffers, preservatives and the like. For the purposes of the instant application, a pharmaceutically effective amount of an anti-CD100 antibody, or antigen-binding fragment, variant, or derivative thereof, conjugated or unconjugated, shall be held to mean an amount sufficient to achieve effective binding to a target and to achieve a benefit, e.g., to ameliorate symptoms of a disease or disorder or to detect a substance or a cell.

The pharmaceutical compositions used in this invention comprise pharmaceutically acceptable carriers, including, e.g., ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol, and wool fat.

Preparations for parenteral administration includes sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. In the subject invention, pharmaceutically acceptable carriers include, but are not limited to, 0.01-0.1 M and preferably 0.05 M phosphate buffer or 0.8% saline. Other common parenteral vehicles include sodium phosphate solutions, Ringer's dextrose, dextrose and sodium chloride, lactated Ringer's, or fixed oils. Intravenous vehicles include fluid and nutrient replenishers, electrolyte replenishers, such as those based on Ringer's dextrose, and the like. Preservatives and other additives may also be present such as for example, antimicrobials, antioxidants, chelating agents, and inert gases and the like.

More particularly, pharmaceutical compositions suitable for injectable use include sterile aqueous solutions (where water soluble) or dispersions and sterile powders for the extemporaneous preparation of sterile injectable solutions or dispersions. In such cases, the composition must be sterile and should be fluid to the extent that easy syringability exists. It should be stable under the conditions of manufacture and storage and will preferably be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Suitable formulations for use in the therapeutic methods disclosed herein are described in Remington's *Pharmaceutical Sciences* (Mack Publishing Co.) 16th ed. (1980).

Prevention of the action of microorganisms can be achieved by various antibacterial and antifungal agents, for example, parabens, chlorobutanol, phenol, ascorbic acid, thimerosal and the like. In many cases, it will be preferable to include isotonic agents, for example, sugars, polyalcohols, such as mannitol, sorbitol, or sodium chloride in the composition. Prolonged absorption of the injectable compositions can be brought about by including in the composition an agent which delays absorption, for example, aluminum monostearate and gelatin.

In any case, sterile injectable solutions can be prepared by incorporating an active compound (e.g., an anti-CD100 antibody, or antigen-binding fragment, variant, or derivative thereof, by itself or in combination with other active agents) in the required amount in an appropriate solvent with one or a combination of ingredients enumerated herein, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yields a powder of an active ingredient plus any additional desired ingredient from a previously sterile-filtered solution thereof. The preparations for injections are processed, filled into containers such as ampoules, bags, bottles, syringes or vials, and sealed under aseptic conditions according to methods known in the art. Further, the preparations may be packaged and sold in the form of a kit such as those described in U.S. patent application Ser. No. 09/259,337. Such articles of manufacture will preferably have labels or package inserts indicating that the associated compositions are useful for treating a subject suffering from, or predisposed to a disease or disorder.

Parenteral formulations may be a single bolus dose, an infusion or a loading bolus dose followed with a maintenance dose. These compositions may be administered at specific fixed or variable intervals, e.g., once a day, or on an "as needed" basis.

Certain pharmaceutical compositions used in this invention may be orally administered in an acceptable dosage form including, e.g., capsules, tablets, aqueous suspensions or solutions. Certain pharmaceutical compositions also may be administered by nasal aerosol or inhalation. Such compositions may be prepared as solutions in saline, employing benzyl alcohol or other suitable preservatives, absorption promoters to enhance bioavailability, and/or other conventional solubilizing or dispersing agents.

The amount of an anti-CD100 antibody, or fragment, variant, or derivative thereof that may be combined with the carrier materials to produce a single dosage form will vary depending upon the host treated and the particular mode of administration. The composition may be administered as a single dose, multiple doses or over an established period of time in an infusion. Dosage regimens also may be adjusted to provide the optimum desired response (e.g., a therapeutic or prophylactic response).

In keeping with the scope of the present disclosure, anti-CD100 antibodies, or antigen-binding fragments, variants, or derivatives thereof of the invention may be administered to a human or other animal in accordance with the aforementioned methods of treatment in an amount sufficient to produce a therapeutic effect. The anti-CD100 antibodies, or antigen-binding fragments, variants, or derivatives thereof of the invention can be administered to such human or other animal in a conventional dosage form prepared by combining the antibody of the invention with a conventional pharmaceutically acceptable carrier or diluent according to known techniques. It will be recognized by one of skill in the art that the form and character of the pharmaceutically acceptable carrier or diluent is dictated by the amount of active ingredient with which it is to be combined, the route of administration and other well-known variables. Those skilled in the art will further appreciate that a cocktail comprising one or more species of anti-CD100 antibodies, or antigen-binding fragments, variants, or derivatives thereof of the invention may prove to be particularly effective.

Effective doses of the compositions of the present invention, for treatment of CD100-expressing cell-mediated diseases such as certain types of lymphomas, autoimmune diseases, inflammatory diseases including central nervous system (CNS) and peripheral nervous system (PNS) inflammatory diseases, and invasive angiogenesis, vary depending upon many different factors, including means of administration, target site, physiological state of the patient, whether the patient is human or an animal, other medications administered, and whether treatment is prophylactic or therapeutic. Usually, the patient is a human, but non-human mammals including transgenic mammals can also be treated. Treatment dosages may be titrated using routine methods known to those of skill in the art to optimize safety and efficacy.

The amount of at least one anti-CD100 antibody to be administered is readily determined by one of ordinary skill in the art without undue experimentation given the disclosure of the present invention. Factors influencing the mode of administration and the respective amount of at least one anti-CD100 antibody, antigen-binding fragment, variant or derivative thereof include, but are not limited to, the severity of the disease, the history of the disease, and the age, height, weight, health, and physical condition of the individual undergoing therapy. Similarly, the amount of anti-CD100 antibody, or fragment, variant, or derivative thereof to be administered will be dependent upon the mode of administration and whether the subject will undergo a single dose or multiple doses of this agent. The dose of anti-CD100 antibody, or fragment, or variant, or derivative thereof to be administered is in the range from about 0.0001 to 100 mg/kg, 0.003 mg/kg to about 50 mg/kg, or about 0.01 mg/kg to about 40 mg/kg. Thus, for example, the dose can be 0.01 mg/kg, 0.03 mg/kg, 0.1 mg/kg, 0.3 mg/kg, 0.5 mg/kg, 1 mg/kg, 1.5 mg/kg, 2 mg/kg, 2.5 mg/kg, 3 mg/kg, 5 mg/kg, 7 mg/kg, 10 mg/kg, 15 mg/kg, 20 mg/kg, 25 mg/kg, 30 mg/kg, 35 mg/kg, 40 mg/kg, 45 mg/kg, 50 mg/kg, 60 mg/kg, 70 mg/kg, 80 mg/kg, 90 mg/kg, or 100 mg/kg.

In some embodiments, for treatment of CD100-expressing cell-mediated diseases such as certain types of lymphomas, autoimmune diseases, inflammatory diseases including central nervous system (CNS) and peripheral nervous system (PNS) inflammatory diseases, and invasive angiogenesis with an anti-CD100 antibody, or antigen-binding fragment, variant, or derivative thereof, the dosage can range, e.g., from about 0.0001 to 100 mg/kg, and more usually 0.01 to 5 mg/kg (e.g., 0.02 mg/kg, 0.25 mg/kg, 0.5 mg/kg, 0.75 mg/kg, 1 mg/kg, 2 mg/kg, etc.), of the host body weight. For example dosages can be 1 mg/kg body weight or 10 mg/kg body weight or within the range of 1-10 mg/kg, preferably at least 1 mg/kg. Doses intermediate in the above ranges are also intended to be within the scope of the invention. Subjects can be administered such doses daily, on alternative days, weekly or according to any other schedule determined by empirical analysis. Exemplary dosage schedules include 1-10 mg/kg or 15 mg/kg on consecutive days, 30 mg/kg on alternate days, or 60 mg/kg weekly. In some methods, two or more monoclonal antibodies with different binding specificities are administered simultaneously, in which case the dosage of each antibody administered falls within the ranges indicated.

Anti-CD100 antibodies, or antigen-binding fragments, variants, or derivatives thereof of the invention can be administered on multiple occasions. Intervals between single dosages can be daily, weekly, monthly or yearly. Intervals can also be irregular as indicated by measuring blood levels of target polypeptide or target molecule in the patient. In some methods, dosage is adjusted to achieve a plasma polypeptide concentration of 1-1000 µg/ml and in some methods 25-300 µg/ml. Alternatively, anti-CD100 antibodies, or antigen-binding fragments, variants, or derivatives thereof of the invention can be administered as a sustained release formulation, in which case less frequent administration is required. Dosage and frequency vary depending on the half-life of the antibody in the patient. The half-life of an anti-CD100 antibody can also be prolonged via fusion to a stable polypeptide or moeity, e.g., albumin or PEG. In general, humanized antibodies show the longest half-life, followed by chimeric antibodies and nonhuman antibodies. In one embodiment, the anti-CD100 antibodies, or antigen-binding fragments, variants, or derivatives thereof of the invention can be administered in unconjugated form. In another embodiment, the anti-CD100 antibodies, or antigen-binding fragments, variants, or derivatives thereof of the invention can be administered multiple times in conjugated form. In still another embodiment, anti-CD100 antibodies, or antigen-binding fragments, variants, or derivatives thereof of the invention can be administered in unconjugated form, then in conjugated form, or vice versa.

In another embodiment of the invention, the method comprises administration of multiple doses of anti-CD100 antibody, or antigen-binding fragment, variant, or derivative thereof. The method may comprise administration of 1, 2, 3, 4, 5, 6, 7, 8, 9, 10, 15, 20, 25, 30, 35, 40, or more therapeutically effective doses of a pharmaceutical composition comprising an anti-CD100 antibody, fragment, variant, or derivative thereof. The frequency and duration of administration of multiple doses of the pharmaceutical compositions comprising the antibody molecule can be readily determined by one of skill in the art without undue experimentation given the disclosure herein. Moreover, treatment of a subject with a therapeutically effective amount of an antibody can include a single treatment or, preferably, can include a series of treatments. In a preferred example, a subject is treated with anti-CD100 antibody, or antigen-binding fragment, variant, or derivative thereof in the range of between about 0.1 to 20 mg/kg body weight, once per week for between about 1 to 10 weeks, preferably between about 2 to 8 weeks, more preferably between about 3 to 7 weeks, and even more preferably for about 4, 5, or 6 weeks. Treatment may occur annually to prevent relapse or upon indication of relapse. It will also be appreciated that the effective dosage of antibody molecule used for treatment may increase or decrease over the course of a particular treatment. Changes in dosage may result and become apparent from the results of diagnostic assays as described herein.

Thus, in one embodiment, the dosing regimen includes a first administration of a therapeutically effective dose of at least one anti-CD100 antibody, or antigen-binding fragment, variant, or derivative thereof, on days 1, 7, 14, and 21 of a treatment period. In another embodiment, the dosing regimen includes a first administration of a therapeutically effective dose of at least one anti-CD100 antibody, or antigen-binding fragment, variant, or derivative thereof, on days 1, 2, 3, 4, 5, 6, and 7 of a week in a treatment period. Further embodiments include a dosing regimen having a first administration of a therapeutically effective dose of at least one anti-CD100 antibody, or antigen-binding fragment, variant, or derivative thereof, on days 1, 3, 5, and 7 of a week in a treatment period; a dosing regimen including a first administration of a therapeutically effective dose of at least one anti-CD100 antibody, or antigen-binding fragment, variant, or derivative thereof, on days 1 and 3 of a week in a treatment period; and a preferred dosing regimen including a first administration of a therapeutically effective dose of at least one anti-CD100 antibody, or antigen-binding fragment, variant, or derivative thereof, on day 1 of a week in a treatment period. The treatment period may comprise 1 week, 2 weeks, 3 weeks, a month, 3 months, 6 months, or a year. Treatment periods may be subsequent or separated from each other by a day, a week, 2 weeks, a month, 3 months, 6 months, or a year.

In some embodiments, the therapeutically effective doses of anti-CD100 antibody, or antigen-binding fragment, variant, or derivative thereof, ranges from about 0.0001 mg/kg to about 100 mg/kg, from about 0.003 mg/kg to about 50 mg/kg, from about 0.01 mg/kg to about 40 mg/kg, from about 0.01 mg/kg to about 30 mg/kg, from about 0.1 mg/kg to about 30 mg/kg, from about 0.5 mg/kg to about 30 mg/kg, from about 1 mg/kg to about 30 mg/kg, from about 3 mg/kg to about 30 mg/kg, from about 3 mg/kg to about 25 mg/kg, from about 3 mg/kg to about 20 mg/kg, from about 5 mg/kg to about 15 mg/kg, or from about 7 mg/kg to about 12 mg/kg. Thus, for example, the dose of any one anti-CD100 antibody, or antigen-binding fragment, variant, or derivative thereof, can be 0.003 mg/kg, 0.01 mg/kg, 0.03 mg/kg, 0.1 mg/kg, 0.3 mg/kg, 0.5 mg/kg, 1 mg/kg, 1.5 mg/kg, 2 mg/kg, 2.5 mg/kg, 3 mg/kg, 5 mg/kg, 7 mg/kg, 10 mg/kg, 15 mg/kg, 20 mg/kg, 25 mg/kg, 30 mg/kg, 35 mg/kg, 40 mg/kg, 45 mg/kg, 50 mg/kg, or other such doses falling within the range of about 0.0001 mg/kg to about 100 mg/kg. The same therapeutically effective dose of an anti-CD100 antibody, or antigen-binding fragment, variant, or derivative thereof, can be administered throughout each week of antibody dosing. Alternatively, different therapeutically effective doses of an anti-CD100 antibody, or antigen-binding fragment, variant, or derivative thereof, can be used over the course of a treatment period.

IX. Use of Anti-CD100 Antibodies in the Manufacture of Medicaments

The present invention also provides for the use of an anti-CD100 antibody or antigen-binding fragment, variant, or derivative thereof in the manufacture of a medicament for treating an autoimmune disease and/or inflammatory disease in a subject, including CNS and PNS inflammatory diseases, wherein the medicament is coordinated with treatment with at least one other therapy. By "coordinated" is intended the medicament is to be used either prior to, during, or after treatment of the subject with at least one other therapy for the autoimmune disease and/or inflammatory disease. Examples of other therapies include, but are not limited to, those described herein above, i.e., surgery or surgical procedures (e.g. splenectomy, lymphadenectomy, thyroidectomy, plasmaphoresis, leukophoresis, cell, tissue, or organ transplantation, organ perfusion, intestinal procedures, and the like), radiation therapy, therapy such as steroid therapy and non-steroidal therapy, hormone therapy, cytokine therapy, therapy with dermatological agents (for example, topical agents used to treat skin conditions such as allergies, contact dermatitis, and psoriasis), immunosuppressive therapy, and other anti-inflammatory monoclonal antibody therapy, and the like, where treatment with the additional therapy, or additional therapies, occurs prior to, during, or subsequent to treatment of the subject with the medicament comprising the anti-CD100 antibody or antigen-binding fragment, variant, or derivative thereof, as noted herein above. In one such embodiment, the present invention provides for the use of the monoclonal antibodies of the invention, or antigen-binding fragment, variant, or derivative thereof, in the manufacture of a medicament for treating an autoimmune disease and/or inflammatory disease in a subject, wherein the medicament is coordinated with treatment with at least one other therapy as noted herein above.

"Treatment" in the context of coordinated use of a medicament described herein with one or more other autoimmune disease and/or inflammatory disease therapies is herein defined as the application or administration of the medicament or of the other therapy to a subject, or application or administration of the medicament or other therapy to an isolated tissue or cell line from a subject, where the subject has an autoimmune disease and/or inflammatory disease associated with CD100-expressing cells, a symptom associated with such a disease, or a predisposition toward development of such a disease, where the purpose is to cure, heal, alleviate, relieve, alter, remedy, ameliorate, improve, or affect the disease, any associated symptoms of the disease, or the predisposition toward the development of the disease.

The present invention also provides for the use of an anti-CD100 antibody or antigen-binding fragment, variant, or derivative thereof in the manufacture of a medicament for treating a subject for certain types of cancer, wherein the medicament is coordinated with treatment with at least one other cancer therapy. Cancers characterized by neoplastic B cell growth include, but are not limited to, the B cell-related cancers discussed herein above, for example, non-Hodgkin's lymphoma, chronic lymphocytic leukemia, multiple myeloma, B cell lymphoma, high-grade B cell lymphoma, intermediate-grade B cell lymphoma, low-grade B cell lymphoma, B cell acute lympohoblastic leukemia, myeloblastic leukemia, Hodgkin's disease, plasmacytoma, follicular lymphoma, follicular small cleaved lymphoma, follicular large cell lymphoma, follicular mixed small cleaved lymphoma, diffuse small cleaved cell lymphoma, diffuse small lymphocytic lymphoma, prolymphocytic leukemia, lymphoplasmacytic lymphoma, marginal zone lymphoma, mucosal associated lymphoid tissue lymphoma, monocytoid B cell lymphoma, splenic lymphoma, hairy cell leukemia, diffuse large cell lymphoma, mediastinal large B cell lymphoma, lymphomatoid granulomatosis, intravascular lymphomatosis, diffuse mixed cell lymphoma, diffuse large cell lymphoma, immunoblastic lymphoma, Burkitt's lymphoma, AIDS-related lymphoma, and mantle cell lymphoma. Cancers characterized by neoplastic T cell growth include, but are not limited to, the T cell-related cancers discussed herein above, for example, T cell prolymphocytic leukemia, T cell large granular lymphocytic leukemia, aggressive NK cell leukemia, adult T cell leukemia/lymphoma, extranodal NK/T cell lymphoma, enteropathy-type T cell lymphoma, hepatosplenic T cell lymphoma, blastic NK cell lymphoma, mycosis fungoides/Sezary syndrome, primary cutaneous CD30-positive T cell lymphoproliferative disorders (including primary cutaneous anaplastic large cell lymphoma and lymphomatoid papulosis), angioimmunoblastic T cell lymphoma, peripheral T cell lymphoma, and anaplastic large cell lymphoma.

By "coordinated" is intended the medicament comprising the anti-CD100 antibody or antigen-binding fragment, variant, or derivative thereof is to be used either prior to, during, or after treatment of the subject with at least one other cancer therapy. Examples of other cancer therapies include, but are not limited to, surgery; radiation therapy; chemotherapy, optionally in combination with autologous bone marrow transplant, where suitable chemotherapeutic agents include, but are not limited to, fludarabine or fludarabine phosphate, chlorambucil, vincristine, pentostatin, 2-chlorodeoxyadenosine (cladribine), cyclophosphamide, doxorubicin, prednisone, and combinations thereof, for example, anthracycline-containing regimens such as CAP (cyclophosphamide, doxorubicin plus prednisone), CHOP (cyclophosphamide, vincristine, prednisone plus doxorubicin), VAD (vincritsine, doxorubicin, plus dexamethasone), MP (melphalan plus prednisone), and other cytotoxic and/or therapeutic agents used in chemotherapy such as mitoxantrone, daunorubicin, idarubicin, asparaginase, and antimetabolites, including, but not limited to, cytarabine, methotrexate, 5-fluorouracil decarbazine, 6-thioguanine, 6-mercaptopurine, and nelarabine; other anti-cancer monoclonal antibody therapy (for example, alemtuzumab (Campath™) or other anti-CD52 antibody targeting the CD52 cell-surface glycoprotein on malignant B cells; rituximab (Rituxan™), the fully human antibody HuMax-CD20, R-1594, IMMU-106, TRU-015, AME-133, tositumomab/1-131 tositumomab (Bexxar®), ibritumomab tiuxetan (Zevalin®), or any other therapeutic anti-CD20 antibody targeting the CD20 antigen on malignant B cells; anti-CD19 antibody (for example, MT103, a bispecific antibody); anti-CD22 antibody (for example, the humanized monoclonal antibody epratuzumab); bevacizumab (Avastin®) or other anti-cancer antibody targeting human vascular endothelial growth factor; anti-CD22 antibody targeting the CD22 antigen on malignant B cells (for example, the monoclonal antibody BL-22, an alphaCD22 toxin); α-M-CSF antibody targeting macrophage colony stimulating factor; antibodies targeting the receptor activator of nuclear factor-kappaB (RANK) and its ligand (RANKL), which are overexpressed in multiple myeloma; anti-CD23 antibody targeting the CD23 antigen on malignant B cells (for example, IDEC-152); anti-CD38 antibody targeting the CD38 antigen on malignant B cells; antibodies targeting major histocompatibility complex class II receptors (anti-MHC antibodies) expressed on malignant B cells; anti-CD40 antibodies (for example, SGN-40) targeting the CD40 antigen on malignant B cells; and antibodies targeting tumor necrosis factor-related apoptosis-inducing ligand receptor 1 (TRAIL-R1) (for example, the agonistic human monoclonal antibody HGS-ETR1) expressed on a number of solid tumors and tumors of hematopoietic origin); small molecule-based cancer therapy, including, but not limited to, microtubule and/or topoisomerase inhibitors (for example, the mitotic inhibitor dolastatin and dolastatin analogues; the tubulin-binding agent T900607; XL119; and the topoisomerase inhibitor aminocamptothecin), SDX-105 (bendamustine hydrochloride), ixabepilone (an epothilone analog, also referred to as BMS-247550), protein kinase C inhibitors, for example, midostaurin ((PKC-412, CGP 41251, N-benzoylstaurosporine), pixantrone, eloxatin (an antineoplastic agent), ganite (gallium nitrate), Thalomid® (thalidomide), immunomodulatory derivatives of thalidomide (for example, revlimid (formerly revimid)), Affinitak™ (antisense inhibitor of protein kinase C-alpha), SDX-101 (R-etodolac, inducing apoptosis of malignant lymphocytes), second-generation purine nucleoside analogs such as clofarabine, inhibitors of production of the protein Bcl-2 by cancer cells (for example, the antisense agents oblimersen and Genasense®), proteasome inhibitors (for example, Velcade™ (bortezomib)), small molecule kinase inhibitors (for example, CHIR-258), small molecule VEGF inhibitors (for example, ZD-6474), small molecule inhibitors of heat shock protein (HSP) 90 (for example, 17-AAG), small molecule inhibitors of histone deacetylases (for example, hybrid/polar cytodifferentiation HPC) agents such as suberanilohydroxamic acid (SAHA), and FR-901228) and apoptotic agents such as Trisenox® (arsenic trioxide) and Xcytrin® (motexafin gadolinium); vaccine/immunotherapy-based cancer therapies, including, but not limited to, vaccine approaches (for example, Id-KLH, oncophage, vitalethine), personalized immunotherapy or active idiotype immunotherapy (for example, MyVax® Personalized Immunotherapy, formally designated GTOP-99), Promune®(CpG 7909, a synthetic agonist for toll-like receptor 9 (TLR9)), interferon-alpha therapy, interleukin-2 (IL-2) therapy, IL-12 therapy; IL-15 therapy, and IL-21 therapy; steroid therapy; or other cancer therapy; where treatment with the additional cancer therapy, or additional cancer therapies, occurs prior to, during, or subsequent to treatment of the subject with the medicament comprising the anti-CD100 antibody or antigen-binding fragment, variant, or derivative thereof, as noted herein above.

In some embodiments, the present invention provides for the use of the anti-CD100 antibody or antigen-binding fragment, variant, or derivative thereof in the manufacture of a medicament for treating a lymphoma, for example non-Hodgkin's lymphoma, in a subject, wherein the medicament is coordinated with treatment with at least one other cancer therapy selected from the group consisting of chemotherapy, anti-cancer antibody therapy, small molecule-based cancer therapy, and vaccine/immunotherapy-based cancer therapy, wherein the medicament is to be used either prior to, during, or after treatment of the subject with the other cancer therapy or, in the case of multiple combination therapies, either prior to, during, or after treatment of the subject with the other cancer therapies.

Thus, for example, in some embodiments, the invention provides for the use of the monoclonal anti-CD100 antibodies of the invention, or antigen-binding fragment, variant, or derivative thereof, in the manufacture of a medicament for treating a lymphoma, for example, non-Hodgkin's lymphoma, in a subject, wherein the medicament is coordinated with treatment with chemotherapy, where the chemotherapeutic agent is selected from the group consisting of cytoxan, doxorubicin, vincristine, prednisone, and combinations thereof, for example CHOP. In other embodiments, the invention provides for the use of the monoclonal antibody 1589, or antigen-binding fragment thereof, in the manufacture of a medicament for treating a lymphoma, for example non-Hodgkin's lymphoma, in a subject, wherein the medicament is coordinated with treatment with at least one other anti-cancer antibody selected from the group consisting of alemtuzumab (Campath™) or other anti-CD52 antibody targeting the CD52 cell-surface glycoprotein on malignant B cells; rituximab (Rituxan®), the fully human antibody HuMax-CD20, R-1594, IMMU-106, TRU-015, AME-133, tositumomab/1-131 tositumomab (Bexxar®), ibritumomab tiuxetan (Zevalin®), or any other therapeutic anti-CD20 antibody targeting the CD20 antigen on malignant B cells; anti-CD19 antibody (for example, MT103, a bispecific antibody); anti-CD22 antibody (for example, the humanized monoclonal antibody epratuzumab); bevacizumab (Avastin®) or other anti-cancer antibody targeting human vascular endothelial growth factor; and any combinations thereof, wherein the medicament is to be used either prior to, during, or after treatment of the subject with the other cancer therapy or, in the case of multiple combination therapies, either prior to, during, or after treatment of the subject with the other cancer therapies.

In yet other embodiments, the present invention provides for the use of the monoclonal antibodies of the invention, or antigen-binding fragment, variant, or derivative thereof, in the manufacture of a medicament for treating a lymphoma, for example non-Hodgkin's lymphoma, in a subject, wherein the medicament is coordinated with treatment with at least one other small molecule-based cancer therapy selected from the group consisting of microtubule and/or topoisomerase inhibitors (for example, the mitotic inhibitor dolastatin and dolastatin analogues; the tubulin-binding agent T900607; XL119; and the topoisomerase inhibitor aminocamptothecin), SDX-105 (bendamustine hydrochloride), ixabepilone (an epothilone analog, also referred to as BMS-247550), protein kinase C inhibitors, for example, midostaurin ((PKC-412, CGP 41251, N-benzoylstaurosporine), pixantrone, eloxatin (an antineoplastic agent), ganite (gallium nitrate), Thalomid® (thalidomide), an apoptotic agent such as Xcytrin® (motexafin gadolinium), inhibitors of production of the protein Bcl-2 by cancer cells (for example, the antisense agents oblimersen and Genasense®, nelarabine, and any combinations thereof; wherein the medicament is to be used either prior to, during, or after treatment of the subject with the other cancer therapy or, in the case of multiple combination therapies, either prior to, during, or after treatment of the subject with the other cancer therapies.

In still other embodiments, the present invention provides for the use of the monoclonal antibodies of the invention, or antigen-binding fragment, variant, or derivative thereof, in the manufacture of a medicament for treating a lymphoma, for example non-Hodgkin's lymphoma, in a subject, wherein the medicament is coordinated with treatment with at least one other vaccine/immunotherapy-based cancer therapy selected from the group consisting of vaccine approaches (for example, Id-KLH, oncophage, vitalethine), personalized immunotherapy or active idiotype immunotherapy (for example, MyVax® Personalized Immunotherapy, formally designated GTOP-99), Promune® (CpG 7909, a synthetic agonist for toll-like receptor 9 (TLR9)), interleukin-2 (IL-2) therapy, IL-12 therapy; IL-15 therapy, and IL-21 therapy, and any combinations thereof; wherein the medicament is to be used either prior to, during, or after treatment of the subject with the other cancer therapy or, in the case of multiple combination therapies, either prior to, during, or after treatment of the subject with the other cancer therapies.

In some embodiments, the present invention provides for the use of the anti-CD100 antibody of the invention, or antigen-binding fragment, variant, or derivative thereof, in the manufacture of a medicament for treating a leukemia in a subject, wherein the medicament is coordinated with treatment with at least one other cancer therapy selected from the group consisting of chemotherapy and anti-metabolite therapy, wherein the medicament is to be used either prior to, during, or after treatment of the subject with the other cancer therapy or, in the case of multiple combination therapies, either prior to, during, or after treatment of the subject with the other cancer therapies. Examples of such embodiments include, but are not limited to, those instances where the medicament comprising the anti-CD100 antibody, or antigen-binding fragment, variant, or derivative thereof, is coordinated with treatment with a chemotherapeutic agent or antimetabolite selected from the group consisting of cytoxan, doxorubicin, vincristine, prednisone, cytarabine, mitoxantrone, idarubicin, asparaginase, methotrexate, 6-thioguanine, 6-mercaptopurine, and combinations thereof, wherein the medicament is to be used either prior to, during, or after treatment of the subject with the other cancer therapy or, in the case of multiple combination therapies, either prior to, during, or after treatment of the subject with the other cancer therapies. In one such example, the medicament is coordinated with treatment with cytarabine plus daunorubicin, cytarabine plus mitoxantrone, and/or cytarabine plus idarubicin; wherein the medicament is to be used either prior to, during, or after treatment of the subject with the other cancer therapy or, in the case of multiple combination therapies, either prior to, during, or after treatment of the subject with the other cancer therapies.

The invention also provides for the use of an anti-CD100 antibody of the invention, or antigen-binding fragment, variant, or derivative thereof, in the manufacture of a medicament for treating a subject for a cancer characterized by neoplastic B or T cell growth, including the B or T cell-related cancers described herein above, wherein the medicament is used in a subject that has been pretreated with at least one other cancer therapy. By "pretreated" or "pretreatment" is intended the subject has received one or more other cancer therapies (i.e., been treated with at least one other cancer therapy) prior to receiving the medicament comprising the anti-CD100 antibody or antigen-binding fragment, variant, or derivative thereof. "Pretreated" or "pretreatment" includes subjects that have been treated with at least one other cancer therapy within 2 years, within 18 months, within 1 year, within 6 months, within 2 months, within 6 weeks, within 1 month, within 4 weeks, within 3 weeks, within 2 weeks, within 1 week, within 6 days, within 5 days, within 4 days, within 3 days, within 2 days, or even within 1 day prior to initiation of treatment with the medicament comprising the anti-CD100 antibody, for example, the monoclonal antibody 1589 disclosed herein, or antigen-binding fragment, variant, or derivative thereof. It is not necessary that the subject was a responder to pretreatment with the prior cancer therapy, or prior cancer therapies. Thus, the subject that receives the medicament comprising the anti-CD100 antibody or antigen-binding fragment, variant, or derivative thereof could have responded, or could have failed to respond (i.e., the cancer was refractory), to pretreatment with the prior cancer therapy, or to one or more of the prior cancer therapies where pretreatment comprised multiple cancer therapies. Examples of other cancer therapies for which a subject can have received pretreatment prior to receiving the medicament comprising the anti-CD100 antibody or antigen-binding fragment, variant, or derivative thereof include, but are not limited to, surgery; radiation therapy; chemotherapy, optionally in combination with autologous bone marrow transplant, where suitable chemotherapeutic agents include, but are not limited to, those listed herein above; other anti-cancer monoclonal antibody therapy, including, but not limited to, those anti-cancer antibodies listed herein above; small molecule-based cancer therapy, including, but not limited to, the small molecules listed herein above; vaccine/immunotherapy-based cancer therapies, including, but limited to, those listed herein above; steroid therapy; other cancer therapy; or any combination thereof.

"Treatment" in the context of coordinated use of a medicament described herein with one or more other cancer therapies is herein defined as the application or administration of the medicament or of the other cancer therapy to a subject, or application or administration of the medicament or other cancer therapy to an isolated tissue or cell line from a subject, where the subject has a cancer characterized by neoplastic B cell growth, a symptom associated with such a cancer, or a predisposition toward development of such a cancer, where the purpose is to cure, heal, alleviate, relieve, alter, remedy, ameliorate, improve, or affect the cancer, any associated symptoms of the cancer, or the predisposition toward the development of the cancer.

In some embodiments, the medicament comprising the anti-CD100 antibody, or antigen-binding fragment, variant, or derivative thereof, is coordinated with treatment with two other therapies. Where the medicament comprising the anti-CD100 antibody is coordinated with two other therapies, use of the medicament can be prior to, during, or after treatment of the subject with either or both of the other therapies.

The invention also provides for the use of an anti-CD100 antibody of the invention, or antigen-binding fragment, variant, or derivative thereof, in the manufacture of a medicament for treating an autoimmune disease and/or inflammatory disease in a subject, wherein the medicament is used in a subject that has been pretreated with at least one other therapy. By "pretreated" or "pretreatment" is intended the subject has been treated with one or more other therapies prior to receiving the medicament comprising the anti-CD100 antibody or antigen-binding fragment, variant, or derivative thereof. "Pretreated" or "pretreatment" includes subjects that have been treated with the other therapy, or other therapies, within 2 years, within 18 months, within 1 year, within 6 months, within 2 months, within 6 weeks, within 1 month, within 4 weeks, within 3 weeks, within 2 weeks, within 1 week, within 6 days, within 5 days, within 4 days, within 3 days, within 2 days, or even within 1 day prior to initiation of treatment with the medicament comprising the anti-CD100 antibody of the invention, or antigen-binding fragment, variant, or derivative thereof. It is not necessary that the subject was a responder to pretreatment with the prior therapy, or prior therapies. Thus, the subject that receives the medicament comprising the anti-CD100 antibody or antigen-binding fragment, variant, or derivative thereof could have responded, or could have failed to respond, to pretreatment with the prior therapy, or to one or more of the prior therapies where pretreatment comprised multiple therapies.

X. Diagnostics

The invention further provides a diagnostic method useful during diagnosis of CD100-expressing cell-mediated diseases such as certain types of lymphomas, autoimmune diseases, inflammatory diseases including central nervous system (CNS) and peripheral nervous system (PNS) inflammatory diseases, and invasive angiogenesis, which involves measuring the expression level of CD100 protein or transcript in tissue or other cells or body fluid from an individual and comparing the measured expression level with a standard CD100 expression level in normal tissue or body fluid, whereby an increase in the expression level compared to the standard is indicative of a disorder.

The anti-CD100 antibodies of the invention and antigen-binding fragments, variants, and derivatives thereof, can be used to assay CD100 protein levels in a biological sample using classical immunohistological methods known to those of skill in the art (e.g., see Jalkanen, et al. (1985) *J. Cell. Biol.* 101:976-985; Jalkanen et al. (1987) *J. Cell Biol.* 105:3087-3096). Other antibody-based methods useful for detecting CD100 protein expression include immunoassays, such as the enzyme linked immunosorbent assay (ELISA), immunoprecipitation, or Western blotting. Suitable assays are described in more detail elsewhere herein.

By "assaying the expression level of CD100 polypeptide" is intended qualitatively or quantitatively measuring or estimating the level of CD100 polypeptide in a first biological sample either directly (e.g., by determining or estimating absolute protein level) or relatively (e.g., by comparing to the disease associated polypeptide level in a second biological sample). Preferably, CD100 polypeptide expression level in the first biological sample is measured or estimated and compared to a standard CD100 polypeptide level, the standard being taken from a second biological sample obtained from an individual not having the disorder or being determined by averaging levels from a population of individuals not having the disorder. As will be appreciated in the art, once the "standard" CD100 polypeptide level is known, it can be used repeatedly as a standard for comparison.

By "biological sample" is intended any biological sample obtained from an individual, cell line, tissue culture, or other source of cells potentially expressing CD100. Methods for obtaining tissue biopsies and body fluids from mammals are well known in the art.

XI. Immunoassays

Anti-CD100 antibodies, or antigen-binding fragments, variants, or derivatives thereof of the invention may be assayed for immunospecific binding by any method known in the art. The immunoassays that can be used include but are not limited to competitive and non-competitive assay systems using techniques such as Western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well known in the art (see, e.g., Ausubel et al., eds, (1994) *Current Protocols in Molecular Biology* (John Wiley & Sons, Inc., NY) Vol. 1, which is incorporated by reference herein in its entirety). Exemplary immunoassays are described briefly below (but are not intended by way of limitation).

Immunoprecipitation protocols generally comprise lysing a population of cells in a lysis buffer such as RIPA buffer (1% NP-40 or Triton X-100, 1% sodium deoxycholate, 0.1% SDS, 0.15 M NaCl, 0.01 M sodium phosphate at pH 7.2, 1% Trasylol) supplemented with protein phosphatase and/or protease inhibitors (e.g., EDTA, PMSF, aprotinin, sodium vanadate), adding the antibody of interest to the cell lysate, incubating for a period of time (e.g., 1-4 hours) at 4° C., adding protein A and/or protein G sepharose beads to the cell lysate, incubating for about an hour or more at 4° C., washing the beads in lysis buffer and resuspending the beads in SDS/sample buffer. The ability of the antibody of interest to immunoprecipitate a particular antigen can be assessed by, e.g., western blot analysis. One of skill in the art would be knowledgeable as to the parameters that can be modified to increase the binding of the antibody to an antigen and decrease the background (e.g., pre-clearing the cell lysate with sepharose beads). For further discussion regarding immunoprecipitation protocols see, e.g., Ausubel et al., eds, (1994) *Current Protocols in Molecular Biology* (John Wiley & Sons, Inc., NY) Vol. 1 at 10.16.1.

Western blot analysis generally comprises preparing protein samples, electrophoresis of the protein samples in a polyacrylamide gel (e.g., 8%-20% SDS-PAGE depending on the molecular weight of the antigen), transferring the protein sample from the polyacrylamide gel to a membrane such as nitrocellulose, PVDF or nylon, blocking the membrane in blocking solution (e.g., PBS with 3% BSA or non-fat milk), washing the membrane in washing buffer (e.g., PBS-Tween 20), blocking the membrane with primary antibody (the antibody of interest) diluted in blocking buffer, washing the membrane in washing buffer, blocking the membrane with a secondary antibody (which recognizes the primary antibody, e.g., an anti-human antibody) conjugated to an enzymatic substrate (e.g., horseradish peroxidase or alkaline phosphatase) or radioactive molecule (e.g., $^{32}$P or $^{125}$I) diluted in blocking buffer, washing the membrane in wash buffer, and detecting the presence of the antigen. One of skill in the art would be knowledgeable as to the parameters that can be modified to increase the signal detected and to reduce the background noise. For further discussion regarding western blot protocols see, e.g., Ausubel et al., eds, (1994) *Current Protocols in Molecular Biology* (John Wiley & Sons, Inc., NY) Vol. 1 at 10.8.1.

ELISAs comprise preparing antigen, coating the well of a 96-well microtiter plate with the antigen, adding the antibody of interest conjugated to a detectable compound such as an enzymatic substrate (e.g., horseradish peroxidase or alkaline phosphatase) to the well and incubating for a period of time, and detecting the presence of the antigen. In ELISAs the antibody of interest does not have to be conjugated to a detectable compound; instead, a second antibody (which recognizes the antibody of interest) conjugated to a detectable compound may be added to the well. Further, instead of coating the well with the antigen, the antibody may be coated to the well. In this case, a second antibody conjugated to a detectable compound may be added following the addition of the antigen of interest to the coated well. One of skill in the art would be knowledgeable as to the parameters that can be modified to increase the signal detected as well as other variations of ELISAs known in the art. For further discussion regarding ELISAs see, e.g., Ausubel et al., eds, (1994) *Current Protocols in Molecular Biology* (John Wiley & Sons, Inc., NY) Vol. 1 at 11.2.1.

The binding affinity of an antibody to an antigen and the off-rate of an antibody-antigen interaction can be determined by competitive binding assays. One example of a competitive binding assay is a radioimmunoassay comprising the incubation of labeled antigen (e.g., $^3$H or $^{125}$I) with the antibody of interest in the presence of increasing amounts of unlabeled antigen, and the detection of the antibody bound to the labeled antigen. The affinity of the antibody of interest for a particular antigen and the binding off-rates can be determined from the data by scatchard plot analysis. Competition with a second antibody can also be determined using radioimmunoassays. In this case, the antigen is incubated with antibody of interest is conjugated to a labeled compound (e.g., $^3$H or $^{125}$I) in the presence of increasing amounts of an unlabeled second antibody.

Anti-CD100 antibodies, or antigen-binding fragments, variants, or derivatives thereof of the invention, additionally, can be employed histologically, as in immunofluorescence, immunoelectron microscopy or non-immunological assays, for in situ detection of CD100 protein or conserved variants or peptide fragments thereof. In situ detection may be accomplished by removing a histological specimen from a patient, and applying thereto a labeled anti-CD100 antibody, or antigen-binding fragment, variant, or derivative thereof, preferably applied by overlaying the labeled antibody (or fragment) onto a biological sample. Through the use of such a procedure, it is possible to determine not only the presence of CD100 protein, or conserved variants or peptide fragments, but also its distribution in the examined tissue. Using the present invention, those of ordinary skill will readily perceive that any of a wide variety of histological methods (such as staining procedures) can be modified in order to achieve such in situ detection.

Immunoassays and non-immunoassays for CD100 gene products or conserved variants or peptide fragments thereof will typically comprise incubating a sample, such as a biological fluid, a tissue extract, freshly harvested cells, or lysates of cells which have been incubated in cell culture, in the presence of a detectably labeled antibody capable of binding to CD100 or conserved variants or peptide fragments thereof, and detecting the bound antibody by any of a number of techniques well known in the art.

The biological sample may be brought in contact with and immobilized onto a solid phase support or carrier such as nitrocellulose, or other solid support which is capable of immobilizing cells, cell particles or soluble proteins. The support may then be washed with suitable buffers followed by treatment with the detectably labeled anti-CD100 antibody, or antigen-binding fragment, variant, or derivative thereof. The solid phase support may then be washed with the buffer a second time to remove unbound antibody. Optionally the antibody is subsequently labeled. The amount of bound label on solid support may then be detected by conventional means.

By "solid phase support or carrier" is intended any support capable of binding an antigen or an antibody. Well-known supports or carriers include glass, polystyrene, polypropylene, polyethylene, dextran, nylon, amylases, natural and modified celluloses, polyacrylamides, gabbros, and magnetite. The nature of the carrier can be either soluble to some extent or insoluble for the purposes of the present invention. The support material may have virtually any possible structural configuration so long as the coupled molecule is capable of binding to an antigen or antibody. Thus, the support configuration may be spherical, as in a bead, or cylindrical, as in the inside surface of a test tube, or the external surface of a rod. Alternatively, the surface may be flat such as a sheet, test strip, etc. Preferred supports include polystyrene beads. Those skilled in the art will know many other suitable carriers for binding antibody or antigen, or will be able to ascertain the same by use of routine experimentation.

The binding activity of a given lot of anti-CD100 antibody, or antigen-binding fragment, variant, or derivative thereof may be determined according to well known methods. Those skilled in the art will be able to determine operative and optimal assay conditions for each determination by employing routine experimentation.

There are a variety of methods available for measuring the affinity of an antibody-antigen interaction, but relatively few for determining rate constants. Most of the methods rely on either labeling antibody or antigen, which inevitably complicates routine measurements and introduces uncertainties in the measured quantities.

Surface plasmon reasonance (SPR) as performed on BIA-CORE® offers a number of advantages over conventional methods of measuring the affinity of antibody-antigen interactions: (i) no requirement to label either antibody or antigen; (ii) antibodies do not need to be purified in advance, cell culture supernatant can be used directly; (iii) real-time measurements, allowing rapid semi-quantitative comparison of different monoclonal antibody interactions, are enabled and are sufficient for many evaluation purposes; (iv) biospecific surface can be regenerated so that a series of different monoclonal antibodies can easily be compared under identical conditions; (v) analytical procedures are fully automated, and extensive series of measurements can be performed without user intervention. BIAapplications Handbook, version AB (reprinted 1998), BIACORE® code No. BR-1001-86; BIAtechnology Handbook, version AB (reprinted 1998), BIACORE® code No. BR-1001-84. SPR based binding studies require that one member of a binding pair be immobilized on a sensor surface. The binding partner immobilized is referred to as the ligand. The binding partner in solution is referred to as the analyte. In some cases, the ligand is attached indirectly to the surface through binding to another immobilized molecule, which is referred as the capturing molecule. SPR response reflects a change in mass concentration at the detector surface as analytes bind or dissociate.

Based on SPR, real-time BIACORE® measurements monitor interactions directly as they happen. The technique is well suited to determination of kinetic parameters. Comparative affinity ranking is extremely simple to perform, and both kinetic and affinity constants can be derived from the sensorgram data.

When analyte is injected in a discrete pulse across a ligand surface, the resulting sensorgram can be divided into three essential phases: (i) Association of analyte with ligand during sample injection; (ii) Equilibrium or steady state during sample injection, where the rate of analyte binding is balanced by dissociation from the complex; (iii) Dissociation of analyte from the surface during buffer flow.

The association and dissociation phases provide information on the kinetics of analyte-ligand interaction ($k_a$ and $k_d$, the rates of complex formation and dissociation, $k_d/k_a=K_D$). The equilibrium phase provides information on the affinity of the analyte-ligand interaction ($K_D$).

BIAevaluation software provides comprehensive facilities for curve fitting using both numerical integration and global fitting algorithms. With suitable analysis of the data, separate rate and affinity constants for interaction can be obtained from simple BIACORE® investigations. The range of affinities measurable by this technique is very broad ranging from mM to pM.

Epitope specificity is an important characteristic of a monoclonal antibody. Epitope mapping with BIACORE®, in contrast to conventional techniques using radioimmunoassay, ELISA or other surface adsorption methods, does not require labeling or purified antibodies, and allows multi-site specificity tests using a sequence of several monoclonal antibodies. Additionally, large numbers of analyses can be processed automatically.

Pair-wise binding experiments test the ability of two MAbs to bind simultaneously to the same antigen. MAbs directed against separate epitopes will bind independently, whereas MAbs directed against identical or closely related epitopes will interfere with each other's binding. These binding experiments with BIACORE® are straightforward to carry out.

For example, one can use a capture molecule to bind the first Mab, followed by addition of antigen and second MAb sequentially. The sensorgrams will reveal: 1. how much of the antigen binds to first Mab, 2. to what extent the second MAb binds to the surface-attached antigen, 3. if the second MAb does not bind, whether reversing the order of the pair-wise test alters the results.

Peptide inhibition is another technique used for epitope mapping. This method can complement pair-wise antibody binding studies, and can relate functional epitopes to structural features when the primary sequence of the antigen is known. Peptides or antigen fragments are tested for inhibition of binding of different MAbs to immobilized antigen. Peptides which interfere with binding of a given MAb are assumed to be structurally related to the epitope defined by that MAb.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Sambrook et al., ed. (1989) *Molecular Cloning A Laboratory Manual* (2nd ed.; Cold Spring Harbor Laboratory Press); Sambrook et al., ed. (1992) *Molecular Cloning: A Laboratory Manual*, (Cold Springs Harbor Laboratory, NY); D. N. Glover ed., (1985) *DNA Cloning*, Volumes I and II; Gait, ed. (1984) *Oligonucleotide Synthesis*; Mullis et al. U.S. Pat. No. 4,683,195; Hames and Higgins, eds. (1984) *Nucleic Acid Hybridization*; Hames and Higgins, eds. (1984) *Transcription And Translation*; Freshney (1987) *Culture Of Animal Cells* (Alan R. Liss, Inc.); *Immobilized Cells And Enzymes* (IRL Press) (1986); Perbal (1984) *A Practical Guide To Molecular Cloning*; the treatise, *Methods In Enzymology* (Academic Press, Inc., N.Y.); Miller and Calos eds. (1987) *Gene Transfer Vectors For Mammalian Cells*, (Cold Spring Harbor Laboratory); Wu et al., eds., *Methods In Enzymology*, Vols. 154 and 155; Mayer and Walker, eds. (1987) *Immunochemical Methods In Cell And Molecular Biology* (Academic Press, London); Weir and Blackwell, eds., (1986) *Handbook Of Experimental Immunology*, Volumes I-IV; *Manipulating the Mouse Embryo*, Cold Spring Harbor Laboratory Press, Cold Spring Harbor, N.Y., (1986); and in Ausubel et al. (1989) *Current Protocols in Molecular Biology* (John Wiley and Sons, Baltimore, Md.).

General principles of antibody engineering are set forth in Borrebaeck, ed. (1995) *Antibody Engineering* (2nd ed.; Oxford Univ. Press). General principles of protein engineering are set forth in Rickwood et al., eds. (1995) *Protein Engineering, A Practical Approach* (IRL Press at Oxford Univ. Press, Oxford, Eng.). General principles of antibodies and antibody-hapten binding are set forth in: Nisonoff (1984) *Molecular Immunology* (2nd ed.; Sinauer Associates, Sunderland, Mass.); and Steward (1984) *Antibodies, Their Structure and Function* (Chapman and Hall, New York, N.Y.). Additionally, standard methods in immunology known in the art and not specifically described are generally followed as in *Current Protocols in Immunology*, John Wiley & Sons, New York; Stites et al., eds. (1994) *Basic and Clinical Immunology* (8th ed; Appleton & Lange, Norwalk, Conn.) and Mishell and Shiigi (eds) (1980) *Selected Methods in Cellular Immunology* (W.H. Freeman and Co., NY).

Standard reference works setting forth general principles of immunology include *Current Protocols in Immunology*, John Wiley & Sons, New York; Klein (1982) *J., Immunology: The Science of Self-Nonself Discrimination* (John Wiley & Sons, NY); Kennett et al., eds. (1980) *Monoclonal Antibodies, Hybridoma: A New Dimension in Biological Analyses* (Plenum Press, NY); Campbell (1984) "Monoclonal Antibody Technology" in *Laboratory Techniques in Biochemistry and Molecular Biology*, ed. Burden et al., (Elsevere, Amsterdam); Goldsby et al., eds. (2000) *Kuby Immunnology* (4th ed.; H. Freemand & Co.); Roitt et al. (2001) *Immunology* (6th ed.; London: Mosby); Abbas et al. (2005) *Cellular and Molecular Immunology* (5th ed.; Elsevier Health Sciences Division); Kontermann and Dubel (2001) *Antibody Engineering* (Springer Verlan); Sambrook and Russell (2001) *Molecular Cloning: A Laboratory Manual* (Cold Spring Harbor Press); Lewin (2003) *Genes VIII* (Prentice Hall2003); Harlow and Lane (1988) *Antibodies: A Laboratory Manual* (Cold Spring Harbor Press); Dieffenbach and Dveksler (2003) *PCR Primer* (Cold Spring Harbor Press).

All of the references cited above, as well as all references cited herein, are incorporated herein by reference in their entireties.

The following examples are offered by way of illustration and not by way of limitation.

EXPERIMENTAL

Example 1

Generation of Chimeric and Humanized Anti-CD100 Antibodies

Figure 1:
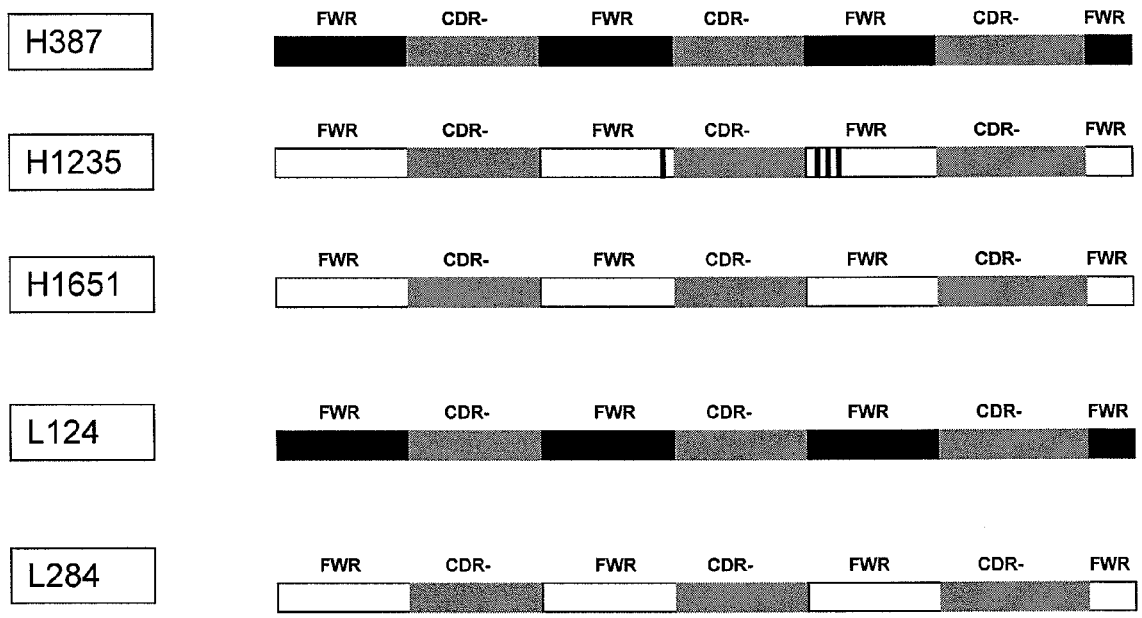

Chimeric antibodies were generated by RT-PCR cloning of the V genes from the $V_H$ and $V_K$ regions of the murine CD100 antibodies BD16 and BB18 hydridomas (described in International Patent Application WO 93/14125 and Herold et al. (1995) *Int. Immunol.* 7(1):1-8) onto the human IgG1 constant domain. The resulting chimeric antibodies are listed in Table 2 below. MAb 301 is chimeric BD16, and MAb 1893 is chimeric BB18. Using the sequence information from MAb 301, humanized antibodies MAb 657, MAb 1807, MAb 1656 and MAb 1808 were generated (FIG. 1 and Table 2).

TABLE 2

Human CD100 specific monoclonal antibodies

| MAb# | VH | VL | Isotype | AMINO ACID SEQ ID NO: | NUCLEOTIDE SEQ ID NO: |
|---|---|---|---|---|---|
| 301 | H387 | L124 | Human IgG1 | 3 (H387) | 60 (H387) |
|  |  |  |  | 5 (L124) | 62 (L124) |
| 1893 | H1751 | L458 | Human IgG1 | 6 (H1751) | 63 (H1751) |
|  |  |  |  | 7 (L458) | 64 (L458) |
| 657 | H1235 | L284 | Human IgG1 | 1 (H1235) | 58 (H1235) |
|  |  |  |  | 4 (L284) | 61 (L284) |
| 1807 | H1235 | L284 | Human IgG4 | 1 (H1235) | 58 (H1235) |
|  |  |  |  | 4 (L284) | 61 (L284) |
| 1656 | H1651 | L284 | Human IgG1 | 2 (H1651) | 59 (H1651) |
|  |  |  |  | 4 (L284) | 61 (L284) |
| 1808 | H1651 | L284 | Human IgG4 | 2 (H1651) | 59 (H1651) |
|  |  |  |  | 4 (L284) | 61 (L284) |

Example 2

Specificity of MAb 301 and MAb 657

Figure 2A:
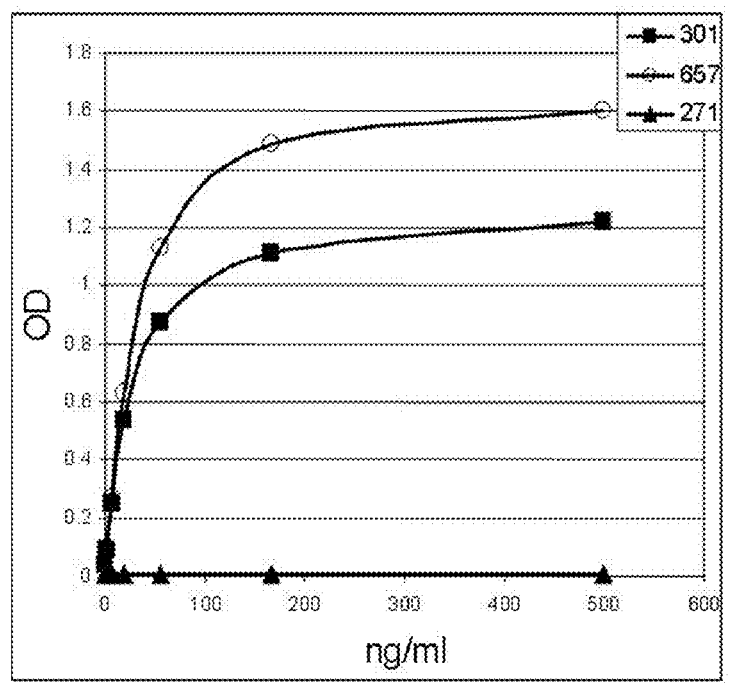
Figure 2B:
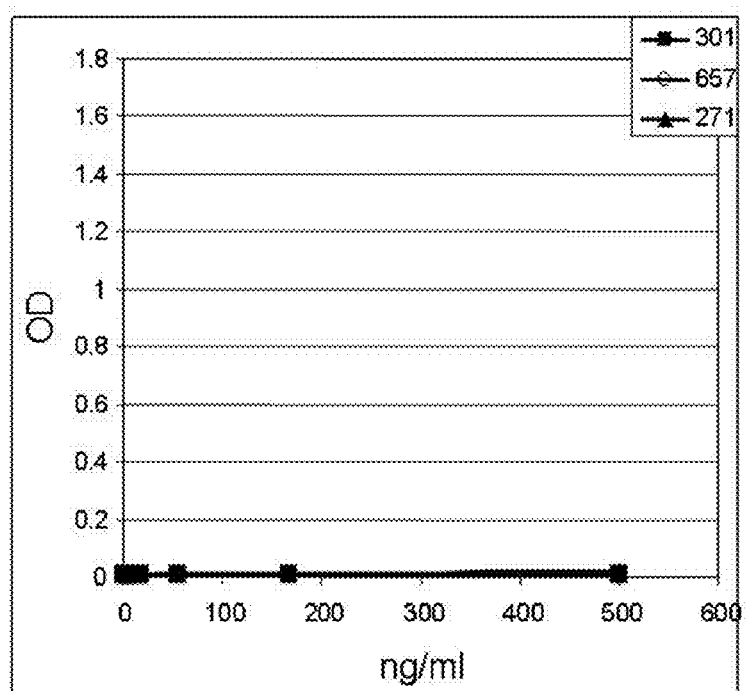

An ELISA assay was performed to demonstrate the specificity of MAb 301 and MAb 657. MAb 271 was used as a negative control chimeric antibody. Both MAb 301 and MAb 657 bound to CD100-Fc antigen (FIG. 2), but did not bind to the negative control antigens huErb2-Fc, BSA, human serum albumin, hemoglobin, insulin, or streptavidin. Similar results were obtained for MAbs 1656, 1807 and 1808.

Figure 3:
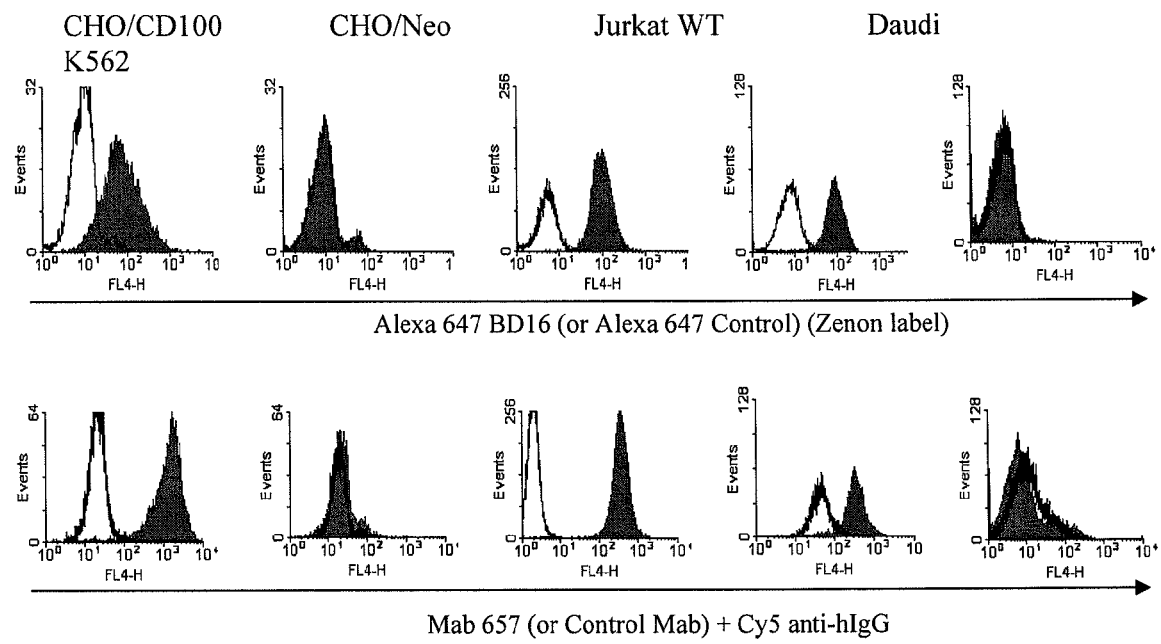
FIG. 3 shows the detection of CD100 expression on different cell lines using BD16 antibodies (top row) or MAb 657 (bottom row).

A comparison using flow cytometry was made between BD16 and MAb 657 to confirm specificity of CD100 binding in various CD100-expressing and non-expressing cell lines. Secondary reagents specific to mouse monoclonal antibodies were used for the measurement of BD16 specificity, and reagents specific to the measurement of MAb 657 specificity. As shown in FIG. 3, MAb 657 showed the same pattern of CD100 expression on CHO/CD100, CHO/neo, Jurkat WT, Daudi, and K562 cell lines.

Figure 4A:
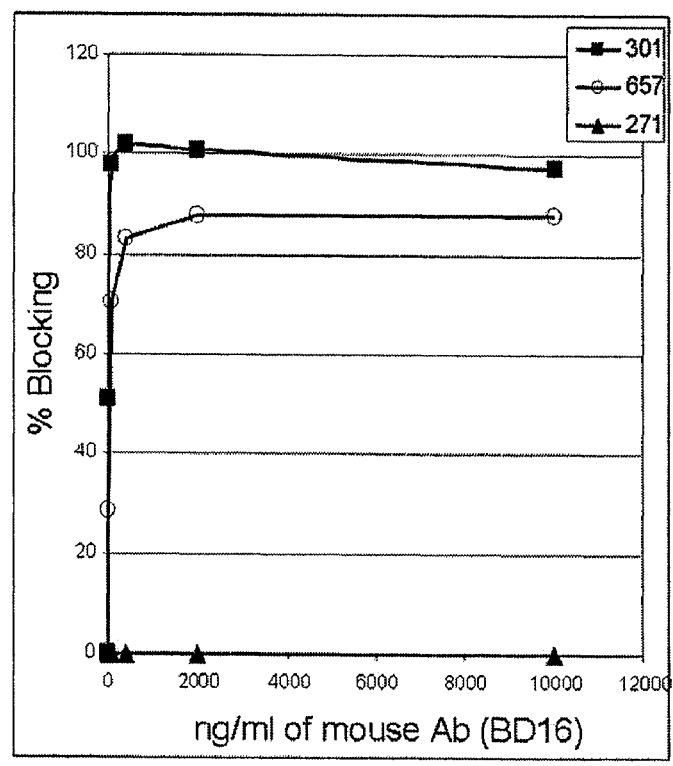
FIGS. 4A and 4B represent a competition ELISA using MAb 301 or MAb 657 in competition with BD16 for binding CD 100 antigen.
Figure 4B:
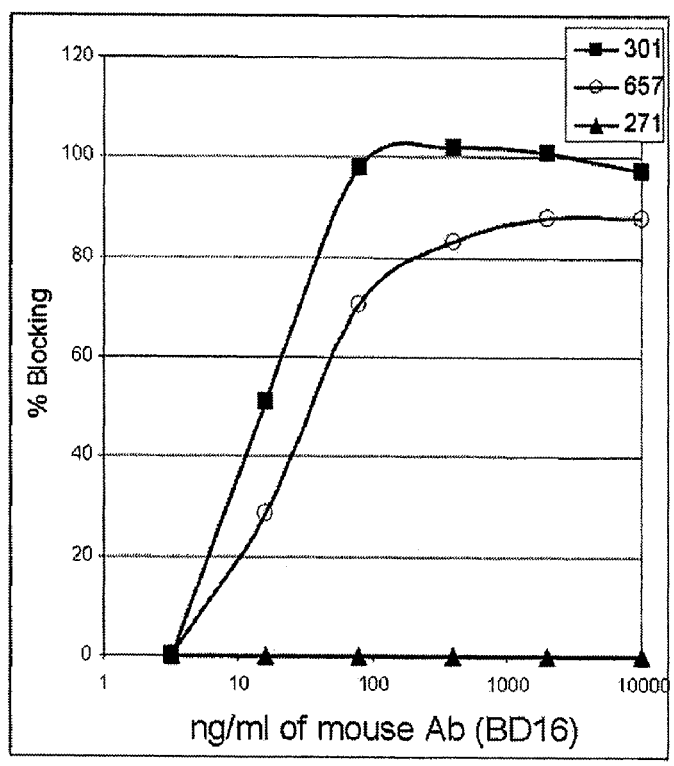

Competition ELISA assays were then performed. The ELISA plate was coated with CD100-Fc antigen, and BD16 or BB18 were allowed to bind individually to CD100. Five ng/ml of MAb 301 or MAb 657 was added to the mixture and incubated for a time sufficient to allow binding of the MAb to the CD100-Fc antigen. The cells were washed and antibody activity detected. Bound chimeric or human MAb was detected using anti-human Kappa HRP. As shown in FIG. 4, MAb 301 and MAb 657 binding to CD100 can be blocked by the BD16 mouse MAb. However, BB18 did not block the binding of MAb 301 or MAb 657 (data not shown). Similar results were obtained for MAbs 1656, 1807 and 1808.

Figure 5:
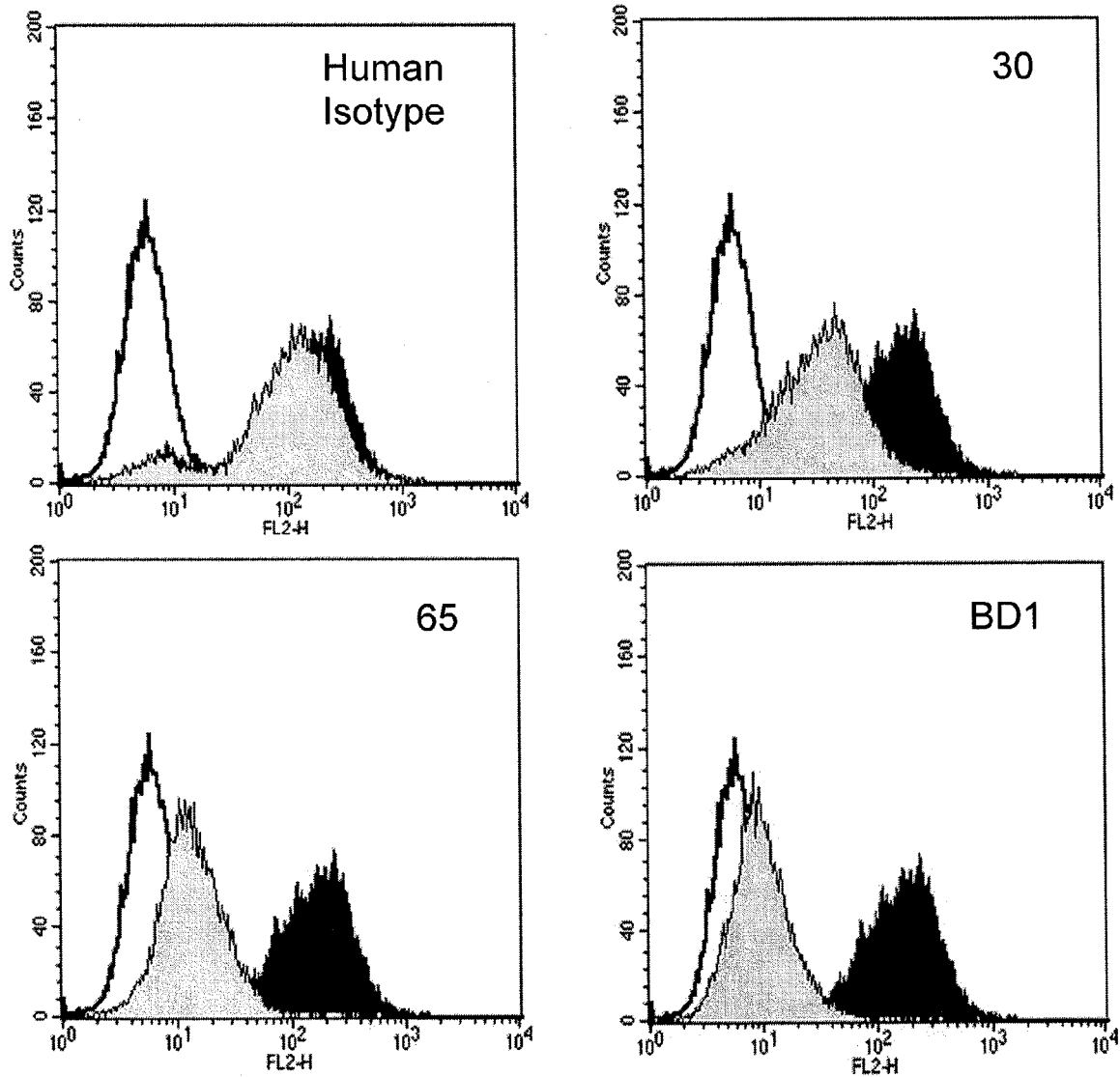
FIG. 5 shows the results from a competition flow cytometry assay where MAb 301 and MAb 657 competes with BD16 for binding to CD100 antigen. The black shading represents PE-BD16 with no blocking, the open shading represents PE-IgG1 with no blocking, and the gray shading represents 2 µg indicated blocking antibody plus PE-BD16.

To confirm the epitope specificity of the chimeric and human CD100 monoclonal antibodies, competition flow cytometry was performed. CD100+ cells (0.5 million) were first incubated with no antibody or with 2.0 μg of purified, humanized, chimeric, mouse, or negative control MAbs for 45 minutes at 4° C. The cells were then washed and labeled with a total of 0.7 μg of PE-mouse or PE-IgG1 isotype control antibody for 40 minutes at 4° C. Data was collected by FACS. As shown in FIG. 5, MAb 657 and MAb 301 compete with BD16 for binding to CD100.

Example 3

Antibody Affinity

Antibody affinity was measured according to the ELISA method described in Friguet et al. (1985) *J Immunol Methods* 77(2):305-19.

TABLE 3

| MAb affinity | |
|---|---|
| MAb | Affinity (nM) IC50 ELISA |
| BD16 | 0.13 |
| MAb 657 | 0.12 |
| MAb 1807 | 0.12 |
| IgG4 variant of MAb 657 |  |
| MAb 1656 | 0.12 |
| MAb 1808 | 0.13 |
| IgG4 variant of MAb 1656 |  |

Example 4

Monocyte Migration Assay

Monocyte migration was measured using the TRANSWELL® system (Corning Incorporated, Acton, Mass.) with 8-micron inserts. In the upper chambers, $10^5$ U937 cells were added together with 1.5 μg (15 μg/ml) of human CD100-Fc. The effect of BD16 or MAb 657 added in the upper chamber for the entire duration of migration at 100 μg/ml was studied. After 18 hours of incubation at 37° C., cells in suspension in the upper and lower chambers were enumerated by microscopy. The results are shown in FIG. 6. The addition of BD16 or MAb 657 to the assay suppressed the inhibition of migration induced by CD100. The effect of human MAb 657 was analogous to the effect of mouse BD16.

Example 5

Prevention of Apoptosis of Dev Cells

Dev is a human pluripotent neural precursor cell line. To measure the ability of MAb 657 to prevent CD100-induced apoptosis in this cell line, Dev cells were incubated with 200 ng/ml of CD100-FC with or without anti-CD100 MAb. The antibodies were added at various concentrations, and incubated for 48 hours. The cells were enumerated through microscopy. In each of the duplicates, six fields were enumerated. Both BD16 and MAb 657 inhibit the apoptosis induced by purified human CD100-Fc (Table 4).

TABLE 4

Prevention of apoptosis of Dev cells (number of live Dev cells/field)

| Dev cells | No antibody | 1.2 µg MAb | 0.6 µg MAb | 0.3 µg MAb |
|---|---|---|---|---|
| control (no CD100) | 75 +/− 11 | | | |
| Dev + Hu CD100 + BD16 | #45 +/− 7 | 56 +/− 11 | *60 +/− 14.5 | 45 +/− 7 |
| Dev + Hu CD100 + BD16 | #45 +/− 7 | *65 +/− 9 | *64 +/− 9 | 44 +/− 10 |

$p < 0.05$ relative to no CD100
*$p < 0.05$ relative to no antibody

Example 6

Binding of CD100 to Plexin B1+293 Cells

Human 293 cells were transfected with the cDNA encoding the CD100 receptor Plexin B1. Twenty nanograms CD100 (with C terminal His tag) or CD100-AP (with Alkaline Phosphatase and a His tag) was incubated alone or with various concentrations of anti-CD100 MAb (BD16 and MAb 1808) overnight at 4° C. The following morning, the CD100 or CD100 MAb was added to 293/Plexin cells and incubated for 30 minutes on ice. Cell bound CD100 was detected using biotinylated rabbit anti-His MAb, followed by streptavidin-APC, and cells were analyzed by flow cytometry. Neutralization of CD100 results in lower fluorescence. The results of this experiment are shown in FIG. 7.

Example 7

CD100-AP Binding Assay

COS cells were transfected with the cDNA encoding the CD100 receptor Plexin B1. Fifty nanograms CD100-AP (with placental secreted Alkaline Phosphatase and a His tag) was incubated alone or with various concentrations of anti-CD100 MAb overnight at 4° C. The following morning, the CD100-AP or CD100-AP/MAb was added to COS/Plexin cells and incubated for 90 minutes at room temperature. The cells were washed and then the amount of CD100 bound to individual cells was detected by measuring AP activity using standard procedures. Neutralization of CD100 results in lower activity. The results are shown in FIG. 8.

Example 8

Neutralization of CD100-Induced HUVEC Migration

An endothelial cell migration assay was performed. In this assay, 50,000 HUVECs were placed in the upper chamber of a Boyden Chamber, and the chemoattractants 0.1% BSA (negative control), 10% FBS (positive control), and serum free media conditioned overnight by CD100-secreting HN12 cells were placed in the bottom chamber. The assay was performed over 7 hours, and antibodies against CD100 (BD16 and MAb 1808), mouse IgG1, and human IgG4 were used at a concentration of 10 µg/ml. The results are shown in FIG. 9.

Example 9

COS Cell Growth Cone Collapse Assay

A heterologous assay has been developed to investigate CD100/Plexin B1 signaling (Turner and Hall (2006) *Methods in Enzymology* 406:665-676). CD100/Plexin B1 signaling induces a morphological collapse (cell rounding and disassembly of the actin cytoskeleton) that may correlate with growth cone collapse.

COS cells were transfected with Plexin B1 and Actin-EYFP. After 48 hours, the cells were stimulated for 30 minutes with CD100 blocking antibodies or a negative control antibody. Collapsed cells were visualized using fluorescent microscopy. The results of this assay are shown in FIG. 10.

Example 10

Affinity Improved MAbs

Targeted mutagenesis was performed on the H1651 $V_H$ domain (SEQ ID NO:2). The resulting $V_H$ was combined with L284 and affinity testing performed. The resulting mutants are listed in Tables 5 and 6 below.

TABLE 5

Affinity of H1651 mutants

| Mutated position# (corresponding to SEQ ID NO: 2) | Kabat position# (CDR/FWR) | Wild type amino acid | Mutant amino acid (MAb# with L284) | Affinity (MAb 1808)* | SEQ ID NO. of VH |
|---|---|---|---|---|---|
| | | | 1808 | 0.12-0.71 | 2 |
| 6 | 6 (FWR1) | Q | A (2144) | 0.43 (0.50) | 27 |
| 23 | 23 (FWR1) | K | T (2139) | 0.61 (0.71) | 28 |
| 31 | 31 (CDR1) | D | K (2163) | 0.06 (0.12) | 29 |
| 57 | 57 (CDR2) | G | F (2202) | 0.06 (0.12) | 30 |
| | | | W (2206) | 0.09 | 31 |
| | | | Y (2207) | 0.06 | 32 |
| 58 | 58 (CDR2) | A | G (2208) | 0.08 (0.12) | 33 |
| 59 | 59 (CDR2) | T | F (2216) | 0.06 (0.12) | 34 |
| | | | V (2218) | 0.08 | 35 |
| | | | W (2219) | 0.08 | 36 |

TABLE 5-continued

Affinity of H1651 mutants

| Mutated position# (corresponding to SEQ ID NO: 2) | Kabat position# (CDR/FWR) | Wild type amino acid | Mutant amino acid (MAb# with L284) | Affinity (MAb 1808)* | SEQ ID NO. of VH |
|---|---|---|---|---|---|
| 60 | 60 (CDR2) | Y | F (2220) | 0.04 (0.12) | 37 |
|  |  |  | P (2224) | 0.07 | 38 |
|  |  |  | V (2225) | 0.04 | 39 |
| 100 | 96 (CDR3) | E | D (2125) | 0.66 (0.57) | 40 |
| 104 | 100 (CDR3) | D | T (2117) | 0.52 (0.57) | 41 |

*Antibody affinity was compared to the measured affinity of MAb 1808 on the day each mutant MAb was measured.

TABLE 6

Affinity of double mutants

| MAb # | FWR Mutation | CDR Mutation (Original MAb #) | Affinity (MAb 1808)* | SEQ ID NO. Of VH |
|---|---|---|---|---|
| 2191 | K23T | D104T | 0.09 (0.13) | 54 |
| 2274 | Q6A | D31K (2163) | 0.10 | 42 |
| 2275 | Q6A | G57F (2202) | 0.09 | 44 |
| 2276 | Q6A | G57Y (2207) | 0.09 | 45 |
| 2277 | Q6A | T59F (2216) | 0.09 | 46 |
| 2278 | Q6A | Y60F (2220) | 0.11 | 47 |
| 2279 | Q6A | Y60V (2225) | 0.14 | 48 |
| 2280 | K23T | D31K (2163) | 0.13 | 43 |
| 2281 | K23T | G57F (2202) | 0.09 | 49 |
| 2282 | K23T | G57Y (2207) | 0.09 | 50 |
| 2283 | K23T | T59F (2216) | 0.13 | 51 |
| 2284 | K23T | Y60F (2220) | 0.24 | 52 |
| 2285 | K23T | Y60V (2225) | 0.10 | 53 |

*Antibody affinity was compared to the measured affinity of MAb 1808 on the day each mutant MAb was measured.

Example 11

Cell Attachment Assay

It has been shown that CD100 can signal through Plexin B1 to cause cells to detach from an extracellular matrix such as fibronectin (Kruger et al. (2005) *Nature Reviews Molecular Cell Biology* 6:789-800). A MAb that neutralizes CD100 should prevent this detachment. 293/plexin cells (normally grown as a suspension cell line) were plated at a density of 40,000 cells/well onto a fibronectin coated 96 well plate and allowed to attach overnight. Two μg/ml human CD100-His (with C terminal His tag) was incubated alone or with various concentrations of anti-CD100 MAb for 6 hours at 4° C. CD100 samples were brought to room temperature and then added to the 293/plexin cells. The cells were treated with CD100 for 30 minutes at 37 degrees, washed twice with PBS, and stained with crystal violet for 15 minutes. Cells were then washed twice with PBS and dried. Images were taken on a scanner for documentation. The crystal violet was then solubilized for 15 minutes at RT with 100 ul of 33% glacial acetic acid, and pipetted into a new plate. Absorbance was read at 570 nm. CD100 causes a reduction in the number of cells attached to the plate, and thus a reduced absorbance. Neutralization of CD100 results in an increase in absorbance (see FIGS. 11A and 11B).

Example 12

Binding of CD100 to Plexin B1+293 Cells

Human 293 cells were transfected with the cDNA encoding the CD100 receptor Plexin B1, and a stable cell line expressing Plexin B1 was selected. A neutralizing anti-CD100 MAb should prevent CD100 from binding to its cell surface receptor. Twenty nanograms of human or marmoset CD100-His (with C terminal His tag) were incubated alone or with various concentrations of anti-CD100 MAb overnight at 4° C. The next morning, the CD100 or CD100 pre-incubated with MAb was added to 293/Plexin cells and incubated for 30 minutes on ice. Cell bound CD100 was detected using biotinylated rabbit anti-His MAb, followed by streptavidin-APC, and cells were analyzed by flow cytometry. Neutralization of CD100 results in lower fluorescence (FIG. 12).

Example 13

Anti-CD100 MAbs Inhibit Growth of Tumor Xenogaft

CD100/SEMA4D has been demonstrated to induce endothelial cell migration and activation and displays angiogenic activity in vitro and in vivo. This activity is mediated through Plexin B1, and is independent of the VEGF Pathway (Conrotto et al. (2005) *Blood* 105:4321-4329). CD100/SEMA4D is expressed by a high percentage of human tumors. Tumor-derived CD100 is capable of inducing endothelial cell migration which can be neutralized by CD100 specific MAbs. It has been reported by others that genetic knockdown of CD100 in a tumor cell line delays tumor growth in vivo (Basile et al. (2006) *Proc. Nat. Acad. Sci.* 103:9017-9022). The following studies were initiated to determine whether a similar effect could be obtained by treatment with an anti-CD100 antibody of the invention.

HN12 is a head and neck cancer cell line that expresses CD100. HN12 xenografts were established by subcutaneous (s.c.) injection in nude mice. The mice were treated by i.p. injection with 1 mg of MAb 2282 or human IgG isotype control twice a week starting one day after tumor grafting. Tumor growth was measured two or three times per week. Treatment with MAb 2282 reduced the rate of tumor growth (FIG. 13).

Example 14

Anti-CD100 Antibodies are Capable of Inhibiting CD100 Activity In Vivo

In an effort to validate the use of anti-CD100 neutralizing antibodies for use in vivo in the treatment of various diseases, we measured the effects of mouse anti-CD100 antibodies in multiple in vivo assays.

The mouse anti-CD100 antibodies recognize both human and murine CD100 and were generated using the methods described herein. The Line 1 cell line was derived from a spontaneous lung tumor in a BALB/c mouse. Previously we have shown that injection of BALB/c mice with live Line1 cells that have been transfected with a foreign cDNA was an effective way to induce immune responses. The Line 1 cell line was transfected with an expression plasmid encoding the full length human CD100 cDNA and a stable line expressing human CD100 was isolated. CD100 deficient mice (BALB/c background (Kumanogoh et al. (2002) *J. Immunol.* 169:1175-1181) were primed by immunization with purified mouse CD100-His (the extracellular domain of mouse CD100 with a C-terminal 6× his tag for purification) emulsified in complete Freund's adjuvant (CFA). One week following this immunization, the mice were injected intramuscularly (i.m.) with 200,000 live Line1.CD100 cells. Nineteen days after the Line1.CD100 injection the mice were sacrificed, spleens harvested and fused with the P3X63Ag8.653 fusion partner (ATCC #CRL-1580) following standard procedures to generate hybridomas. Hybridoma clones were screened by ELISA for binding to human and mouse CD100. Three antibodies, clones 59, 67 and 76, exhibited high affinity for both mouse and human CD100 (See Table 7).

TABLE 7

Affinity Measurements for mouse anti-CD100 MAbs

| MAb | Isotype | Affinity for Mouse CD100 (nM)* | Affinity for Human CD100 (nM)* |
|---|---|---|---|
| 59 | IgG2b | 1.00 | 1.2 |
| 67 | IgG1 | 1.00 | 5.7 |
| 76 | IgG2b | 0.33 | 0.12 |

*Affinity was measured using BIACORE ® surface plasmon resonance technology

The CD100 specific antibodies were screened for their ability to inhibit CD100 in the two in vitro assays described in Experimental Examples 11 and 12. Similar to the plexin B1 receptor binding assay described in Experimental Example 12, forty nanograms (ng) of human or mouse CD100-His (with C terminal His tag) were incubated alone or with various concentrations of anti-CD100 MAb overnight at 4° C. The next morning, the CD100 or CD100 pre-incubated with MAb was added to 293/Plexin cells and incubated for 30 minutes on ice. Cell bound CD100 was detected using biotinylated rabbit anti-His MAb, followed by streptavidin-APC, and cells were analyzed by flow cytometry. Neutralization of CD100 results in lower fluorescence. MAb 67, MAb 76 and MAb 59 were all able to block human and mouse CD100 from binding to Plexin B1 (FIG. 14 and data not shown).

The antibodies were also tested for their ability to inhibit CD100 in a cell detachment assay, as described in Experimental Example 11. As shown in FIG. 15, all three MAbs were able to block mouse CD100 mediated cell detachment. All three MAbs were also able to block cell detachment mediated by human CD100 (data not shown).

The anti-CD100 antibodies 59, 67 and 76 were tested for their ability to inhibit B cell responses in vivo. BALB/c mice were injected with an emulsion of 100 µg of ovalbumin (OVA) in complete Freud's adjuvant (CFA) i.p. Groups of five mice were co-treated with 300 µg of the monoclonal anti-CD100 antibodies 59, 67 or 76, or an isotype control. The mice were treated with the same monoclonal antibodies again on days 3, 7, and 10. At day 7 and 12, serum was collected from each mouse and analyzed for the presence of OVA-specific serum IgG using a standard ELISA (coat ELISA plate with ovalbumin, add dilutions of serum, detect ovalbumin binding antibodies using anti-mouse IgG secondary antibody). One group of five mice was left untreated and served as a naïve control group. As an additional control, a group of CD100 deficient mice (Kumanogoh et al. (2002) *J. Immunol.* 169:1175-1181) were injected with the 100 µg OVA/CFA i.p., but were not administered an antibody. Results are shown in FIGS. 16A and 16B. The CD100 deficient mice exhibit a reduction in the titer of OVA specific IgG levels of approximately 40%. The groups of mice that had been injected with the anti-CD100 monoclonal antibodies 59 and 76 exhibit equivalent results, with approximately a 60% reduction in OVA-specific IgG levels. MAb 67 did not significantly inhibit ovalbumin specific antibody responses.

An antibody cross-blocking ELISA demonstrated that MAb 59 and MAb 76 recognize an overlapping epitope on CD100. MAb 67 recognizes a distinct epitope. MAbs 59, 76 and 67 recognize an epitope that is distinct from that recognized by BD16 and its humanized variants (ex. MAb 1808 and 2282). Based on the results from the in vitro and in vivo assays, MAb 76 was selected for further functional testing in animal disease models.

Example 15

Test of anti-CD100 MAbs in Mouse EAE Studies

Multiple sclerosis (MS) is an immune-mediated disorder of the CNS leading to progressive decline of motor and sensory functions causing permanent disability. EAE is an accepted animal model for multiple sclerosis. EAE was induced in C57BL/6 mice by the well-established protocol of injecting an emulsion consisting of $MOG_{35-55}$ peptide (150.0 µg/mouse) in CFA. A volume of 0.2 ml of emulsion was injected subcutaneously into the flanks of the mice. Pertussis toxin was injected intraperitoneally on the day of induction and 48 hours later.

Mice were dosed with 10 mg/kg (200 µg per mouse) of MAb 76 or control antibody intravenously (i.v.) on Days 1, 5, 9 and 12. The mice were observed daily from the $10^{th}$ day post-EAE induction for EAE clinical signs and scored according to the grades described in the table below.

TABLE 8

Evaluation of the EAE clinical signs.

| Score | Signs | Description |
|---|---|---|
| 0 | Normal behavior | No neurological signs. |
| 1 | Distal limp tail | The distal part of the tail is limp and droopy. |
| 1.5 | Complete limp tail | The whole tail is loose and droopy. |
| 2 | righting reflex | Animal has difficulties rolling onto his feet when laid on its back |
| 3 | ataxia | wobbly walk - when the mouse walks the hind legs are unsteady |
| 4 | early paralysis | The mouse has difficulties standing on its hind legs but still has remnants of movement. |
| 5 | Full paralysis | The mouse can't move it's legs at all, it looks thiner and emaciated. |
| 6 | Moribund/Death | |

The results from this study are shown in FIG. 17. Treatment with MAb 76 reduced Group Mean Score (GMS) of clinical signs by approximately 50%.

CSJL EAE

The CSJL/FI strain is another established EAE model to test for the efficacy of candidate molecules for the treatment of inflammatory demyelination as occurs in MS. Disease was induced in all mice by the injection of an emulsion of mouse spinal cord homogenate (MSCH) in complete Freund's adjuvant (CFA). Pertussis toxin was administered intravenously on the day of MSCH/CFA injection and again 48 hours later. MAb 76 (10 mg/kg) and control were administered i.v twice weekly starting on Day 1.

Scoring of EAE clinical signs was initiated from the 10th day post-EAE induction and continued daily until Day 23. The clinical signs were recorded according to a grading system described in the table below.

TABLE 9

Evaluation of the EAE clinical signs.

| Score | Signs | Description |
|---|---|---|
| 0 | Normal behavior | No neurological signs. |
| 1 | Tail weakness | The mouse tail is limp and droops. |
| 2 | Hind legs weakness | Limb paresis, wobbly walk - when the mouse walks the hind legs are unsteady. |
| 3 | Hind legs paralysis | The mouse can't move it's hind legs and it drags them when he walks. |
| 4 | Full paralysis | The mouse can't move it's legs at all, it looks thinner and emaciated. |
| 5 | Death | |

The results from this study are shown in FIG. 18. Treatment with MAb 76 reduced Group Mean Score (GMS) of clinical signs by approximately 50%.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims and list of embodiments disclosed herein. Although specific terms are employed herein, they are used in a generic and descriptive sense only and not for purposes of limitation.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

What is claimed is:

1. A humanized immunoglobulin that specifically binds CD100, wherein said immunoglobulin comprises a variable heavy ($V_H$) domain and a variable light ($V_L$) domain, wherein said $V_H$ domain comprises a polypeptide having an amino acid sequence selected from the group consisting of SEQ ID NOS: 32, 45, and 50, and wherein said $V_L$ domain comprises a polypeptide having an amino acid sequence set forth in SEQ ID NO:4 or 5.

2. The humanized immunoglobulin of claim 1, wherein said immunoglobulin is an IgG1 kappa immunoglobulin.

3. The humanized immunoglobulin of claim 2, wherein said immunoglobulin comprises a human IgG1 constant region within a heavy chain of said immunoglobulin and a human kappa constant region within a light chain of said immunoglobulin.

4. The humanized immunoglobulin of claim 1, wherein said immunoglobulin is an IgG4 kappa immunoglobulin.

5. The humanized immunoglobulin of claim 4, wherein said immunoglobulin comprises a human IgG4 constant region within a heavy chain of said immunoglobulin and a human kappa constant region within a light chain of said immunoglobulin.

6. The humanized immunoglobulin of claim 1, wherein said immunoglobulin is an IgG3 kappa immunoglobulin.

7. The humanized immunoglobulin of claim 6, wherein said immunoglobulin comprises a human IgG3 constant region within a heavy chain of said immunoglobulin and a human kappa constant region within a light chain of said immunoglobulin.

8. The humanized immunoglobulin of claim 1, wherein said immunoglobulin is an IgG2 kappa immunoglobulin.

9. The humanized immunoglobulin of claim 8, wherein said immunoglobulin comprises a human IgG2 constant region within a heavy chain of said immunoglobulin and a human kappa constant region within a light chain of said immunoglobulin.

10. The humanized immunoglobulin of claim 1, wherein said immunoglobulin exhibits CD100 blocking activity.

11. The humanized immunoglobulin of claim 1, further comprising a heterologous polypeptide fused thereto.

12. The humanized immunoglobulin of claim 1, wherein said immunoglobulin is conjugated to an agent selected from the group consisting of a therapeutic agent, a prodrug, a peptide, a protein, an enzyme, a virus, a lipid, a biological response modifier, a pharmaceutical agent, and PEG.

13. A composition comprising the humanized immunoglobulin of claim 1.

14. The composition of claim 13, further comprising a carrier.

15. A pharmaceutical composition comprising the humanized immunoglobulin according to claim 1.

16. The humanized immunoglobulin of claim 1, wherein said $V_L$ domain comprises a polypeptide having a the amino acid sequence set forth in SEQ ID NO:4.

17. An isolated immunoglobulin that specifically binds CD100, wherein said immunoglobulin comprises:
   a) a heavy chain having a variable heavy ($V_H$) domain comprising:
      i) a complementarity-determining region 1 (CDR1) having the amino acid sequence set forth in SEQ ID NO: 9;
      ii) a CDR2 having the amino acid sequence set forth in SEQ ID NO: 17; and
      iii) a CDR3 having the amino acid sequence set forth in SEQ ID NO: 11; and
   b) a light chain having a variable light ($V_L$) domain comprising:
      i) a CDR1 having the amino acid sequence set forth in amino acid residues 24-40 of SEQ ID NO: 4 or 5;
      ii) a CDR2 having the amino acid sequence set forth in amino acid residues 56-62 of SEQ ID NO: 4 or 5; and
      iii) a CDR3 having the amino acid sequence set forth in amino acid residues 95-103 of SEQ ID NO: 4 or 5.

18. The isolated immunoglobulin of claim 17, wherein said immunoglobulin comprises fully or partially human framework regions within said $V_H$ domain and within said $V_L$ domain.

19. The isolated immunoglobulin of claim 17, wherein said $V_H$ domain has the amino acid sequence set forth in SEQ ID NO: 32, 45, or 50.

20. The isolated immunoglobulin of claim 17, wherein said $V_L$ domain has the amino acid sequence set forth in SEQ ID NO: 4 or 5.

21. The isolated immunoglobulin of claim 17, wherein said immunoglobulin is an IgG1 kappa immunoglobulin.

22. The isolated immunoglobulin of claim 21, wherein said immunoglobulin comprises a human IgG1 constant region within said heavy chain of said immunoglobulin and a human kappa constant region within said light chain of said immunoglobulin.

23. The isolated immunoglobulin of claim 17, wherein said immunoglobulin is an IgG4 kappa immunoglobulin.

24. The isolated immunoglobulin of claim 23, wherein said immunoglobulin comprises a human IgG4 constant region within said heavy chain of said immunoglobulin and a human kappa constant region within said light chain of said immunoglobulin.

25. The isolated immunoglobulin of claim 17, wherein said immunoglobulin is an IgG3 kappa immunoglobulin.

26. The isolated immunoglobulin of claim 25, wherein said immunoglobulin comprises a human IgG3 constant region within said heavy chain of said immunoglobulin and a human kappa constant region within said light chain of said immunoglobulin.

27. The isolated immunoglobulin of claim 17, wherein said immunoglobulin is an IgG2 kappa immunoglobulin.

28. The isolated immunoglobulin of claim 27, wherein said immunoglobulin comprises a human IgG2 constant region within said heavy chain of said immunoglobulin and a human kappa constant region within said light chain of said immunoglobulin.

29. The isolated immunoglobulin of claim 17, wherein said immunoglobulin exhibits CD100 blocking activity.

30. The isolated immunoglobulin of claim 17, further comprising a heterologous polypeptide fused thereto.

31. The isolated immunoglobulin of claim 17, wherein said immunoglobulin is conjugated to an agent selected from the group consisting of a therapeutic agent, a prodrug, a peptide, a protein, an enzyme, a virus, a lipid, a biological response modifier, a pharmaceutical agent, and PEG.

32. A composition comprising the isolated immunoglobulin of claim 17.

33. The composition of claim 32, further comprising a carrier.

34. A pharmaceutical composition comprising the isolated immunoglobulin according to claim 17.

35. The humanized immunoglobulin of claim 1, wherein said $V_H$ domain comprises a polypeptide having the amino acid sequence set forth in SEQ ID NO:50.

36. A humanized immunoglobulin that specifically binds CD100, wherein said immunoglobulin comprises a variable heavy ($V_H$) domain having the amino acid sequence set forth in SEQ ID NO:50 and a variable light ($V_L$) domain having the amino acid sequence set forth in SEQ ID NO:4.

* * * * *

SEQUENCE LISTING

```
<160> NUMBER OF SEQ ID NOS: 65

<210> SEQ ID NO 1
<211> LENGTH: 122
<212> TYPE: PRT
<213> ORGANISM: Artificial sequence
<220> FEATURE:
<223> OTHER INFORMATION: anti-CD100 variable domain -

<400> SEQUENCE: 1

Gln Val Gln Leu Val Gln Ser Gly Ala Glu Val Lys Lys Pro Gly Ser
 1               5                  10                  15

Ser Val Lys Val Ser Cys Lys Ala Ser Gly Tyr Thr Phe Thr Asp Tyr
                20                  25                  30

Tyr Met Asp Trp Val Arg Gln Ala Pro Gly Gln Gly Leu Glu Trp Ile
            35                  40                  45

Gly Arg Val Asn Pro Tyr His Gly Gly Ala Thr Tyr Asn Gln Lys Phe
        50                  55                  60

Lys Gly Lys Ala Thr Ile Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Glu Asn Ser Tyr Asp Gly Tyr Tyr Gly Met Asp Tyr Trp
               100                 105                 110

Gly Gln Gly Thr Leu Val Thr Val Ser Ser
           115                 120

<210> SEQ ID NO 2
<211> LENGTH: 122
<212> TYPE: PRT
<213> ORGANISM: Artificial sequence
<220> FEATURE:
<223> OTHER INFORMATION: anti-CD100 variable domain -

<400> SEQUENCE: 2

Gln Val Gln Leu Val Gln Ser Gly Ala Glu Val Lys Lys Pro Gly Ser
```

```
                1               5                  10                  15
Ser Val Lys Val Ser Cys Lys Ala Ser Gly Tyr Thr Phe Thr Asp Tyr
                    20                  25                  30

Tyr Met Asp Trp Val Arg Gln Ala Pro Gly Gln Gly Leu Glu Trp Met
            35                  40                  45

Gly Arg Val Asn Pro Tyr His Gly Gly Ala Thr Tyr Asn Gln Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Glu Asn Ser Tyr Asp Gly Tyr Tyr Gly Met Asp Tyr Trp
                    100                 105                 110

Gly Gln Gly Thr Leu Val Thr Val Ser Ser
                115                 120

<210> SEQ ID NO 3
<211> LENGTH: 122
<212> TYPE: PRT
<213> ORGANISM: Artificial sequence
<220> FEATURE:
<223> OTHER INFORMATION: anti-CD100 variable domain -

<400> SEQUENCE: 3

Glu Val Gln Leu Gln Gln Ser Gly Pro Glu Leu Val Lys Pro Gly Ala
1               5                  10                  15

Ser Val Lys Met Ser Cys Lys Ala Ser Gly Tyr Thr Phe Thr Asp Tyr
                    20                  25                  30

Tyr Met Asp Trp Val Lys Gln Ser His Gly Glu Ser Phe Glu Trp Ile
            35                  40                  45

Gly Arg Val Asn Pro Tyr His Gly Gly Ala Thr Tyr Asn Gln Lys Phe
    50                  55                  60

Lys Gly Lys Ala Thr Leu Thr Val Asp Lys Ser Ser Arg Thr Ala Tyr
65                  70                  75                  80

Met Glu Leu Asn Ser Leu Thr Tyr Glu Asp Ser Ala Val Tyr Tyr Cys
                85                  90                  95

Ala Arg Glu Glu Asn Ser Tyr Asp Gly Tyr Tyr Gly Met Asp Tyr Trp
                    100                 105                 110

Gly Gln Gly Thr Thr Val Thr Val Ser Ser
                115                 120

<210> SEQ ID NO 4
<211> LENGTH: 113
<212> TYPE: PRT
<213> ORGANISM: Artificial sequence
<220> FEATURE:
<223> OTHER INFORMATION: anti-CD100 variable domain -

<400> SEQUENCE: 4

Asp Ile Val Met Thr Gln Ser Pro Leu Ser Leu Pro Val Ser Pro Gly
1               5                  10                  15

Glu Pro Ala Thr Ile Asn Cys Lys Ser Ser Gln Ser Leu Phe Asn Ser
                    20                  25                  30

Gly Asn Gln Lys Asn Tyr Leu Ala Trp Tyr Leu Gln Lys Pro Gly Gln
            35                  40                  45

Pro Pro Lys Leu Leu Ile Tyr Gly Ala Ser Thr Arg Glu Ser Gly Val
    50                  55                  60

Pro Asp Arg Phe Ser Gly Ser Gly Ser Gly Thr Asp Phe Thr Leu Thr
```

```
                65                  70                  75                  80
Ile Ser Ser Leu Gln Ala Glu Asp Val Ala Val Tyr Tyr Cys Gln Asn
                    85                  90                  95

Asp His Thr Tyr Pro Tyr Thr Phe Gly Gln Gly Thr Lys Leu Glu Ile
                100                 105                 110

Lys

<210> SEQ ID NO 5
<211> LENGTH: 113
<212> TYPE: PRT
<213> ORGANISM: Artificial sequence
<220> FEATURE:
<223> OTHER INFORMATION: anti-CD100 variable domain -

<400> SEQUENCE: 5

Asp Ile Val Leu Thr Gln Ser Pro Ser Ser Leu Ser Val Ser Ala Gly
1               5                   10                  15

Glu Lys Val Thr Met Asp Cys Lys Ser Ser Gln Ser Leu Phe Asn Ser
                20                  25                  30

Gly Asn Gln Lys Asn Tyr Leu Ala Trp Tyr His Gln Lys Pro Gly Gln
            35                  40                  45

Pro Pro Lys Leu Leu Ile Tyr Gly Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                    85                  90                  95

Asp His Thr Tyr Pro Tyr Thr Phe Gly Gly Gly Thr Lys Leu Glu Ile
                100                 105                 110

Lys

<210> SEQ ID NO 6
<211> LENGTH: 118
<212> TYPE: PRT
<213> ORGANISM: Artificial sequence
<220> FEATURE:
<223> OTHER INFORMATION: anti-CD100 variable domain -

<400> SEQUENCE: 6

Glu Val Lys Leu Gln Glu Ser Gly Gly Gly Leu Val Gln Pro Gly Gly
1               5                   10                  15

Ser Leu Asn Leu Ser Cys Thr Ala Ser Gly Phe Asp Phe Ser Arg Tyr
                20                  25                  30

Trp Met Ser Trp Ala Arg Gln Ala Pro Gly Lys Gly Gln Glu Trp Ile
            35                  40                  45

Gly Glu Ile Asn Pro Gly Ser Ser Thr Ile Asn Tyr Thr Pro Ser Leu
    50                  55                  60

Lys Asp Lys Phe Ile Ile Ser Arg Asp Asn Ala Lys Asn Thr Leu Tyr
65                  70                  75                  80

Leu Gln Met Ser Lys Val Arg Ser Glu Asp Thr Ala Leu Tyr Tyr Cys
                    85                  90                  95

Ala Arg Gln Gly Thr Tyr Tyr Thr Met Asp Tyr Trp Gly Gln Gly Thr
                100                 105                 110

Thr Val Thr Val Ser Ser
            115

<210> SEQ ID NO 7
<211> LENGTH: 106
```

```
<212> TYPE: PRT
<213> ORGANISM: Artificial sequence
<220> FEATURE:
<223> OTHER INFORMATION: anti-CD100 variable domain -

<400> SEQUENCE: 7

Asp Ile Gln Met Thr Gln Ser Pro Ser Ser Leu Ser Ala Ser Leu Gly
 1               5                  10                  15

Gly Lys Val Thr Ile Thr Cys Lys Ala Ser Gln Asp Ile Asn Lys Tyr
            20                  25                  30

Ile Ser Trp Tyr Gln Asp Lys Pro Gly Lys Gly Pro Gly Leu Leu Ile
        35                  40                  45

His Tyr Thr Ser Thr Leu Gln Pro Gly Ile Pro Ser Arg Phe Ser Gly
 50                  55                  60

Ser Gly Ser Gly Arg Asp Tyr Ser Phe Ser Ile Ser Asn Leu Glu Pro
65                  70                  75                  80

Glu Asp Ile Ala Thr Tyr Tyr Cys Leu Gln Tyr Asp Asn Leu Tyr Thr
                85                  90                  95

Phe Gly Gly Gly Thr Lys Leu Glu Ile Lys
            100                 105

<210> SEQ ID NO 8
<211> LENGTH: 25
<212> TYPE: PRT
<213> ORGANISM: Artificial sequence
<220> FEATURE:
<223> OTHER INFORMATION: anti-CD100 variable domain -

<400> SEQUENCE: 8

Gln Val Gln Leu Val Gln Ser Gly Ala Glu Val Lys Lys Pro Gly Ser
 1               5                  10                  15

Ser Val Lys Val Ser Cys Lys Ala Ser
            20                  25

<210> SEQ ID NO 9
<211> LENGTH: 10
<212> TYPE: PRT
<213> ORGANISM: Artificial sequence
<220> FEATURE:
<223> OTHER INFORMATION: anti-CD100 variable domain -

<400> SEQUENCE: 9

Gly Tyr Thr Phe Thr Asp Tyr Tyr Met Asp
 1               5                  10

<210> SEQ ID NO 10
<211> LENGTH: 16
<212> TYPE: PRT
<213> ORGANISM: Artificial sequence
<220> FEATURE:
<223> OTHER INFORMATION: anti-CD100 variable domain -

<400> SEQUENCE: 10

Arg Val Asn Pro Tyr His Gly Gly Ala Thr Tyr Asn Gln Lys Phe Lys
 1               5                  10                  15

<210> SEQ ID NO 11
<211> LENGTH: 13
<212> TYPE: PRT
<213> ORGANISM: Artificial sequence
<220> FEATURE:
<223> OTHER INFORMATION: anti-CD100 variable domain -

<400> SEQUENCE: 11
```

Glu Glu Asn Ser Tyr Asp Gly Tyr Tyr Gly Met Asp Tyr
1               5                   10

<210> SEQ ID NO 12
<211> LENGTH: 25
<212> TYPE: PRT
<213> ORGANISM: Artificial sequence
<220> FEATURE:
<223> OTHER INFORMATION: anti-CD100 variable domain -

<400> SEQUENCE: 12

Gln Val Gln Leu Val Ala Ser Gly Ala Glu Val Lys Lys Pro Gly Ser
1               5                   10                  15

Ser Val Lys Val Ser Cys Lys Ala Ser
            20                  25

<210> SEQ ID NO 13
<211> LENGTH: 25
<212> TYPE: PRT
<213> ORGANISM: Artificial sequence
<220> FEATURE:
<223> OTHER INFORMATION: anti-CD100 variable domain -

<400> SEQUENCE: 13

Gln Val Gln Leu Val Gln Ser Gly Ala Glu Val Lys Lys Pro Gly Ser
1               5                   10                  15

Ser Val Lys Val Ser Cys Thr Ala Ser
            20                  25

<210> SEQ ID NO 14
<211> LENGTH: 10
<212> TYPE: PRT
<213> ORGANISM: Artificial sequence
<220> FEATURE:
<223> OTHER INFORMATION: anti-CD100 variable domain -

<400> SEQUENCE: 14

Gly Tyr Thr Phe Thr Lys Tyr Tyr Met Asp
1               5                   10

<210> SEQ ID NO 15
<211> LENGTH: 17
<212> TYPE: PRT
<213> ORGANISM: Artificial sequence
<220> FEATURE:
<223> OTHER INFORMATION: anti-CD100 variable domain -

<400> SEQUENCE: 15

Arg Val Asn Pro Tyr His Gly Phe Ala Thr Tyr Asn Gln Lys Phe Lys
1               5                   10                  15

Gly

<210> SEQ ID NO 16
<211> LENGTH: 17
<212> TYPE: PRT
<213> ORGANISM: Artificial sequence
<220> FEATURE:
<223> OTHER INFORMATION: anti-CD100 variable domain -

<400> SEQUENCE: 16

Arg Val Asn Pro Tyr His Gly Trp Ala Thr Tyr Asn Gln Lys Phe Lys
1               5                   10                  15

Gly

<210> SEQ ID NO 17

```
<211> LENGTH: 17
<212> TYPE: PRT
<213> ORGANISM: Artificial sequence
<220> FEATURE:
<223> OTHER INFORMATION: anti-CD100 variable domain -

<400> SEQUENCE: 17

Arg Val Asn Pro Tyr His Gly Tyr Ala Thr Tyr Asn Gln Lys Phe Lys
 1               5                  10                  15

Gly

<210> SEQ ID NO 18
<211> LENGTH: 17
<212> TYPE: PRT
<213> ORGANISM: Artificial sequence
<220> FEATURE:
<223> OTHER INFORMATION: anti-CD100 variable domain -

<400> SEQUENCE: 18

Arg Val Asn Pro Tyr His Gly Gly Gly Thr Tyr Asn Gln Lys Phe Lys
 1               5                  10                  15

Gly

<210> SEQ ID NO 19
<211> LENGTH: 17
<212> TYPE: PRT
<213> ORGANISM: Artificial sequence
<220> FEATURE:
<223> OTHER INFORMATION: anti-CD100 variable domain -

<400> SEQUENCE: 19

Arg Val Asn Pro Tyr His Gly Gly Ala Phe Tyr Asn Gln Lys Phe Lys
 1               5                  10                  15

Gly

<210> SEQ ID NO 20
<211> LENGTH: 17
<212> TYPE: PRT
<213> ORGANISM: Artificial sequence
<220> FEATURE:
<223> OTHER INFORMATION: anti-CD100 variable domain -

<400> SEQUENCE: 20

Arg Val Asn Pro Tyr His Gly Gly Ala Val Tyr Asn Gln Lys Phe Lys
 1               5                  10                  15

Gly

<210> SEQ ID NO 21
<211> LENGTH: 17
<212> TYPE: PRT
<213> ORGANISM: Artificial sequence
<220> FEATURE:
<223> OTHER INFORMATION: anti-CD100 variable domain -

<400> SEQUENCE: 21

Arg Val Asn Pro Tyr His Gly Gly Ala Trp Tyr Asn Gln Lys Phe Lys
 1               5                  10                  15

Gly

<210> SEQ ID NO 22
<211> LENGTH: 17
<212> TYPE: PRT
<213> ORGANISM: Artificial sequence
<220> FEATURE:
<223> OTHER INFORMATION: anti-CD100 variable domain -
```

```
<400> SEQUENCE: 22

Arg Val Asn Pro Tyr His Gly Gly Ala Thr Phe Asn Gln Lys Phe Lys
1               5                   10                  15

Gly

<210> SEQ ID NO 23
<211> LENGTH: 17
<212> TYPE: PRT
<213> ORGANISM: Artificial sequence
<220> FEATURE:
<223> OTHER INFORMATION: anti-CD100 variable domain -

<400> SEQUENCE: 23

Arg Val Asn Pro Tyr His Gly Gly Ala Thr Pro Asn Gln Lys Phe Lys
1               5                   10                  15

Gly

<210> SEQ ID NO 24
<211> LENGTH: 17
<212> TYPE: PRT
<213> ORGANISM: Artificial sequence
<220> FEATURE:
<223> OTHER INFORMATION: anti-CD100 variable domain -

<400> SEQUENCE: 24

Arg Val Asn Pro Tyr His Gly Gly Ala Thr Val Asn Gln Lys Phe Lys
1               5                   10                  15

Gly

<210> SEQ ID NO 25
<211> LENGTH: 13
<212> TYPE: PRT
<213> ORGANISM: Artificial sequence
<220> FEATURE:
<223> OTHER INFORMATION: anti-CD100 variable domain -

<400> SEQUENCE: 25

Glu Asp Asn Ser Tyr Asp Gly Tyr Tyr Gly Met Asp Tyr
1               5                   10

<210> SEQ ID NO 26
<211> LENGTH: 13
<212> TYPE: PRT
<213> ORGANISM: Artificial sequence
<220> FEATURE:
<223> OTHER INFORMATION: anti-CD100 variable domain -

<400> SEQUENCE: 26

Glu Glu Asn Ser Tyr Thr Gly Tyr Tyr Gly Met Asp Tyr
1               5                   10

<210> SEQ ID NO 27
<211> LENGTH: 122
<212> TYPE: PRT
<213> ORGANISM: Artificial sequence
<220> FEATURE:
<223> OTHER INFORMATION: anti-CD100 variable domain -

<400> SEQUENCE: 27

Gln Val Gln Leu Val Ala Ser Gly Ala Glu Val Lys Lys Pro Gly Ser
1               5                   10                  15

Ser Val Lys Val Ser Cys Lys Ala Ser Gly Tyr Thr Phe Thr Asp Tyr
                20                  25                  30
```

```
Tyr Met Asp Trp Val Arg Gln Ala Pro Gly Gln Gly Leu Glu Trp Met
            35                  40                  45

Gly Arg Val Asn Pro Tyr His Gly Gly Ala Thr Tyr Asn Gln Lys Phe
     50                  55                  60

Lys Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Glu Glu Asn Ser Tyr Asp Gly Tyr Tyr Gly Met Asp Tyr Trp
             100                 105                 110

Gly Gln Gly Thr Leu Val Thr Val Ser Ser
             115                 120

<210> SEQ ID NO 28
<211> LENGTH: 122
<212> TYPE: PRT
<213> ORGANISM: Artificial sequence
<220> FEATURE:
<223> OTHER INFORMATION: anti-CD100 variable domain -

<400> SEQUENCE: 28

Gln Val Gln Leu Val Gln Ser Gly Ala Glu Val Lys Lys Pro Gly Ser
 1               5                  10                  15

Ser Val Lys Val Ser Cys Thr Ala Ser Gly Tyr Thr Phe Thr Asp Tyr
             20                  25                  30

Tyr Met Asp Trp Val Arg Gln Ala Pro Gly Gln Gly Leu Glu Trp Met
            35                  40                  45

Gly Arg Val Asn Pro Tyr His Gly Gly Ala Thr Tyr Asn Gln Lys Phe
     50                  55                  60

Lys Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Glu Glu Asn Ser Tyr Asp Gly Tyr Tyr Gly Met Asp Tyr Trp
             100                 105                 110

Gly Gln Gly Thr Leu Val Thr Val Ser Ser
             115                 120

<210> SEQ ID NO 29
<211> LENGTH: 122
<212> TYPE: PRT
<213> ORGANISM: Artificial sequence
<220> FEATURE:
<223> OTHER INFORMATION: anti-CD100 variable domain -

<400> SEQUENCE: 29

Gln Val Gln Leu Val Gln Ser Gly Ala Glu Val Lys Lys Pro Gly Ser
 1               5                  10                  15

Ser Val Lys Val Ser Cys Lys Ala Ser Gly Tyr Thr Phe Thr Lys Tyr
             20                  25                  30

Tyr Met Asp Trp Val Arg Gln Ala Pro Gly Gln Gly Leu Glu Trp Met
            35                  40                  45

Gly Arg Val Asn Pro Tyr His Gly Gly Ala Thr Tyr Asn Gln Lys Phe
     50                  55                  60

Lys Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95
```

Ala Arg Glu Glu Asn Ser Tyr Asp Gly Tyr Tyr Gly Met Asp Tyr Trp
            100                 105                 110

Gly Gln Gly Thr Leu Val Thr Val Ser Ser
        115                 120

<210> SEQ ID NO 30
<211> LENGTH: 122
<212> TYPE: PRT
<213> ORGANISM: Artificial sequence
<220> FEATURE:
<223> OTHER INFORMATION: anti-CD100 variable domain -

<400> SEQUENCE: 30

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Tyr
                20                  25                  30

Tyr Met Asp Trp Val Arg Gln Ala Pro Gly Gln Gly Leu Glu Trp Met
            35                  40                  45

Gly Arg Val Asn Pro Tyr His Gly Phe Ala Thr Tyr Asn Gln Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Glu Asn Ser Tyr Asp Gly Tyr Tyr Gly Met Asp Tyr Trp
            100                 105                 110

Gly Gln Gly Thr Leu Val Thr Val Ser Ser
        115                 120

<210> SEQ ID NO 31
<211> LENGTH: 122
<212> TYPE: PRT
<213> ORGANISM: Artificial sequence
<220> FEATURE:
<223> OTHER INFORMATION: anti-CD100 variable domain -

<400> SEQUENCE: 31

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Tyr
                20                  25                  30

Tyr Met Asp Trp Val Arg Gln Ala Pro Gly Gln Gly Leu Glu Trp Met
            35                  40                  45

Gly Arg Val Asn Pro Tyr His Gly Trp Ala Thr Tyr Asn Gln Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Glu Asn Ser Tyr Asp Gly Tyr Tyr Gly Met Asp Tyr Trp
            100                 105                 110

Gly Gln Gly Thr Leu Val Thr Val Ser Ser
        115                 120

<210> SEQ ID NO 32
<211> LENGTH: 122
<212> TYPE: PRT
<213> ORGANISM: Artificial sequence
<220> FEATURE:

<223> OTHER INFORMATION: anti-CD100 variable domain -

<400> SEQUENCE: 32

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Tyr
            20                  25                  30

Tyr Met Asp Trp Val Arg Gln Ala Pro Gly Gln Gly Leu Glu Trp Met
        35                  40                  45

Gly Arg Val Asn Pro Tyr His Gly Tyr Ala Tyr Asn Gln Lys Phe
    50                  55                  60

Lys Gly Arg Val Thr Ile Thr Ala Asp Lys Ser Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Glu Asn Ser Tyr Asp Gly Tyr Tyr Gly Met Asp Tyr Trp
            100                 105                 110

Gly Gln Gly Thr Leu Val Thr Val Ser Ser
        115                 120

<210> SEQ ID NO 33
<211> LENGTH: 122
<212> TYPE: PRT
<213> ORGANISM: Artificial sequence
<220> FEATURE:
<223> OTHER INFORMATION: anti-CD100 variable domain -

<400> SEQUENCE: 33

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Tyr
            20                  25                  30

Tyr Met Asp Trp Val Arg Gln Ala Pro Gly Gln Gly Leu Glu Trp Met
        35                  40                  45

Gly Arg Val Asn Pro Tyr His Gly Gly Thr Tyr Asn Gln Lys Phe
    50                  55                  60

Lys Gly Arg Val Thr Ile Thr Ala Asp Lys Ser Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Glu Asn Ser Tyr Asp Gly Tyr Tyr Gly Met Asp Tyr Trp
            100                 105                 110

Gly Gln Gly Thr Leu Val Thr Val Ser Ser
        115                 120

<210> SEQ ID NO 34
<211> LENGTH: 122
<212> TYPE: PRT
<213> ORGANISM: Artificial sequence
<220> FEATURE:
<223> OTHER INFORMATION: anti-CD100 variable domain -

<400> SEQUENCE: 34

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Tyr
            20                  25                  30

Tyr Met Asp Trp Val Arg Gln Ala Pro Gly Gln Gly Leu Glu Trp Met
        35                  40                  45

```
Gly Arg Val Asn Pro Tyr His Gly Gly Ala Phe Tyr Asn Gln Lys Phe
        50                  55                  60

Lys Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Glu Glu Asn Ser Tyr Asp Gly Tyr Tyr Gly Met Asp Tyr Trp
            100                 105                 110

Gly Gln Gly Thr Leu Val Thr Val Ser Ser
        115                 120

<210> SEQ ID NO 35
<211> LENGTH: 122
<212> TYPE: PRT
<213> ORGANISM: Artificial sequence
<220> FEATURE:
<223> OTHER INFORMATION: anti-CD100 variable domain -

<400> SEQUENCE: 35

Gln Val Gln Leu Val Gln Ser Gly Ala Glu Val Lys Lys Pro Gly Ser
 1               5                  10                  15

Ser Val Lys Val Ser Cys Lys Ala Ser Gly Tyr Thr Phe Thr Asp Tyr
             20                  25                  30

Tyr Met Asp Trp Val Arg Gln Ala Pro Gly Gln Gly Leu Glu Trp Met
             35                  40                  45

Gly Arg Val Asn Pro Tyr His Gly Gly Ala Val Tyr Asn Gln Lys Phe
        50                  55                  60

Lys Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Glu Glu Asn Ser Tyr Asp Gly Tyr Tyr Gly Met Asp Tyr Trp
            100                 105                 110

Gly Gln Gly Thr Leu Val Thr Val Ser Ser
        115                 120

<210> SEQ ID NO 36
<211> LENGTH: 122
<212> TYPE: PRT
<213> ORGANISM: Artificial sequence
<220> FEATURE:
<223> OTHER INFORMATION: anti-CD100 variable domain -

<400> SEQUENCE: 36

Gln Val Gln Leu Val Gln Ser Gly Ala Glu Val Lys Lys Pro Gly Ser
 1               5                  10                  15

Ser Val Lys Val Ser Cys Lys Ala Ser Gly Tyr Thr Phe Thr Asp Tyr
             20                  25                  30

Tyr Met Asp Trp Val Arg Gln Ala Pro Gly Gln Gly Leu Glu Trp Met
             35                  40                  45

Gly Arg Val Asn Pro Tyr His Gly Gly Ala Trp Tyr Asn Gln Lys Phe
        50                  55                  60

Lys Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Glu Glu Asn Ser Tyr Asp Gly Tyr Tyr Gly Met Asp Tyr Trp
            100                 105                 110
```

```
Gly Gln Gly Thr Leu Val Thr Val Ser Ser
        115                 120

<210> SEQ ID NO 37
<211> LENGTH: 122
<212> TYPE: PRT
<213> ORGANISM: Artificial sequence
<220> FEATURE:
<223> OTHER INFORMATION: anti-CD100 variable domain -

<400> SEQUENCE: 37

Gln Val Gln Leu Val Gln Ser Gly Ala Glu Val Lys Lys Pro Gly Ser
  1               5                  10                  15

Ser Val Lys Val Ser Cys Lys Ala Ser Gly Tyr Thr Phe Thr Asp Tyr
             20                  25                  30

Tyr Met Asp Trp Val Arg Gln Ala Pro Gly Gln Gly Leu Glu Trp Met
         35                  40                  45

Gly Arg Val Asn Pro Tyr His Gly Gly Ala Thr Phe Asn Gln Lys Phe
     50                  55                  60

Lys Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Glu Glu Asn Ser Tyr Asp Gly Tyr Tyr Gly Met Asp Tyr Trp
                100                 105                 110

Gly Gln Gly Thr Leu Val Thr Val Ser Ser
        115                 120

<210> SEQ ID NO 38
<211> LENGTH: 122
<212> TYPE: PRT
<213> ORGANISM: Artificial sequence
<220> FEATURE:
<223> OTHER INFORMATION: anti-CD100 variable domain -

<400> SEQUENCE: 38

Gln Val Gln Leu Val Gln Ser Gly Ala Glu Val Lys Lys Pro Gly Ser
  1               5                  10                  15

Ser Val Lys Val Ser Cys Lys Ala Ser Gly Tyr Thr Phe Thr Asp Tyr
             20                  25                  30

Tyr Met Asp Trp Val Arg Gln Ala Pro Gly Gln Gly Leu Glu Trp Met
         35                  40                  45

Gly Arg Val Asn Pro Tyr His Gly Gly Ala Thr Pro Asn Gln Lys Phe
     50                  55                  60

Lys Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Glu Glu Asn Ser Tyr Asp Gly Tyr Tyr Gly Met Asp Tyr Trp
                100                 105                 110

Gly Gln Gly Thr Leu Val Thr Val Ser Ser
        115                 120

<210> SEQ ID NO 39
<211> LENGTH: 122
<212> TYPE: PRT
<213> ORGANISM: Artificial sequence
<220> FEATURE:
<223> OTHER INFORMATION: anti-CD100 variable domain -
```

<400> SEQUENCE: 39

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Tyr
            20                  25                  30

Tyr Met Asp Trp Val Arg Gln Ala Pro Gly Gln Gly Leu Glu Trp Met
        35                  40                  45

Gly Arg Val Asn Pro Tyr His Gly Gly Ala Thr Val Asn Gln Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Glu Asn Ser Tyr Asp Gly Tyr Tyr Gly Met Asp Tyr Trp
            100                 105                 110

Gly Gln Gly Thr Leu Val Thr Val Ser Ser
        115                 120

<210> SEQ ID NO 40
<211> LENGTH: 122
<212> TYPE: PRT
<213> ORGANISM: Artificial sequence
<220> FEATURE:
<223> OTHER INFORMATION: anti-CD100 variable domain -

<400> SEQUENCE: 40

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Tyr
            20                  25                  30

Tyr Met Asp Trp Val Arg Gln Ala Pro Gly Gln Gly Leu Glu Trp Met
        35                  40                  45

Gly Arg Val Asn Pro Tyr His Gly Gly Ala Thr Tyr Asn Gln Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Asp Asn Ser Tyr Asp Gly Tyr Tyr Gly Met Asp Tyr Trp
            100                 105                 110

Gly Gln Gly Thr Leu Val Thr Val Ser Ser
        115                 120

<210> SEQ ID NO 41
<211> LENGTH: 122
<212> TYPE: PRT
<213> ORGANISM: Artificial sequence
<220> FEATURE:
<223> OTHER INFORMATION: anti-CD100 variable domain -

<400> SEQUENCE: 41

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Tyr
            20                  25                  30

Tyr Met Asp Trp Val Arg Gln Ala Pro Gly Gln Gly Leu Glu Trp Met
        35                  40                  45

Gly Arg Val Asn Pro Tyr His Gly Gly Ala Thr Tyr Asn Gln Lys Phe

```
                50                  55                  60
Lys Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Glu Glu Asn Ser Tyr Thr Gly Tyr Tyr Gly Met Asp Tyr Trp
                100                 105                 110

Gly Gln Gly Thr Leu Val Thr Val Ser Ser
            115                 120

<210> SEQ ID NO 42
<211> LENGTH: 122
<212> TYPE: PRT
<213> ORGANISM: Artificial sequence
<220> FEATURE:
<223> OTHER INFORMATION: anti-CD100 variable domain -

<400> SEQUENCE: 42

Gln Val Gln Leu Val Ala Ser Gly Ala Glu Val Lys Lys Pro Gly Ser
 1               5                  10                  15

Ser Val Lys Val Ser Cys Lys Ala Ser Gly Tyr Thr Phe Thr Lys Tyr
                20                  25                  30

Tyr Met Asp Trp Val Arg Gln Ala Pro Gly Gln Gly Leu Glu Trp Met
             35                  40                  45

Gly Arg Val Asn Pro Tyr His Gly Gly Ala Thr Tyr Asn Gln Lys Phe
 50                  55                  60

Lys Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Glu Glu Asn Ser Tyr Asp Gly Tyr Tyr Gly Met Asp Tyr Trp
                100                 105                 110

Gly Gln Gly Thr Leu Val Thr Val Ser Ser
            115                 120

<210> SEQ ID NO 43
<211> LENGTH: 122
<212> TYPE: PRT
<213> ORGANISM: Artificial sequence
<220> FEATURE:
<223> OTHER INFORMATION: anti-CD100 variable domain -

<400> SEQUENCE: 43

Gln Val Gln Leu Val Gln Ser Gly Ala Glu Val Lys Lys Pro Gly Ser
 1               5                  10                  15

Ser Val Lys Val Ser Cys Thr Ala Ser Gly Tyr Thr Phe Thr Lys Tyr
                20                  25                  30

Tyr Met Asp Trp Val Arg Gln Ala Pro Gly Gln Gly Leu Glu Trp Met
             35                  40                  45

Gly Arg Val Asn Pro Tyr His Gly Gly Ala Thr Tyr Asn Gln Lys Phe
 50                  55                  60

Lys Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Glu Glu Asn Ser Tyr Asp Gly Tyr Tyr Gly Met Asp Tyr Trp
                100                 105                 110

Gly Gln Gly Thr Leu Val Thr Val Ser Ser
```

115                 120

<210> SEQ ID NO 44
<211> LENGTH: 122
<212> TYPE: PRT
<213> ORGANISM: Artificial sequence
<220> FEATURE:
<223> OTHER INFORMATION: anti-CD100 variable domain -

<400> SEQUENCE: 44

Gln Val Gln Leu Val Ala Ser Gly Ala Glu Val Lys Lys Pro Gly Ser
 1               5                  10                  15

Ser Val Lys Val Ser Cys Lys Ala Ser Gly Tyr Thr Phe Thr Asp Tyr
            20                  25                  30

Tyr Met Asp Trp Val Arg Gln Ala Pro Gly Gln Gly Leu Glu Trp Met
        35                  40                  45

Gly Arg Val Asn Pro Tyr His Gly Phe Ala Tyr Asn Gln Lys Phe
    50                  55                  60

Lys Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                85                  90                  95

Ala Arg Glu Glu Asn Ser Tyr Asp Gly Tyr Tyr Gly Met Asp Tyr Trp
            100                 105                 110

Gly Gln Gly Thr Leu Val Thr Val Ser Ser
        115                 120

<210> SEQ ID NO 45
<211> LENGTH: 122
<212> TYPE: PRT
<213> ORGANISM: Artificial sequence
<220> FEATURE:
<223> OTHER INFORMATION: anti-CD100 variable domain -

<400> SEQUENCE: 45

Gln Val Gln Leu Val Ala Ser Gly Ala Glu Val Lys Lys Pro Gly Ser
 1               5                  10                  15

Ser Val Lys Val Ser Cys Lys Ala Ser Gly Tyr Thr Phe Thr Asp Tyr
            20                  25                  30

Tyr Met Asp Trp Val Arg Gln Ala Pro Gly Gln Gly Leu Glu Trp Met
        35                  40                  45

Gly Arg Val Asn Pro Tyr His Gly Tyr Ala Thr Tyr Asn Gln Lys Phe
    50                  55                  60

Lys Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                85                  90                  95

Ala Arg Glu Glu Asn Ser Tyr Asp Gly Tyr Tyr Gly Met Asp Tyr Trp
            100                 105                 110

Gly Gln Gly Thr Leu Val Thr Val Ser Ser
        115                 120

<210> SEQ ID NO 46
<211> LENGTH: 122
<212> TYPE: PRT
<213> ORGANISM: Artificial sequence
<220> FEATURE:
<223> OTHER INFORMATION: anti-CD100 variable domain -

<400> SEQUENCE: 46

```
Gln Val Gln Leu Val Ala Ser Gly Ala Glu Val Lys Lys Pro Gly Ser
  1               5                  10                  15

Ser Val Lys Val Ser Cys Lys Ala Ser Gly Tyr Thr Phe Thr Asp Tyr
             20                  25                  30

Tyr Met Asp Trp Val Arg Gln Ala Pro Gly Gln Gly Leu Glu Trp Met
         35                  40                  45

Gly Arg Val Asn Pro Tyr His Gly Gly Ala Phe Tyr Asn Gln Lys Phe
 50                  55                  60

Lys Gly Arg Val Thr Ile Thr Ala Asp Lys Ser Ser Thr Ala Tyr
 65                  70                  75                  80

Met Glu Leu Ser Ser Leu Arg Ser Glu Asp Thr Ala Val Tyr Tyr Cys
             85                  90                  95

Ala Arg Glu Glu Asn Ser Tyr Asp Gly Tyr Tyr Gly Met Asp Tyr Trp
               100                 105                 110

Gly Gln Gly Thr Leu Val Thr Val Ser Ser
            115                 120
```

<210> SEQ ID NO 47
<211> LENGTH: 122
<212> TYPE: PRT
<213> ORGANISM: Artificial sequence
<220> FEATURE:
<223> OTHER INFORMATION: anti-CD100 variable domain -

<400> SEQUENCE: 47

```
Gln Val Gln Leu Val Ala Ser Gly Ala Glu Val Lys Lys Pro Gly Ser
  1               5                  10                  15

Ser Val Lys Val Ser Cys Lys Ala Ser Gly Tyr Thr Phe Thr Asp Tyr
             20                  25                  30

Tyr Met Asp Trp Val Arg Gln Ala Pro Gly Gln Gly Leu Glu Trp Met
         35                  40                  45

Gly Arg Val Asn Pro Tyr His Gly Gly Ala Thr Phe Asn Gln Lys Phe
 50                  55                  60

Lys Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
             85                  90                  95

Ala Arg Glu Glu Asn Ser Tyr Asp Gly Tyr Tyr Gly Met Asp Tyr Trp
               100                 105                 110

Gly Gln Gly Thr Leu Val Thr Val Ser Ser
            115                 120
```

<210> SEQ ID NO 48
<211> LENGTH: 122
<212> TYPE: PRT
<213> ORGANISM: Artificial sequence
<220> FEATURE:
<223> OTHER INFORMATION: anti-CD100 variable domain -

<400> SEQUENCE: 48

```
Gln Val Gln Leu Val Ala Ser Gly Ala Glu Val Lys Lys Pro Gly Ser
  1               5                  10                  15

Ser Val Lys Val Ser Cys Lys Ala Ser Gly Tyr Thr Phe Thr Asp Tyr
             20                  25                  30

Tyr Met Asp Trp Val Arg Gln Ala Pro Gly Gln Gly Leu Glu Trp Met
         35                  40                  45

Gly Arg Val Asn Pro Tyr His Gly Gly Ala Thr Val Asn Gln Lys Phe
 50                  55                  60
```

```
Lys Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Glu Glu Asn Ser Tyr Asp Gly Tyr Tyr Gly Met Asp Tyr Trp
            100                 105                 110

Gly Gln Gly Thr Leu Val Thr Val Ser Ser
            115                 120

<210> SEQ ID NO 49
<211> LENGTH: 122
<212> TYPE: PRT
<213> ORGANISM: Artificial sequence
<220> FEATURE:
<223> OTHER INFORMATION: anti-CD100 variable domain -

<400> SEQUENCE: 49

Gln Val Gln Leu Val Gln Ser Gly Ala Glu Val Lys Lys Pro Gly Ser
  1               5                  10                  15

Ser Val Lys Val Ser Cys Thr Ala Ser Gly Tyr Thr Phe Thr Asp Tyr
                 20                  25                  30

Tyr Met Asp Trp Val Arg Gln Ala Pro Gly Gln Gly Leu Glu Trp Met
             35                  40                  45

Gly Arg Val Asn Pro Tyr His Gly Phe Ala Thr Tyr Asn Gln Lys Phe
 50                  55                  60

Lys Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Glu Glu Asn Ser Tyr Asp Gly Tyr Tyr Gly Met Asp Tyr Trp
            100                 105                 110

Gly Gln Gly Thr Leu Val Thr Val Ser Ser
            115                 120

<210> SEQ ID NO 50
<211> LENGTH: 122
<212> TYPE: PRT
<213> ORGANISM: Artificial sequence
<220> FEATURE:
<223> OTHER INFORMATION: anti-CD100 variable domain -

<400> SEQUENCE: 50

Gln Val Gln Leu Val Gln Ser Gly Ala Glu Val Lys Lys Pro Gly Ser
  1               5                  10                  15

Ser Val Lys Val Ser Cys Thr Ala Ser Gly Tyr Thr Phe Thr Asp Tyr
                 20                  25                  30

Tyr Met Asp Trp Val Arg Gln Ala Pro Gly Gln Gly Leu Glu Trp Met
             35                  40                  45

Gly Arg Val Asn Pro Tyr His Gly Tyr Ala Thr Tyr Asn Gln Lys Phe
 50                  55                  60

Lys Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Glu Glu Asn Ser Tyr Asp Gly Tyr Tyr Gly Met Asp Tyr Trp
            100                 105                 110

Gly Gln Gly Thr Leu Val Thr Val Ser Ser
            115                 120
```

-continued

```
<210> SEQ ID NO 51
<211> LENGTH: 122
<212> TYPE: PRT
<213> ORGANISM: Artificial sequence
<220> FEATURE:
<223> OTHER INFORMATION: anti-CD100 variable domain -

<400> SEQUENCE: 51

Gln Val Gln Leu Val Gln Ser Gly Ala Glu Val Lys Lys Pro Gly Ser
1               5                   10                  15

Ser Val Lys Val Ser Cys Thr Ala Ser Gly Tyr Thr Phe Thr Asp Tyr
            20                  25                  30

Tyr Met Asp Trp Val Arg Gln Ala Pro Gly Gln Gly Leu Glu Trp Met
        35                  40                  45

Gly Arg Val Asn Pro Tyr His Gly Gly Ala Phe Tyr Asn Gln Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Glu Asn Ser Tyr Asp Gly Tyr Tyr Gly Met Asp Tyr Trp
            100                 105                 110

Gly Gln Gly Thr Leu Val Thr Val Ser Ser
        115                 120

<210> SEQ ID NO 52
<211> LENGTH: 122
<212> TYPE: PRT
<213> ORGANISM: Artificial sequence
<220> FEATURE:
<223> OTHER INFORMATION: anti-CD100 variable domain -

<400> SEQUENCE: 52

Gln Val Gln Leu Val Gln Ser Gly Ala Glu Val Lys Lys Pro Gly Ser
1               5                   10                  15

Ser Val Lys Val Ser Cys Thr Ala Ser Gly Tyr Thr Phe Thr Asp Tyr
            20                  25                  30

Tyr Met Asp Trp Val Arg Gln Ala Pro Gly Gln Gly Leu Glu Trp Met
        35                  40                  45

Gly Arg Val Asn Pro Tyr His Gly Gly Ala Thr Phe Asn Gln Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Glu Asn Ser Tyr Asp Gly Tyr Tyr Gly Met Asp Tyr Trp
            100                 105                 110

Gly Gln Gly Thr Leu Val Thr Val Ser Ser
        115                 120

<210> SEQ ID NO 53
<211> LENGTH: 122
<212> TYPE: PRT
<213> ORGANISM: Artificial sequence
<220> FEATURE:
<223> OTHER INFORMATION: anti-CD100 variable domain -

<400> SEQUENCE: 53

Gln Val Gln Leu Val Gln Ser Gly Ala Glu Val Lys Lys Pro Gly Ser
1               5                   10                  15
```

Ser Val Lys Val Ser Cys Thr Ala Ser Gly Tyr Thr Phe Thr Asp Tyr
            20                  25                  30

Tyr Met Asp Trp Val Arg Gln Ala Pro Gly Gln Gly Leu Glu Trp Met
        35                  40                  45

Gly Arg Val Asn Pro Tyr His Gly Gly Ala Thr Val Asn Gln Lys Phe
50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Glu Asn Ser Tyr Asp Gly Tyr Tyr Gly Met Asp Tyr Trp
            100                 105                 110

Gly Gln Gly Thr Leu Val Thr Val Ser Ser
        115                 120

<210> SEQ ID NO 54
<211> LENGTH: 122
<212> TYPE: PRT
<213> ORGANISM: Artificial sequence
<220> FEATURE:
<223> OTHER INFORMATION: anti-CD100 variable domain -

<400> SEQUENCE: 54

Gln Val Gln Leu Val Gln Ser Gly Ala Glu Val Lys Lys Pro Gly Ser
 1               5                  10                  15

Ser Val Lys Val Ser Cys Thr Ala Ser Gly Tyr Thr Phe Thr Asp Tyr
            20                  25                  30

Tyr Met Asp Trp Val Arg Gln Ala Pro Gly Gln Gly Leu Glu Trp Met
        35                  40                  45

Gly Arg Val Asn Pro Tyr His Gly Gly Ala Thr Tyr Asn Gln Lys Phe
50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Glu Asn Ser Tyr Thr Gly Tyr Tyr Gly Met Asp Tyr Trp
            100                 105                 110

Gly Gln Gly Thr Leu Val Thr Val Ser Ser
        115                 120

<210> SEQ ID NO 55
<211> LENGTH: 75
<212> TYPE: DNA
<213> ORGANISM: Artificial sequence
<220> FEATURE:
<223> OTHER INFORMATION: anti-CD100 variable domain -

<400> SEQUENCE: 55
caggtgcagc tggtgcagtc tggggctgag gtgaagaagc ctgggtcctc cgtgaaggtc      60
tcctgcaagg cttct                                                      75

<210> SEQ ID NO 56
<211> LENGTH: 30
<212> TYPE: DNA
<213> ORGANISM: Artificial sequence
<220> FEATURE:
<223> OTHER INFORMATION: anti-CD100 variable domain -

<400> SEQUENCE: 56

-continued ggatacacat tcacggacta ctacatggac                                    30

<210> SEQ ID NO 57
<211> LENGTH: 51
<212> TYPE: DNA
<213> ORGANISM: Artificial sequence
<220> FEATURE:
<223> OTHER INFORMATION: anti-CD100 variable domain -

<400> SEQUENCE: 57
cgggttaatc cttaccatgg tggcgctacc tacaaccaga agttcaaggg c            51

<210> SEQ ID NO 58
<211> LENGTH: 39
<212> TYPE: DNA
<213> ORGANISM: Artificial sequence
<220> FEATURE:
<223> OTHER INFORMATION: anti-CD100 variable domain -

<400> SEQUENCE: 58
gaggagaatt cttacgacgg ttattatggt atggactac                          39

<210> SEQ ID NO 59
<211> LENGTH: 366
<212> TYPE: DNA
<213> ORGANISM: Artificial sequence
<220> FEATURE:
<223> OTHER INFORMATION: anti-CD100 variable domain -

<400> SEQUENCE: 59
caggtgcagc tggtgcagtc tggggctgag gtgaagaagc ctgggtcctc ggtgaaggtc   60
tcctgcaagg cttctggata cacattcacg gactactaca tggactgggt gcgacaggcc  120
cctggacaag gcttgagtg gattggacgt gttaatcctt accatggtgg cgctacctac   180
aaccagaagt tcaagggcaa ggccacaatt accgttgaca atccacgag cacagcctac   240 atggagctga gcagcctgag atctgaggac acggccgtgt attactgtgc gagagaggag  300
aattcttacg acggttatta tggtatggac tactggggcc aagggaccct ggtcaccgtc  360
tcctca                                                             366

<210> SEQ ID NO 60
<211> LENGTH: 366
<212> TYPE: DNA
<213> ORGANISM: Artificial sequence
<220> FEATURE:
<223> OTHER INFORMATION: anti-CD100 variable domain -

<400> SEQUENCE: 60
caggtgcagc tggtgcagtc tggggctgag gtgaagaagc ctgggtcctc cgtgaaggtc   60
tcctgcaagg cttctggata cacattcacg gactactaca tggactgggt gcgacaggcc  120
cctggacaag gcttgagtg gatgggacgg gttaatcctt accatggtgg cgctacctac   180
aaccagaagt tcaagggcag ggtgacaatt accgccgaca atccacgag cacagcctac   240 atggagctga gcagcctgag atctgaggac acggccgtgt attactgtgc gagagaggag  300
aattcttacg acggttatta tggtatggac tactggggcc aagggaccct ggtcaccgtc  360
tcctca                                                             366

<210> SEQ ID NO 61
<211> LENGTH: 366
<212> TYPE: DNA
<213> ORGANISM: Artificial sequence
<220> FEATURE:

<223> OTHER INFORMATION: anti-CD100 variable domain -

<400> SEQUENCE: 61

```
gaggtccaac tgcagcagtc tggacctgag ttggtgaagc ctggggcttc agtgaagatg      60
tcctgtaagg cttctggata cacattcacg gactactaca tggactgggt gaagcagagc     120
cacggagaaa gctttgagtg gattggacgt gttaatcctt accatggtgg cgctacctac     180
aaccagaagt tcaagggcaa ggccacattg actgttgaca gtcctccag  aacagcctac     240
atggaactca acagcctgac atatgaggac tccgcggtct attactgtgc aagagaggag     300
aattcttacg acggttatta tggtatggac tactggggcc aagggaccac ggtcaccgtc     360
tcctca                                                                366
```

<210> SEQ ID NO 62
<211> LENGTH: 354
<212> TYPE: DNA
<213> ORGANISM: Artificial sequence
<220> FEATURE:
<223> OTHER INFORMATION: anti-CD100 variable domain -

<400> SEQUENCE: 62

```
gaggtgaagc tgcaggagtc tggaggtggc ctggtgcagc ctggaggatc cctgaatctc      60
tcctgtacag cctcaggatt cgattttagt agatactgga tgagttgggc tcggcaggct     120
ccagggaaag ggcaggaatg gattggagaa attaatccag gaagcagtac gataaactat     180
acgccatctc taaaggataa attcatcatc tccagagaca cgccaaaaa  tacgctgtac     240
ctgcaaatga gcaaagtgag atctgaggac acagccctt  attactgtgc aagacagggg     300
acttattata ctatggacta ctggggccaa gggaccacgg tcaccgtctc ctca           354
```

<210> SEQ ID NO 63
<211> LENGTH: 339
<212> TYPE: DNA
<213> ORGANISM: Artificial sequence
<220> FEATURE:
<223> OTHER INFORMATION: L284 Humanized murine anti-CD100 light chain

<400> SEQUENCE: 63

```
gacatcgtga tgacccagtc tccactctcc ctgcccgtct ctcctggaga gccggccacc      60
atcaactgca gtccagcca  gagtctgttt aacagtggaa tcaaaagaa  ctacttggcc     120
tggtacctgc agaagccagg gcagcctcct aaactgttga tctacggggc atccactagg     180
gaatctgggg tccctgatcg cttcagtggc agcgggtctg ggacagattt cactctcacc     240
atcagcagcc tgcaggctga agatgtggca gtttattact gtcagaatga tcatacttat     300
ccgtacactt ttggccaggg gaccaagctc gagatcaaa                            339
```

<210> SEQ ID NO 64
<211> LENGTH: 339
<212> TYPE: DNA
<213> ORGANISM: Artificial sequence
<220> FEATURE:
<223> OTHER INFORMATION: L124284 - humanized murine anti-CD100 light
      chain

<400> SEQUENCE: 64

```
gacattgtgc taacccagtc tccatcctcc ctgagtgtgt cagcaggaga gaaggtcact      60
atggactgca gtccagtca  gagtctgttt aacagtggaa tcaaaagaa  ctacttggcc     120
tggtaccacc agaaaccagg gcagcctcct aaactgttga tctacggggc atccactagg     180
gaatctgggg tccctgatcg cttcacaggc agtggatctg gaaccgattt cactcttacc     240
```

```
atcagcagtg tgcaggctga agacctggca gtttattact gtcaaaatga tcatacttat        300
ccgtacacgt tcggagggg gaccaagctc gagatcaaa                                339

<210> SEQ ID NO 65
<211> LENGTH: 318
<212> TYPE: DNA
<213> ORGANISM: Artificial sequence
<220> FEATURE:
<223> OTHER INFORMATION: anti-CD100 variable domain -

<400> SEQUENCE: 65
gacatccaga tgacgcagtc tccatcctca ctgtctgcat ctctgggagg caaagtcacc         60
atcacttgca aggcaagcca agacattaac aagtatatat cttggtacca agacaagcct        120
ggaaaaggtc ctgggctgct catacattac acatctacat tacagccagg catcccatca        180
aggttcagtg aagtgggtc tgggagagat tattccttca gcatcagcaa cctggagcct        240
gaagatattg caacttatta ttgtctacag tatgataatc tgtacacgtt cggaggggg         300 accaagctcg agatcaaa                                                      318
```